US006492343B1

(12) United States Patent
Reddy et al.

(10) Patent No.: US 6,492,343 B1
(45) Date of Patent: Dec. 10, 2002

(54) PORCINE ADENOVIRUS TYPE 3 GENOME

(75) Inventors: Police Seshidhar Reddy, Gaithersburg, MD (US); Suresh Kumar Tikoo, Saskatoon (CA); Lorne A. Babiuk, Saskatoon (CA)

(73) Assignee: University of Saskatchewan, Saskatoon (CA)

( * ) Notice: Subject to any disclaimer, the term of this patent is extended or adjusted under 35 U.S.C. 154(b) by 0 days.

(21) Appl. No.: 09/292,034

(22) Filed: Apr. 14, 1999

Related U.S. Application Data

(60) Provisional application No. 60/081,882, filed on Apr. 15, 1998.

(51) Int. Cl.[7] .................................................. A01N 43/04

(52) U.S. Cl. ...................... 514/44; 435/320.1; 435/455; 435/325; 435/471; 435/488; 435/69.1

(58) Field of Search ...................... 536/23.1; 435/320.1, 435/325, 440, 455, 456, 235.1, 69.1, 471, 488; 424/93.2, 93.1, 93.21; 514/44

(56) References Cited

FOREIGN PATENT DOCUMENTS

| | | |
|---|---|---|
| EP | 0259149 | 3/1988 |
| WO | WO 99/08706 | 2/1999 |

OTHER PUBLICATIONS

Verma et al. Gene Therapy–Promises, Problems, and Prospects. Nature, vol. 389, pp. 239–242, Sep. 18, 1997.*

Eck et al. Gene–Based Therapy. Goodman & Gilman's The Pharmacological Basis of Therapeutics, 9th Edition, Chapter 5, pp. 77–101, 1996.*

McCoy et al. Nucleotide and Amino Acid Sequence Analysis of the 100K Protein of a Serotype 3 Porcine Adenovirus. DNA Sequence–The Journal of Sequencing and Mapping, vol. 8, pp. 59–61, 1997.*

McCoy et al. Porcine Adenovirus 3 hexon gene. GeBank, Accession No. U34592, Jun. 12, 1996.*

Kleiboeker, S. B. et al. (1993). "Genomic cloning and restriction site mapping of a porcine adenovirus isolate: Demonstration of genomic stability in porcine adenovirus" *Arch. Virol.* 133(3–4):357–368.

Park, J. H. et al. (Jun. 1998). "Sequence analysis of the early region 1B (E1B) of porcine adenovirus type 3" *RDA J. Veterinary Sci.* 40(1):19–25 (Abstract only).

Reddy, P. S. et al. (Nov. 1998). "Sequence and transcription map analysis of early region–1 of porcine adenovirus type–3" *Virus Res.* 58(1–2):97–106.

Reddy, P. S. et al. (Nov. 25, 1998). "Nucleotide sequence and transcription map or porcine adenovirus type–3" *Virol.* 251(2):414–426.

Reddy, P. S. et al. (Mar. 1999). "Development of porcine adenovirus–3 as an expression vector" *J. Gen. Virol.* 80(3):563–570.

*Animal Cell Culture* Ed. R. Freshney. Oxford: IRL Press, 1986, Title page and table of contents only.

*Antibodies: A Laboratory Manual*, Eds. Harlow & Lane. New York: Cold Spring Harbor Press, 1988. Title page and table of contents only.

Ball et al. (1988). "Identification of Mouse Adenovirus Type 1 Early Region 1: DNA Sequence and a Conserved Trans-activating Function," *Journal of Virology* vol. 62, No. 11, 3947–3957.

Berk, Arnold and Sharp, Phillip. (1977). "Sizing and Mapping of Early Adenovirus mRNAs by Gel Electrophoresis of S1 Endonuclease–Digested Hybrids," *Cell* vol. 12, 721–732.

Brennan, Sean and Savage, Robert. (1990). "Embryonic transcriptional activation of a *Xenopus* cytoskeletal actine gene does not require a serum response element," *Roux's Arch Dev. Biol* vol. 199, 89–96.

Chartier, C. et al. (1996). "Efficient Generation of Recombinant Adenovirus Vectors by Homologous Recombination in *Escherichia coli," Journal of Virology* vol. 70, No. 7, 4805–4810.

Chiocca, S., et al. (1996). "The Complete DNA Sequence and Genomic Organization of the Avian Adenovirus CELO," *Journal of Virology* vol. 70, No. 5, 2939–2949.

*Current Protocols In Molecular Biology*, Eds. Ausubel et al. New York: John Wiley & Sons, 1995, Title page and table of contents only.

Derbyshire, et al. (1975). "Serological and Pathogenicity Studies with Some Unclassified Porcine Adenoviruses," *J. Comp. Path.* vol. 85, 437–443.

Derbyshire, J.B. "Adenovirus" *Diseases of Swine*, Ed. Leman, et al 7th ed. Ames. IA: Iowa State University Press, pp. 225–227, 1992.

*DNA Cloning: A Practical Approach*, Ed. D. Glover. Oxford: IRL Press, vols. I, II, & III, 1985, 1987. Title page and table of contents only.

Fallaux, et al. (1996). "Characterization of 911: A New Helper Cell Line for the Titration and Propagation of Early Region 1–Deleted Adenoviral Vectors," *Human Gene Therapy* vol. 7, 215–222.

(List continued on next page.)

*Primary Examiner*—James Martinell
(74) *Attorney, Agent, or Firm*—Morrison & Foerster LLP

(57) ABSTRACT

The complete nucleotide sequence of the genome of porcine adenovirus type 3 (PAV-3) is provided. Methods for construction of infectious PAV genomes by homologous recombination in procaryotic cells are provided. Recombinant PAV viruses are obtained by transfection of mammalian cells with recombinant PAV genomes. The PAV-3 genome can be used as a vector for the expression of heterologous nucleotide sequences, for example, for the preparation and administration of subunit vaccines to swine or other mammals. In addition, PAV-3 vectors can be used for gene therapy and expression of heterologous polypeptides. PAV-3 genome sequences can also be used for diagnostic purposes, to detect the presence of PAV-3 DNA in a subject or biological sample.

44 Claims, 14 Drawing Sheets

OTHER PUBLICATIONS

Fallaux, et al. (1998). "New Helper Cells and Matched Early Region 1–Deleted Adenovirus Vectors Prevent Generation of Replication–Competent Adenoviruses," *Human Gene Therapy* vol. 9, 1909–1917.

Gerard, Robert and Meidell, Robert. (1993). "Adenovirus–Mediated Gene Transfer," *TCM* vol. 3, No. 5, 171–177.

Gorman, et al. (1982). "Recombinant Genomes Which Express Chloramphenicol Acetyltransferase in Mammalian Cells," *Molecular and Cellular Biology* vol. 2, No. 9, 1044–1051.

Graham, et al. (1977). "Characteristics of a Human Cell Line Transformed by DNA from Human Adenovirus Type 5," *J. General Virology* vol. 36, 59–72.

Graham, et al. (1991). "Gene transfer and expression protocols," *Methods in Molecular Biology* vol. 7, 109–128.

Grunhaus, A. and Horwitz, M.S. (1992). "Adenoviruses as cloning vectors," seminars in *Virology* vol. 3, 237–252.

Hanahan, Douglas. (1983). "Studies on Transformation of *Escherichia coli* with Plasmids," *J. Mol. Biol.* vol. 166, 557–580.

Hehir, et al. (1996). "Molecular Characterization of Replication–Competent Variants of Adenovirus Vectors and Genome Modifications To Prevent Their Occurrence," *Journal of Virology* vol. 70, No. 12, 8459–8467.

Hirahara et al. (1989). "Isolation of Porcine Adenovirus from the Respiratory Tract of Pigs in Japan," *Jpn. J. Vet. Sci.* vol. 52, No. 2, 407–409.

Hirt. (1967). "Selective Extraction of Polyoma DNA from Infected Mouse Cell Cultures," *J. Mol. Biol.* vol. 26, 365–369.

Imler, et al. (1995) "Novel complementation cells lines derived from human lung carcinoma A549 cells support the growth of E1–deleted adenovirus vectors," *Gene Therap.* vol. 3, 75–84.

Imler, et al. (1995) "Trans–Complementation of E1–Deleted Adenovirus: A New Vector to Reduce the Possibility of Codissemination of Wild–Type and Recombinant Adenoviruses," *Human Gene Therapy* vol. 6, 711–721.

Kleiboeker, S. (1994). "Sequence analysis of putative E3, pVIII, and fiber genomic regions of a porcine adenovirus," *Virus Research* vol. 31, 17–25.

Kleiboeker, S. (1995). "Identification and sequence analysis of the E1 genomic region of a porcine adenovirus," *Virus Research* vol. 36, 259–268.

Kleiboeker, S. (1995). "Sequence analysis of the fiber genomic region of a porcine adenovirus predicts a novel fiber protein," *Virus Research* vol. 39, 299–309.

Klonjowski, et al. (1997). "A Recombinant E1–Deleted Canine Adenoviral Vector Capable of Transduction and Expression of a Transgene in Human–Derived Cells and *In Vivo,*" *Human Gene Therapy* vol. 8, 2103–2115.

Kunkel, et al. (1987). "Rapid and Efficient Site–Specific Mutagenesis without Phenotypic Selection," *Methods in Enzymology* vol. 154, 367–382.

Ma, Yuliang and Mathews, Michael B. (1996). "Structure, Function, and Evolution of Adenovirus–Associated RNA: a Phylogenetic Approach," *Journal of Virology* vol. 70, No. 8, 5083–5099.

Maniatis, et al., *Molecular Cloning: A Laboratory Manual*, New York: Cold Spring Harbor Press, 1982. Title page and table of contents only.

McCoy, et al. (1996). "Genomic location and nucleotide sequence of a porcine adenovirus penton base gene," *Archives of Virology* vol. 141, 1367–1375.

McCoy, et al. (1996). "Nucleotide and amino acid sequence analysis of the procine adenovirus 23K protein," *DNA Sequence–The Journal of Sequencing and Mapping* vol. 6, 251–254.

*Methods in Nonradioactive Detection*, Ed. Howard. Norwalk: Appleton & Lange, 1993. Title page and table of contents only.

Morrison, et al. (1997). "Complete DNA sequence of canine adenovirus type 1," *Journal of General Virology* vol. 78, 873–878.

*Nonisotopic DNA Probe Techniques*, Ed. Kricka, San Diego: Academic Press, 1992. Title page and table of contents only.

*Nonradioactive Labeling and Detection of Biomolecules*, Ed. Kessler. Berlin: Springer–Verlag, 1992. Title page and table of contents only.

*Nucleic Acid Hybridisation: A Practical Approach*, Eds. B.D. Hames and S.J. Higgins. Oxford: IRL Press Ltd., 1985. Title page and table of contents only.

*Oligonycleotide Synthesis*, Ed. M.J. Gait, Oxford: IRL Press, 1984. Title page or table of contents only.

Perbal, Bernard. *A Practical Guide to Molecular Cloning*, New York: John Wiley & Sons, 1984. Title page and table of contents only.

Reddy, et al. (1995), "Comparison of the Inverted Terminal Repetition Sequences from Five Porcine Adenovirus Serotypes," *Virology* vol. 212, 237–239.

Reddy, et al. (1995). "Molecular cloning and physical mapping of porcine adenovirus types 1 and 2," *Archives of Virology* vol. 140, 195–200.

Reddy, et al. (1995). "Sequence analysis of putative pVIII, E3 and fibre regions of porcine adenovirus type 3," *Virus Research* vol. 36, 97–106.

Reddy, et al. (1996). "Porcine adenoviruses types 1, 2 and 3 have short and simple early E–3 regions," *Virus Research* vol. 43, 99–109.

Reddy, et al. (1997). "Characterization of the Early Region 4 of Porcine Adenovirus Type 3," *Virus Genes* vol. 15, No. 1, 87–90.

Reddy, et al. (1998). "Nucleotide Sequence, Genome Organization, and Transcription Map of Bovine Adenovirus Type 3," *Journal of Virology* vol. 72, No. 2, 1394–1402.

Reddy, et al. (1993). "Restriction Endonuclease Analysis and Molecular Cloning of Porcine Adenovirus Type 3," *Intervirology* vol. 36, 161–168.

Sambrook, et al., *Molecular Cloning: A Laboratory Manual*, $2^{nd}$ ed. New York: Cold Spring Harbor Laboratory Press, vols. I, II & III, 1989. Title page and table of contents only.

Shaw, W.V. (1975). "Chloramphenicol Acetyltransferase from Chloramphenicol–Resistant Bacteria" *Meth. in Enzymology* vol. 43, 737–755.

*Transcription and Translation*, Eds. B. Hames and S. Higgins. Oxford: IRL Press, 1984. Title page and table of contents only.

Tuboly, et al. (1993). "Potential viral vectors for the stimulation of mucosal antibody responses against enteric viral antigens in pigs," *Research in Veterinary Science* vol. 54, 345–350.

*Viral Diarrheas of Man and Animals*, Eds. Saif et al., "Enteric Virus Vaccines: Theoretical Considerations, Current Status, and Future Approaches," Chapter 14, pp. 313–329, 1990.

Vrati, et al. (1996). "Unique Genome Arrangement of an Ovine Adenovirus: Identification of New Proteins and Proteinase Cleavage Sites," *Virology* vol. 220, 186–199.

Xiang, et al. (1996). "A Replication–Defective Human Adenovirus Recombinant Serves as a Highly Efficacious Vaccine Carrier," *Virology* vol. 219, 220–227.

Zheng, et al. (1994). "The E1 sequence of bovine adenovirus type 3 and complementation of human adenovirus type 5 E1A function in bovine cells," *Virus Research* vol. 31, 163–186.

Zoller, Mark and Smith, Michael. (1982). "Oligonucleotide–directed mutagenesis using M13–derived vectors: and efficient and general procedure for the production of point mutations in any fragment of DNA," *Nucleac Acids Research* vol. 10, No. 20, 6487–6500.

* cited by examiner

CATCATCAATAATATACCGCACACTTTATTGCCCCTTTTGTGGCGTGGTGATTGGCGGAGAGGGT
TGGGGGCGGCGGGCGGTGATTGGTGGAGAGGGGTGTGACGTAGCGTGGGAACGTGACGTCGCGTGG
GAAAATGACGTGTGATGACGTCCCGTGGGAACGGGTCAAAGTCCAAGGGGAAGGGGTGGAGCCCTG
GGGCGGTCCTCCGCGGGGCGGGGCCGAGCGGCGGAAATTCCCGCACAGGTGGAGAGTACCGCGGGA
TTTTGTGCCCTCTGGACCGGACCTTCGCCCTCCGGTGTGGCACTTCCGCACCACACGTCCGCGGCC
CGGTATTCCCCACCTGACGACGGTGACACCACTCACCTGAGCGGGGTGTCCTTCGCGCTGAGAGGT
CCGCGGCGGCCGCCCGAGATGACGTGTGTGGGTGTATTTTTCCCCTCAGTGTATATAGTCCGCGC
AGCGCCCGAGAGTCACTACTCTTGAGTCCGAAGGGAGTAGAGTTTTCTCTCAGCGGAACAGACCCT
CGACATGGCGAACAGACTTCACCTGGACTGGGACGGAAACCCCGAGGTGGTGCCGGTGCTGGAATG
GGACCCGGTGGATCTGCGCGACCCCTCTCCGGGGGATGAGGGCTTCTGTGAGCCGTGCTGGGAGAG
TCTGGTCGATGGACTGCCGGACGAGTGGCTGGACAGTGTGGACGAGGTGGAGGTGATTGTGACTGA
GGGGGGTGAGTCAGAGGACAGTGGTGGGAGTGCCGCTGGTGACTCAGGTGGCTCTCAGGGGGTCTT
TGAGATGGACCCCCCAGAAGAGGGGGACAGTAATGAGGAGGATATCAGCGCGGTGGCTGCGGAGGT
GCTGTCTGAACTGGCTGATGTGGTGTTTGAGGACCCACTTGCGCCACCCTCTCCGTTTGTGTTGGA
CTGCCCCGAGGTACCTGGTGTGAACTGCCGCTCTTGTGATTACCATCGCTTTCACTCCAAGGACCC
CAATCTGAAGTGCAGTCTGTGCTACATGAGGATGCATGCCTTTGCTGTCTATGGTGAGTGTTTTTG
GACATTTGTGGGATTATGTGGAAAAAAAGGAAAAAGTGCTTGTAAGAAATCTCATGTGCTATTTCC
CATTTTTTGTCTTTTTAGAAGCTGTTTCTCCAGCACCTCACAGGTCGGGTTCCCCGGGACTTGGAG
ACCTGCCAGGACGCAAGAGGAAGTACTGCTATGACTCATGCAGCGAACAACCTTTGGACCTGTCTA
TGAAGCGCCCCCGCGATTAATCATTAACCTCAATAAACAGCATGTGATGATGACTGATTGTCTGTG
TCTCTGCCTATATATACCCTTGTGGTTTGCAGGGAAGGGATGTGGTGACTGAGCTATTCCTCAGCA
TCATCATCGCTCTGCTTTTTTCTACTGCAGGCTATTTCTTGCTAGCTCGCTGTCCCTTTTCTTTTT
CTGTGGGCATGGACTATCAACTTCTGGCCAAGCTTACTAACGTGAACTACCTTAGGAAGGTGATAG
TACAGGGGTCTCAGAACTGCCCTTGGTGGAAAAAGATTTTTTCGGACAGGTTTATCAAGGTAGTAG
CAGAGGCCAGGAGGCAGTACGGGCAAGAGTTGATTGAGATTTTTGTGGAGGGTGAGAGGGGCTTTG
GTCCTGAGTTCCTGCGGGAAGGGGGACTGTACGAAGAGGCCGTTCTGAAAGAGTTGGATTTCAGCA
CCTTGGGACGCACCGTAGCTAGTGTGGCTCTGGTCTGCTTCATTTTTGAGAAGCTTCAGAAGCACA
GCGGGTGGACTGACGAGGGTATTTTAAGTCTTCTGGTGCCGCCACTATGTTCCCTGCTGGAGGCGC
GAATGATGGCGGAGCAGGTGCGGCAGGGGCTGTGCATCATCAGGATGCCGAGCGCGGAGCGGGAGA
TGCTGTTGCCCAGTGGGTCATCCGGCAGTGGCAGCGGGGCCGGGATGCGGGACCAGGTGGTGCCCA
AGCGCCCGCGGGAGCAGGAAGAGGAGGAGGAGGACGAGGATGGGATGGAAGCGAGCGGGCGCAGGC
TCGAAGGGCCGGATCTGGTTTAGATCGCCGCCGGCCCGGGGGAGCGGGTGGAGAGGGGAGCGGGGA
GGAGGCGGGGGGGTCTTCCATGGTTAGCTATCAGCAGGTGCTTTCTGAGTATCTGGAGAGTCCTCT
GGAGATGCATGAGCGCTACAGCTTTGAGCAGATTAGGCCCTATATGCTTCAGCCGGGGGATGATCT
GGGGGAGATGATAGCCCAGCACGCCAAGGTGGAGTTGCAGCCGGGCACGGTGTACGAGCTGAGGCG
CCCGATCACCATCCGCAGCATGTGTTACATCATCGGGAACGGGGCCAAGATCAAGATTCGGGGGAA
TTACACGGAGTACATCAACATAGAGCCGCGTAACCACATGTGTTCCATTGCGGGCATGTGGTCGGT
GACTATCACGGATGTGGTTTTTGATCGGGAGCTACCGGCCCGGGGTGGTCTGATTTTAGCCAACAC
GCACTTCATCCTGCACGGCTGCAACTTCCTGGGCTTTCTGGGCTCGGTAATAACGGCGAACGCCGG
GGGGGTGGTGCGGGGATGCTACTTTTTCGCCTGCTACAAGGCGCTGGACCACCGGGGGCGGCTGTG
GCTGACGGTGAACGAGAACACGTTTGAAAAGTGTGTGTACGCGGTGGTCTCTGCGGGGCGTTGCAG
GATCAAGTACAACTCCTCCCTGTCCACCTTCTGCTTCTTGCACATGAGCTATACGGGCAAGATAGT
GGGGAACAGCATCATGAGCCCTTACACGTTCAGCGACGACCCCTACGTGGACCTGGTGTGCTGCCA
GAGCGGGATGGTGATGCCCCTGAGCACGGTGCACATCGCTCCCTCGTCTCGCCTGCCCTACCCTGA
GTTCCGCAAGAATGTGCTCCTCCGCAGCACCATGTTTGTGGGCGGCCGCCTGGGCAGCTTCAGCCC
CAGCCGCTGCTCCTACAGCTACAGCTCCCTGGTGGTGGACGAGCAGTCCTACCGGGGTCTGAGTGT
GACCTGCTGCTTCGATCAGACCTGTGAGATGTACAAGCTGCTGCAGTGTACGGAGGCGGACGAGAT
GGAGACGGATACCTCTCAGCAGTACGCCTGCCTGTGCGGGGACAATCACCCCTGGCCGCAGGTGCG
GCAGATGAAAGTGACAGACGCGCTGCGGGCCCCCCGGTCCCTGGTGAGCTGCAACTGGGGGGAGTT
CAGCGATGACGATGACTGAGGATGAGTCACCCCCTCCCCTCCTCTTGCAGGTACGTGGCCCCGCCC
AGTGGGATGGGCTTTGGATGGGGGAGGGGTGTTCCCTATAAAAGGGGGATGGGGGTGGAGGCATGC
AGCCCCACGGGGAAGCTTGTGTGGAGGATGTCTTCCGAGGGTGAGATCCGGACCTGCTTCATTTCA

FIG._1-1

GCTCGTCTTCCCAGCTGGGCCGGCGTGCGTCAGGGAGTGGCCGGGACGAATGTGAACGGCGGAGTG
GTGGGCGCCCCTGCCCAGAGCGGGGTGCTGGCCTACTCCCGCTTCGTTCAGCAGCAACAGCAGCAG
CCGGGGACGGCGGCGACGGGGTCTGTGTTCCGGGCGGTGTTTCCATCGGTGGATCTGAGCGCGGAG
GTGGGCATGATGCGGCAGGCGCTGGCGGAGCTGCGGCAGCAGCTGCAGGAGCTGCGGGAGGTGGTG
GAGATACAGCTGCGGGCCACGGCCTCGGAGGCGGCCGAGGAGGAAGAGGAGGAGGAGATTGTGGTG
GACGAGGAGGTGGCGCCCGGCGCTGGAGCGAACACCATGGAAGAGGAGGAGGATGAGATGGTCCTG
ACGATGACTGTGGTGGGGGACCCTGAGCCTGCTGGAGTGGAAGCCCAGCCGCCACCACCACCCACC
CCGGAGAGCGACCCTGCGGTGCCTGCTACTACCACTACCCCGAAGCGGCTCAGCTACGGCGCGAGC
AAGAGGAGCGGTCCATGCGCGGAGGACAACTGACGCGGACTGTGGGGGGAAGAAGGGGGAGGAGGA
AAGAAGACCATGGAGACGGGTGTTTGTCTTTTTCCAGCCCAACTTTATTGAGAATAATAATAAAGC
TTATGGATGTTTGGAACGATAATAGCGTGTCCAGCGTTCTCTGTCTTGCAGGGTCTTGTGTATCTT
CTCGAGGCACCGGTAGACCTGGTGTTGGACGTTGAAATACATGGGCATGACTCCCTCGGCGGGGTG
CAGGTAAAGCCACTGGAGGGCTGGGTGCGGGGGGCAGGTGCAGTAGATGATCCAGTCATAGGCGTT
CTGGTTGCGGTGGTGGTTGAAAATGTCCTTGAGGAGCAGGCTGATGGCGGTGGGCAGACCCTTGGT
GTAGGCATTGATGAACCGGTTGACCTGGGCGGGCTGCATGAGGGGGGACATGATGTGGTACTTGGC
CTGGATCTTGAGGTTGGAGATGTTGCCGCTCTGGTCGCGGCGGGGGTTCATGTTGTGGAGGACGAC
GAGGACGGCGTAGCCGGTGCAGCGGGGGAAGCGGGCGTGCAGCTTGGAGGGGAAGGCGTGGAAGAA
CTTGGCGACCCCCTTGTGTCCGCCGAGGTCCTCCATGCACTCGTCGAGGACGATGGCGATGGGTCC
GCGGGCGGCGGCGCGGGCGAAGACGTTGCGTGAGTCAGTGACATCATAGTTGTGCTCCTGCATGAG
GTCCTGGTAGCTCATGCGGACAAAGTCTGGCATGAGGGTGGCGGTCTGGGGGATTAGGGTGTGGTC
CGGACCGCTGCGGTAGTTGCCCTCGCAGATCTGGGTCTCCCAGGCGACTACCTCCTGCGGGGGGAT
CATGTCCACCTGCGGGGTGATGAAGAAAACAGTCTCCGGCGGGGGGGAGAGGAGTTGGGAGGAGAT
GAGGTTGCGGAGCAGCTGGGACTTGCCGGAGCCGGTGGGACCGTAGATGACAGCGATGACTGGCTG
GACCTGGTAGTTGAGGGAGCGGCAGGTGCCAGCCGGGGTGAGGAAGGGCATGCAGGCGTTGAGGGT
GTCGCGCAGGTTGCGGTTCTCTTGGACGAGGTCCTGCAGGAGGTGTCGGCCTCCCAGGGAGAGGAG
GTGGGAGAGGGAGGCGAAGGCCTTGAGGGGCTTGAGGCCCTCGGCGTAGGGCATGTCCTGCAGGGC
CTGGTGGAGCACGCGCATGCGCTCCCAGAGCTCGGTTACATGTCCCACGGTATCGTCCTCCAGCAG
GTCTGGTTGTTTCTCGGGTTGGGGTTGCTGCGTGAGTACGGAACGAGGCGGTGGGCGTCGAGCGGG
TGGAGGGTCCGGTCCTTCCAGGGCCGGAGGGCCCGCGTGAGGGTGGTCTCGGTGACGGTGAAGGGG
GCGGTCTGGGGCTGCTCGGTGGCCAGGGTCCTCTTGAGGCTGAGGCGGCTGGTGCTGAAGGTGGCG
CTTCCGAGCTGCGCGTCGTTCAGGTAGCACTGGCGGAGGAGGTCATAGGAGAGGTGTTGGGTGGCA
TGGCCCTTGGCGCGGAGCTTGCCGGGGCCGCGGTGCCCGCAAGCATCGCAAACGGTGTCGCGCAGG
GCGTAGAGCTTGGGGGCGAGCAGGACCGTCTCGGAGCTGTGGGCGTCGCTGCGGCAGCGCTCGCAC
TGGGTCTCGCACTCGACCAGCCAGGTGAGCTGGGGGTTCTGGGGATCGAAGACGAGGGGGCCCCCG
TTCCGCTTGAGGCGGTGTTTACCTTTGGTCTCCATGAGCTCGCGTCCGGCGCGGGTGAGGAAGAGG
CTGTCGGTGTCCCCGTAGACGGAGCGCAGGGGCCGGTCGGCGATGGGGGTGCCGCGGTCGTCGGCG
TAGAGGATGAGGGCCCACTCGGAGATGAAGGCACGCGCCCAGGCGAGGACGAAGCTGGCGACCTGC
GAGGGGTAGCGGTCGTTGGGCACTAATGGCGAGGCCTGCTCGAGCGTGTGGAGACAGAGGTCCTCG
TCGTCCGCGTCCAGGAAGTGGATTGGTCGCCAGTGGTAGTCCACGTGACCGGCTTGCGGGTCGGGG
GGTATAAAAGGCGCGGGCCGGGGTGCGTGGCCGTCAGTTGCTTCGCAGGCCTCGTCACCGGAGTCC
GCGTCTCCGGCGTCTCGCGCTGCGGCTGCATCTGTGGTCCCGGAGTCTTCAGGTGGGTACGCTACG
ACAAAGTCCGGGGTGACCTCAGCGCTGAGGTTGTCTGTTTCTATGAAGGCGGAGGAGCGGACGGAG
AGGTCGCCGCGGGCGATGGCTTCGGTGGTGCGGGCGTCCATCTGGCTGGCGAAGACCACCTTCTTA
TTGTCGAGGCGTGTGGCGAAACTGCCGTAGAGGGCGTTGGAGAGAAGCTTGGCGATGCTGCGGAGC
GTTTGGTTTCTGTCCCGGTCGGCCTTTTCCTTGGCAGCGATGTTGAGCTGCACGTAGTCTCGGGCG
AGGCAGCGCCACTCGGGGAAGATGCTGTTGCGCTCGTCCGGCAGGAGGCGCACGGCCCAGCCACGG
TTGTGGAGGGTGACCACGTCCACGGAGGTGGCTACCTCGCCGCGGAGGGGCTCGTTGGTCCAGCAG
AGGCGGCCGCCCTTGCGGGAGCAGTAGGGGGGCAGGACGTCCAGCTGGTCCTCGTCGGGGGGGTCG
GCGTCGATGGTGAAGAGGGCGGGCAGGAGGTCGGGGTCGAAGTAGCTGAGGGGCTCGGGGCCGTCG
AGGCGGTCCTGCCAGCGGCGGGCGGCCAGGGCGCGGTCGAAGGGGTTGAGGGGTTGGCCGGCGGGG
AAGGGGTGGGTGAGGGCGCTGGCATACATGCCGCAGATGTCATAGACGTAGAGGGGCTCCCGCAGG
AGGCCGATGAAGTTGGGGTAGCAGCGGCCGCCGCGCAGGCTCTTCGCGGACGTAGTCATACAGCTC
GTGGGAGGGCGCGAGGAGGTTCGGCCGAGGTGCGGCGCCTGGGGCCGGCTGGCGCGGTAGAGGAGC
TGCTTGAAGATGGCGTGGGAGTTGGAGCTGATGGTGGGCCTCTGGAAGACATTGAAGGCGGCGTGG
GGAAGGCCGGCCTGCGTGTGGACGAAGGCGCGGTAGGACTCTTGCAGCTTGCGGACCAGACGGGCG
GTGACGACGACGTCCTGGGCGCAGTAGCGCAGGGTGGCCTGGACGATGTCGTAAGCGTCCCCCTGG

FIG._1-2

CTCTCCTTCTTCCACAGGTCCTTGTTGAGGAGGTACTCCTGATCGCTGTCCCAGTACTTGGCGTGT
GGGAAGCCGTCCTGATCGCGTAAGTAGTCCCCCGTGCGGTAGAACTCGTTCACGGCATCGTAGGGG
CAGTGTCCCTTGTCCACGGCCAGCTCGTAGGCCGCGGCGGCCTTGCGGAGGCTGGTGTGCGTGAGG
GCGAAGGTGTCCCGGACCATGAACTTGACGTACTGGTGCTGGGGGTCCTCGGGGGCCATGACGCCC
TCCTCCCAGTCCGCGTAGTCGCGGCGCGGGCGGAAGGCGGGGTTGGGCAGGTTGAAGCTGATGTCA
TTGAAGAGGATGCGGCCGTTGCGCGGCATGAAGGTGCGGGTGACCAGGAAGGAGGGGGGCACCTCG
CGGCGGTGGGCGAGCACCTGCGCGGCCAGGACGATCTCATCGAAGCCCGAGATGTTGTGGCCCACG
ATGTAGACCTCCAGGAAGAGGGGCGGCCCGCGCAGGCGGCGGCGCCGCAGCTGGGCATAGGCCAGG
GGGTCCTCGGGGTCGTCCGGCAGGCCGGGGCCCCGCTCCTGCGCCAGCTCGGCGAGGTCTGGGTTG
TGGGCCAGCAGGTGCTGCCAGAGGGTGTCGGTGAGGCGGGCCTGCAGGGCGTGCCGCAGGGCCTTG
AAGGCGCGGCCGATGGCGCGCTTCTGCGGGCAGAGCATGTAGAAGGTGTGGGCTCGGGTCTCCAGC
GCTGCAGGCGGGCTCTGGACGGCCACCACCTGCAGCGCGGCGTCCAGCAGCTCCTCGTCCCCCGAG
AGGTGGAAGACCAGCAGGAAGGGCACGAGCTGCTTTCCGAAGCGGCCGTGCCAGGTGTAGGTCTCC
AGGTCATAGGTGAGGAAGAGGCGGCGGGTGCCCTCGGGGGAGCCGATGGGGCGGAAGGCGATGGTC
TGCCACCAGTCGGCCGTCTGGCGCTGAACGTGGTGGAAGTAGAAGTCCCGGCGGCGCACGGAGCAG
GTGTGGGCGGTCTGGAAGATGCGGCCGCAGTGCTCGCACTTCTGGGCCTCCTGGATGCTCTTGATG
AGGTGGCAGCGGCCCTGGGTGAAGAGCAGGCGGAGGGGGAAGGGGAGGCGGGGCGGCGGGCCCTCG
GGCGGGGGGTCCCAGCGCACGTGGTGCAGGTGGTGTTGCTGGCGGGTGACCACCTGGACGAAGGTG
GGCCCGGCGGCGCGGGCCAGCTCCACCGCGGTCTGGGGGTAGCCTGCAGGAGGTCGGGGGGCGGG
CGCAGGAGGTGCAGCTGGAAGAGGTTGGCCAGGGCGCTGTCCCAGTGGCGGTGGTAGGTGATGCTC
CAGCTCTCCCCGTCCTGGGTGGTGCCCTGGAGGCGGAGGGTGGCGCGGCGCTCGAGCAGGAGCCCC
CGCGTGCCGGCCTCCGCGGCCTCGGCGGCGGCGGCCGGTCTCAGGCGGGCAGCTGGGCCAGGGGCA
CGGGCGCGTTGAGCTCGGGCAGCGGGAGGTGGTCGCGGCGCAGACGCGAGGCGTGGGCGATGACGC
GGCGGTTGATGTTCTGGATCTGCGGGTTCCCGGAGAAGACCACGGGCCCGGTGACTCGGAACCTGA
AAGAGAGTTCCACGGAATCAATGTCGGCATCGTGGGTGGCCACCTGGCGCAGGATCTCGGACACGT
CCCCGCTGTTTTCGCGGTAGGCGATGTCCTGCATGAACTGCTCGAGCTCGTCCTCGTCCAGGTCCC
CGTGGCCGGCGCGCTCCACGGTGGCGGCCAGGTCGACGGTGATGCGGTTCATGATGGCCACCAGGG
CGTTCTCTCCGTTCTCGTTCCACACGCGACTGTAGACCAGCTGGCCGTCGGCGTCCCGCGCGCGCA
TGACTACCTGGGCCAGGTTGAGCGCCACCAGGCGGTTGAAGGGCGCCTGCAGGCGCAGGGCGTGGT
GCAGGTAGTTGAGGGTGGTGGCGATGTGCTCGCAGAGGAAGAAGTTTATGACCCAGCGGCGCAGGG
TCAGCTCGTTGATGTCGCCCAGGTCCTCGAGGCGCTGCATGACCCGGTAGAACTCGGGGGCGAAGC
GAAAAAACTCGTGCTGGCGGGCCGAGACCGTGAGCTCCTCTTCCAGGGCGGCGATGGCCTCGGCCA
CCGCCTGCCGCACCTCCTCCTCTAAGGAGGGCGGGGGCGTGCTGGGTCCGGCCACCGCCGCCTCTT
CTTCCTCTTCTCCCTCCAGGGGTGGCATCTCCTCGTCTTCTTCTTCTGCTGCTGCTGCCTCCGCGG
GGACGGGGGGCGCAGGCCGGGGACGGCGCCGGCGCAAGGGCAGCCGGTCCACGAAGCGCTCGATGA
CCTCGCCCCGCATGCGGCGCATGGTCTCGGTGACGGCGCGGCCGCCCTCCCGGGGCCGCAGCTCGA
AGGCGCCCCCGCGCAGCGCGGTGCCGCTGCAGAGGGGCAGGCTGAGCGCACTGATGATGCAGCGTG
TCAACTCTCTCGTAGGTACCTCCTGCTGTTGCAGCGCTTCGGCAAACTCGCGCACCTGCTCTTCGG
ACCCGGCGAAGCGTTCGACGAAGGCGTCTAGCCAGCAACAGTCGCAAGGTAAGTTGAGCGCGGTGT
GCGTCGGGAGCCGGAGGTGCCGGCTGACGAGGAAGTGAAAGTAGGCCGTCTTGAGCTGCCGGATGG
CGCGCAGGAGGGTGAGGTCTTTGCGGCCGGCGCGCTGCAGGCGGATGCGGTCGGCCATGCCCCAGG
CCTCCTGCTGGCAGCGGCCGATGTCCTTGAGCTGCTCCTGCAGCAGATGTGCCACGGGCACGTCCC
GGTCGGCGTCCAGGTGGGTGCGACCGTAGCCCCGCAGGGGGCGCAGCAGCGCCAGGTCGGCCACCA
CGCGCTCGGCCAGGATGGCCTGCTGCATGCGCTGCAGGGAGTCTGAGAAGTCATCCAGGTCCAGGA
ACCGGTGGTAGGCGCCCGTGTTGATGGTGTAGGAGCAGTTGCCCAGCACGGACCAGTTGACCACCT
GGTAGTGGGGCTGGATGACCTCGGTGTAGCGCAGTCGACTGTAGGCGCGCGTGTCAAAGATGTAAT
CGTTGCAGAGGCGCAGCAGGTGCTGGTAGCCCACGAGCAGGTGGGGCGGAGGGTAGAGGTAGAGGG
GCCAGTGTTCCGTGGCCGGTTGGCGGGGGGAGAGGTTCATGAGCATGAGGCGGTGGTAGCGGTAGA
TGAAGCGGGACATCCAGGCGATGCCGACGGCGGAGACGGAGGCGCGGGTCCACTGGTGGGCGCGGT
TCCAAATGTTGCGCACCGGGCGGAAGAGCTCCACGGTGTAAATGGATTGCCCCGTGAGGCGGGCGC
AGTCGAGGGCGCTCTGTCAAAAAGAACCGGGTGTGGTTGGTTGGTGTGTGGTAGCGATCTATCTTT
CTTTGTGATCTTGGTAGTGAAGCCTGCCAGGCTCCAGCAGGGGGCGTCCGCCGTCTTTCCTTCCTT
CCCTATCTGGAGGTGTGTCTCTGTTCTCTTTTTATTTCATGTAGCCATGCATCCCGTTCTGCGGC
AGATGAAGCCGCCGGCCGGCGCCCTGGGCGCGGAGGGGGCGACGCGCTCTCGGTCGCCCTCGCCGT
CGCTGACGCGGCCGCGCGAGGAGGGGGAGGGCCTGGCGCGGCTGTCGGGCGCGGCGGCCCCCGAGC
GGCACCCACGGGTGCAGCTCAAGCGAGAGGCCATGGAGGCCTATGTGCCGAGGCAGAATGCGTTCC

*FIG._1-3*

```
GCGAGCGACCGGGGGAGGAGGGGGAGGAGATGAGGGACCTGCGGTTCCGCGCGGGGCGGGAGATGC
AGCTGGACCGGGAGCGAGTGCTCCAGCCCGAGGACTTTGAGGGGCGCGTGGAGGAGGCGGGGGGAG
TGAGCGCGGCGCGGGCCCACATGAGCGCGGCCAGCCTGGCCCAGGCCTACGAGCAGACGGTACGCG
AGGAGGTCAACTTCCAAAAGACCTTCAACAACAACGTGCGCACCCTGGTGAGCCGGGACGAGGTGA
CCATGGGACTGATGCACCTGTGGGACTTTGTGGAGGCCTTCCTGCAGCACCCCCGGTCCCGCGCGC
TGACCGCGCAGCTGCTGCTGATCGCGCAGCACTGCCGGGACGAGGGCATGGTGAAGGAGGCGCTGC
TGAGCCTGGGCGCGCCCGAGAGCCGCTGGCTGGTGGACCTGGTGAACCTGCTCCAGACCATTGTGG
TGCAGGAGCGGTCCATGAGCCTGAGCGAGAAGGTGGCGGCCATCAACTACTCGGTGGCGACCCTGG
CCAAGCACTACGCGCGCAAGATCTCCACCTTCTACATGCGCGCGGTGGTGAAGCTGCTGGTGCTGG
CCGACAACCTGGGCATGTACCGCAACAAGCGGCTGGAGCGCGTGGTCAGCACCTCGCGGCGGCGCG
AGCTCAATGACAAGGAAGCTCATGTTTGGCCTCCGCCGGGCGCTGGCCGGGGAGGGCGAGGAGGAC
CTGGAGGAGGAGGAGGACCTGGAGGAGGCGGAGGAGGAGGAGCTGGAAAGAGGAGGAGTTCGGTCC
CCGGGGACCGCGGCGCGTGAGGTGGCAGTCCCCGCTGACTGCGAGCGATGAGGGTGATGTGTACTG
ATGGCAACCATCCCCCTTTTTAACAACAACAGCAGCATGGCGGCGAGCTCTGAAGCTGGGGCGGCG
GCGGCGGGGGTGAGCGCGGCCTCCCTGGCGCCCGAGCGGGCGACGCGGATGCAGGCGCTGCCCTCC
CTGGACGAGCCTTGGGAGCAGGCTCTGCGGCGCATCATGGCGCTGACGGCCGACGGGTCTCGGCGC
TTCGCGAGCCAGCCCCTGGCCAACCGCATCGGGGCCATCCTGGAGGCGGTGGTGCCTCCGCGCACG
AACCCGACGCACGAGAAGGTGCTGACCGTGGTGAACGCGCTGCTGGAGACCTCGGCCATCCGCCCG
GACGAGGCCGGCATGGTGTACGATGCGCTGCTGGAGCGGGTCTCCCGCTACAACAGCGGCAACGTG
CAGACCAACCTGGACCGGCTGTCCCAGGACGTGCGGCAGGTGATCGCCCAGCGCGAGCGCTCGAGC
GCCAACAACCTGGGCAGCCTGGCCGCGCTGAATGCCTTCATCGCCTCGCTGCCCGCAACGGTGGAG
CGGGGCCAGGAGAGCTACCTGGGGTTCCTCAGCGCGCTGCGGCTGCTGGTGAGCGAGGTGCCGCAG
ACGGAGGTGTTCCGCTCGGGGCCGCACACCTTCCTGCAGGCGGCGCGGAACGGTTCCAAGACGGTG
AACCTCAACCAGGCCATGGAGAACCTGCGGCCCCTGTGGGGGCTGCAGGCCCCCGCTGGGGAGCGC
GGGCACGTGTCCTCCCTGCTGACGCCCAACACCCGGCTGCTGCTGCTCCTGGTGGCTCCCTTCGCG
GAGGAGATGAACGTCAGCCGGAGCTCCTACATTGGGCACCTGCTGACACTCTACCGCGAGACGCTG
GCCAACTTGCATGTGGACGAGCGCACGTACCAGGAGATCACCAGCGTCAGCCGGGCGTTGGGCGAC
GAGGACGACGCGGCGCGGCTGCAGGCCACCCTCAACTTCTTCCTGACCAACCGGCAGCGGCGGCTG
CCGGCGGCGTATGCCCTGACCGCCGAGGAGGAGCGCATCCTGCGCTACGTGCAGCAGGCCGTGAGC
CTGTACCTGATGCAGGACGGGGCGACGGCCACGGGCGCCCTGGACGAGGCCAGCCGCAACCTGGAG
CCCAGCTTCTACGCGGCGCACCGGGACTTCATCAACCGCCTGATGGACTACTTCCATCGCGCGGCC
GCGGTGGCGCCCAACTACTTTATGAATGCCGTCCTGAACCCCCGCTGGCTGCCCTCGGAGGGCTTC
TTCACCGGCGTGTATGACTTCCCGGAGCAGGACGAGGGGGAGGAGCGGCCCTGGGACGCCTTTGAC
AGCGACGAGGAGGGCCGCCTCATGCTGCGGTCCGCAGCCTCCTCAGAGCCCTCCTCCTCCTTCACC
CCCCTGCCCCTGACCGAGGAGCCGCCCTCGCGGCCCTCCACCCCGGCCCTCTCGCGCGTCCCGTCC
CGGGCATCCTCCCTGCTCTCTCTGGCCTCTCTGGGAAAGCGGGAGGGAGGGGACTCGCTCGCCTAC
TCGCCGGCCACGCCCACCTATGGCTCTCGCTGGGGCTCGCGCCGCTCCAGCCTGGCCAGCGGCGCC
GACAGCCTGGAGTGGGACGCGCTGCTGGCCCCTCCCAAGGATGTGAACGAGCACCCAGGCGCCGCC
GCCGGCCGCCGCCGCCGCGCCTCCCGCTCCTCCCTGGAGGAGGACATCGACGCCATCAGCAGCCGG
CTGTTCACCTGGCGCACGCGCGCCCAGGAGATGGGCCTGCCCGTGGCCAGCTTCTCCCGCCGCCAC
CAGCCGCGCCCCGGGGCCCTCGAAGACGACGAGGAGGAGGAAGACTGGCGCCAGGACCGGTTCTTT
CGCTTCGAAGCGCCCGAGGAAAACCCCTTCCGCCACATCGCCCCCAAGGGGCTGTAATGCAAAAAA
GCAAAATAAAAAACCCCTCCCGGTCCAACTCACCACGGCCATGGTTGTCCTTGTGTGCCCGTCAGA
TGAGGAGGATGATGCCAGCAGCGCCGCCGCAGGGAGCGTCGCCTCCGCCGTCCTACGAGAGTGTGG
TGGGGTCTTCGCTCACGGAGCCTCTTTATGTGCCGCCGCGGTACCTGGGCCCCACCGAGGGGCGGA
ACAGCATCCGTTATTCACAGCTCCCGCCGCTCTACGATACCACAAAGATCTATCTGATCGATAACA
AGTCGGCGGATATCGCCAGTCTGAACTACCAAAACAACCACAGTGACTTTCTCACCAGCGTGGTGC
AGAACAGCGACTTCACGCCCATGGAGGCGAGCACGCAGACCATCAACCTGGATGAGCGCTCGCGCT
GGGGCGGGGAGTTTAAGAGCATTCTGACCACCAACATCCCCAACGTGACCCAGTACATGTTCAGCA
ACAGCTTCCGGGTGCGCCTGATGAGCGCGCGCGATAAAGAGACAAATGCCCCCACCTACGAGTGGT
TCACCCTGACCCTGCCCGAGGGCAACTTCTCGGACATCGCGGTCATCGACCTGATGAACAACGCGA
TCGTGGAGAACTACCTGGCGGTGGGGCGGCAGCAGGGGGTCAAGGAGGAGGACATCGGGGTGAAGA
TCGACACGCGCAACTTCCGCCTGGGCTATGACCCGGAGACCAAGCTGGTCATGCCCGGCAGCTACA
CCAACATGGCCTTTCACCCCGACGTGGTGCTGGCACCGGGCTGCGCCATCGACTTCACCTTCTCCC
GCCTAAACAACCTGCTGGGCATCCGCAAGCGCTACCCCTACCAGGAGGGCTTCATGCTGACCTACG
AGGACCTGGCGGGGGGCAACATCCCCGCGCTGCTGGACCTCACCACCTATGATCAGGAGAACTCCA
```

FIG._1-4

GCACCATCAAGCCCCTGAAGCAGGACAGCAAGGGTCGCAGCTACCACGTGGGCGAGGACCCCGAGG
CGGGGGACACCTTCACCTACTACCGCAGCTGGTACCTGGCCTACAACTACGGGGACCCGGCCACGG
GCACCGCCTCCCAGACGCTGCTGGTCTCCCCGGACGTAACCTGCGGAGTGGAGCAGGTCTACTGGA
GCCTGCCGGACCTGATGCAGGACCCGGTGACCTTCCGGCCCAGCCAGACGCCGAGCAACTACCCGG
TGGTAGCCACGGAGCTACTGCCGCTGCGCTCCCGGGCCTTCTACAACACCCAGGCCGTGTACTCCC
AGCTCCTGCAGCAGGCCACCAACAACACCCTGGTCTTTAACCGCTTCCCGGAGAACCAGATCCTCC
TGCGCCCGCCAGAGTCCACCATCACCTCCATCAGCGAGAACGTGCCCTCGCTGACGGACCACGGCA
CGCTGCCGCTGCGTAACAGCATCCCCGGGGTGCAGCGGGTAACCGTCACCGACGCGCGGCGCCGCG
TGTGTCCCTATGTGTACAAGAGTCTCGGGGTGGTGACCCCGAGGGTGCTCAGCAGCCGAACCTTCT
AACCGACAGCCCTACCCGTCACAGGGGAGACAGAGAAAAGACAGCCAGCCCCGCCATGGCCATCCT
CGTCTCGCCCAGCAACAACTTTGGCTGGGGACTGGGCCTGCGCTCCATGTACGGGGGCGCCCGCCG
CCTGTCCCCGGATCACCCCGTGATCGTCCGACGCCACTACCGGGCCAACTGGGCCAGTCTGAAGGG
ACGCGTGGCCCCCAGCACCATAGCGACAACGGATGACCCTGTGGCCGACGTGGTCAACGCGATCGC
CGGCGCCACCCGCCGCCGGCGCCGCCATCGTCGACGTCGGAGGGCCGCGCGCGTCTCCTCCGTGGC
CGTCACCGGGGACCCGGTGGCCGATGTGGTCAACGCGGTGGAGGCGGTAGCCCGGCGCCGCCGCGC
GCGGCGCCGTTCTTCGCGCATGCAGACCACGGGGGACCCCGTGGCGGATGTGGTGGCGGCGGTGGA
AGCGGTGGCGCGCCGGAGGCGGAGCACCCGGCGGCGGCGCAGGCGCTCCGCGCCGGCCATCCTGGG
GGTGCGCCGCAGCCGCCGCCTCCGCAAACGCACCTCGTCCTGAGATTTTTGTGTTTTGTTTTTTCT
GCCTCCCGTGGGTGAACAAGTCCATCCATCCATCCAACATCCGTGGCTGCTGTGTCTTTGTCTTTT
CTTTGCGTTGCGCCCCAGTTGAGCCGGCACCGACGCGCTCGGCCATGGCCATCTCGCGCCGCGTGA
AAAAGGAGCTGCTGCAGGCGTTGGCGCCCGAGGTGTACGGGGCGCCTAAGAAGGAGGAGAAGGACG
TCAAAGAGGAGTCCAAAGCTGACCTTAAACCGCTGAAGAAGCGGCGCAAGGCCAAGCGGGGGTTGA
GCGACAGCGACGAGGTGCTGGTGCTGGGCACGCGCCCCAGGCGCCGCTGGACGGGGCGGCGCGTGC
GCGCCCACCTACCGCCCGGTGCCAGCCTCGCCTACGTCCCGGGTCTTCGGAGGTCGAGCGCCACCA
AGCGCTCTGCGGACGAGTTGTATGCGGACACGGACATCCTGCAGCAGGCGTCCCAGCGCCTGAACG
AATTTGCTTATGGCAAGAGAGCCCGGCGGCAGCGGCGGGCCCGCCCCTCGCCGACCCCCGCGTCCC
GCGGCCGGACCACCAAGCGCTCTTATGACGAGGTCGTGGCAGACAGTGACATCCTGCAGCAACTTG
GATCCGGGGACCGCTCCAATGAGTTCTCCTATGGCAAGCGGTCGCTGCTGGGGGAGTCAGGAGACA
CCGTCCCGGCTGTGGCCGTCCCGCTGGAGGAAGGCAGGAACCACACACCCAGCCTGCAGCCGCTCA
CCGAGCCCATGCCCCTGGTGTCCCCTCGCACGGCCGTCAAGCGCCGGGCGCCCGCCGACGAGCCCA
CCGCCTCACTGGTCCCCACCGTGCAGGTCCTGGCCCCCAAGCGTCGTCTGCAGGAGGTGGTGGTGG
AGCCGCCCGCTCCAGCACCCACGCCGCCCCTAGCCCCGCGGCGGTCCAGCCGGCGCATCATTCTGG
CTCCGCGCCGGGCGGGCCGGCCCCAGGCCGTCGTGGCGCCGCAGCTCAGCGCGGCCGCGGCGCTGG
AGCGGGCGGCGGCCGCCGTGCCCCTGCCACCGGACACGGAGGACGACCTGGTGGAGATGGCAGAGG
CTGTCGCCGCGCCCGAGGTGCTGCCCAGCCTCCCCGTCTCCATCATGCCGCCCACCGCCACGGAGG
TGGCCCTGCCCGTACAGACCCCACTGCCGCCCGTGGCGGTGGCCAAGAGCTCCCTGACCCCCGGCC
TCCGCGCGCTGATGGGCACCGAGCGGGTGCCGGTTCCAGTCCTGGAGGCGCCCCTGGTGGCCATGC
CCGTGCTCCGGGCCACCACCGCCCGTGCCGAGCCCCCGCGCCGCGTGCCCCGCAGGGCCGTGCGGG
ACATCCCGGCCAGGCAGCCCCGCACGGTATCCCTGCCCGTGCTCACGGAGCCCGGCCCGGCCACCG
CGGTCGCCTCCGTGCGCGCGGCAGCCCAAGTCCTGCAGGCGCCCCCCGCCCGACCGGCCACCGTCT
CCGTGGGGGTGGGCACCGAGCCGGTGGTGCAGTCCATCACGGTCAAGCGGTCAAAGCGCCTGACCA
AGCACCATCGGGGTGCAGACCATCGACGTCACCGTGCCCACCGTCCGCACTGTCAGCGTGGGCACC
AACACGCCCCGGCTGAGGAGCGCCTCGGTGGGCGTCCAGACCGCTCCCGAGACCCGCTCCCAGGGG
GTGCAGGTGGCTTTCCAACCAGCGTGCTAGCCCACCGCACACCCAGGCAGGTGCGGCTGACGGCGG
TGGTGCCCCCCACCCCGCGCGCCCCGGTGGTTCCGGTGGCCCGGCGCCCGCGGCGGTTCCGGTGCC
TCCCCCAGCCCCTCCAGCCCCGCGCGCGCCGCGTGCGCCTCGCGCCCCCAGAGCGCCTCGGCGTCG
CCGCCGTACCCCGGTGGCGGTGGCAGCGCCGCCCGCCCGCAGCGGCGGTCCCCCGCCCTCGGCTGC
CGAGGCGGCCCATCGTGCTGCCCGGGGTGCGCTATCATCCCAGTCAGGCCATGGCTCCCACCGCCC
AACGCGTCATCTGGCGTTGATTTATTTTTGGAGACCTGACTGTGTTGTGTTCCTTAAATTTTTTAT
CCTCCTCCTCCTCTGCTGAAGCCAGACGATGCTGACCTACCGGTTGCGGCTGCCCGTGCGGATGCG
GAGACCGAGACTCCGCGGTGGGTTCCGCGTGGCGCCTCGGCGCAGCGGCGGCAGGCGGCGGTACCG
CCGGGGGCCGATGAGGGGTGGCATCCTGCCGGCGCTGGTGCCCATCATCGCGGCATCCATCTGGGC
CATCCCCGGCATCGCCTCGGTGGCGATGAGTGCTAGACAACGCAATTAACGGCGCTGCTGTGTATG
TGTGTCTTCCATGTGCCTTCCTTCCTTCGTTCCCAACGGAACAGCAGCACCGTCTCCATGGAGGAC
CTAAGCTTTTCCGCGTTGGCTCCACGCTTTGGCACGCGGCCGGTCATGGGCACTTGGAGCGAAATC
GGCACGAGTCAGATGAACGGCGGCGCGCTCAGCTGGAGCAATATCTGGAGCGGGCTGAAGAGCTTT

FIG._1-5

GGTAGTTCTCTGGCCTCCACGGCCAACAAGGCCTGGAACAGCGGGACGGTGACGAGCGTGCGCAAC
AAGTTGAAGGATGCCGACGTGCAGGGGAAGATAGGTGAGGTCATTGCCTCCGGGGTCCACGGTGCC
CTGGACGTGGCCAACCAGGCCGTCTCCCACGCCGTGGACCGCCGGTGCAACAGCAGCAGCTGCGGC
AGCAGCAGCTCCTCCGCCAGCAGCAGCAACAGATGGGCCTCGTGGAACCCTCCTATGAGATGGAGA
CAGACGAGCTGCCTCCTCCCCCCGAGGACCTCTTGCCTCCTCCTCCTCCTCCGCCGCCTGCCTCGG
CCACTCCCGCGCGCCAATCCCGCGGGACGTCCCGCCAAGCGCCCGCCGCCGCCCAGGAGATCATCA
TCCGCTCCGACGAGCCCCCTCCCTATGAAGAGCTGTATCCCGACAAGGCCGGGATCCCCGCCACCT
TGGAGCTGCGTCCCGAGACCAAACTGCCCGCCGTGGCCCACAATAAGATGCGCCCCCCGCCGCCGC
TCACCACCACCACCTCCTCCGCTGCCGCCGCCGCCCCCGCCCCGGCCCCCGCGGCTCCTGTGCGTC
GGCGTCCGGCCGCGGCTCCGGCCGCGGCTCCGGCGAGTTCCAAAGGCCCCCCAGGTGGGGGTCCGC
GCGCGCGGGTGGCAAAACAAACTCAACACCATTGTGGGACTGGGTGTCCGCACATGCAAGCGCCGT
CGTTGTTACTGAGAGAGACAGCATGGAGAAACAACAATGTCTGGATTCAAATAAAGACACGCCTAT
TCTTCCACGGTGCTCCGCGCTGTGTTATTTCAACGGGCTGTTTCCTTTTGCATCTCTGTGCCATC
GCGCCACGGGGAATTCCGCAGGATGGCGACGCCGTCGATGATGCCGCAGTGGTCCTATATGCACAT
CTCCGGGCAGGACGCGTCCGAGTACCTGTCTCCCGGGCTGGTGCAGTTCTCCCAGGCGACGGAGAC
CTACTTTAACCTGAACAACAAGTTTAGGAACCCCACCGTCGCGCCCACCCACGATGTGACGACGGA
GCGCTCGCAGCGGCTGCAGCTGCGCTTCGTCCCCGTGGACAAGGAGGACACTCAGTACACATACAA
GACCCGCTTCCAGCTGGCGGTGGGCGACAACCGCGTGTTGGACATGGCGAGCACCTTCTTTGACAT
CCGGGGAACGCTGGACCGGGGACCCTCCTTCAAACCGTACTCGGGCACCGCGTACAACATCATGGC
TCCCAAGAGCGCTCCCAACAACTGTCAATATCTAGACCCTAAAGGTGAAACTGAGGCTGGCAAAGT
TAATACCATTGCTCAAGCAAGTTTTGTGGGTCCTATTGATGAAACCACGGGAGACATTAAAATTAC
AGAAGAAGAAGACGAAGAGACCACCATCGATCCTTTGTATGAGCCCCAACCCCAGCTTGGTCCAAG
CTCGTGGTCAGACAATATACCTTCTGCGACTAGCGGAGCTGGAAGAGTTCTCAAACAGACCACACC
GCGTCAACCTTGTTACGGTTCTTATGCCTCTCCGACAAATATTCACGGTGGGCAAACGAAGGATGA
CAAGGTTACACCATTGTACTTTACAAACAATCCCGCCACCGAAGCCGAAGCACTCGAAGAAAATGG
ATTAAAGCCAAATGTCACCCTATACTCAGAGGATGTTGACCTAAAAGCACCAGATACTCATCTGGT
CTATGCTGTGAATCAAACCCAGGAATTCGCTCAATATGGACTTGGACAACAGGCCGCTCCAAACAG
GGCCAATTACATCGGCTTCAGGGACAACTTTATCGGGCTGTTGTACTACAACAGCAATGGCAACCA
GGGCATGCTAGCCGGTCAGGCCTCTCAGCTCAACGCGGTGGTCGACCTGCAGGACAGGAATCACCG
AACTAGCTACCAGCTCTTCCTCGATAGCCTCTATGACAGGTCGAGGTACTTTAGCCTGTGGAACCA
GGCCATCGATTCTTATGACAAGGATGTGCGTGTGCTGGAAAACAATGGCGTGGAGGACGAGATGCC
CAACTTTTGCTTTCCCATCGGCGCCATCGAGACCAACATGACATTTACACAGCTCAAAAAGAGTGA
GAATGGTGGCTCAAGAGCCACAACCTGGACAAAGGAGAATGGGGATGATGGCGGAAACGGAGCGGA
GCACTACCTGGGCATCGGCAACCTCAACGCCATGGAGATCAATCTCACGGCCAACCTCTGGCGCAG
CTTCCTCTACAGCAACGTGGCGCTGTACCTGCCTGACAAGTACAAGTTTTCCCCGCCCAACGTCCC
CATCGACCCCAACACGCACTCCTATGACTACATCAACAAGCGCCTGCCCCTCAACAACCTCATTGA
TACCTTTGTCAACATCGGGGCGCGCTGGTCCCCGGATGTCATGGACAACGTCAACCCCTTCAACCA
CCACCGCAACTACGGCCTGCGCTACCGCTCCCAGCTCCTGGGCAACGGCCGCTACTGCAAGTTCCA
CATCCAGGTGCCGCAAAAGTTCTTTGCCCTCAAGAGCCTGCTGCTCCTGCCGGGGGCGACCTACAC
CTACGAGTGGTCCTTCCGCAAGGACGTCAACATGATCCTCCAGTCCACGCTGGGCAACGACCTCCG
CGCGGACGGGGCCAAAATCAACATCGAGAGCGTCAACCTCTACGCCAGCTTCTTTCCCATGGCCCA
CAACACCGCCTCCACCCTGGAGGCCATGCTGCGCAACGACACCAACAACCAAACCTTTATTGACTT
CCTCTCCTCCGCCAACATGCTCTACCCCATCCCGGCCAACGTCACCAACCTGCCCATCTCCATTCC
CAGCCGCAACTGGGCCGCCTTCCGCGGCTGGAGCTTCACGCGGCTGAAGCACAACGAGACCCCCGC
CCTGGGCTCGCCCTTCGACCCCTACTTTACCTACTCGGGCTCCATCCCCTACCTGGACGGGACCTT
CTACCTGGGCCACACCTTCCGCCGCATCAGCATCCAGTTCGACTCCTCCGTGGCCTGGCCGGGCAA
TGACCGCCTGCTCACTCCCAACGAGTTCGAGGTCAAGCGCACCGTGGACGGGGAGGGCTACACGGT
GGCCCAGACCAACATGACCAAAGACTGGTTCCTGGTGCAGATGCTCGCCCACTACAACATCGGCTA
CCAGGGATACCACCTGCCAGAGGGCTACCGCGACCGCACCTACTCCTTCCTGCGCAACTTTGAGCC
CATGTGCCGCCAGGTGCCCGACTACGCCAACCACAAAGATGAGTACCTGGAGGTGCCCACCACCAA
CCAGTTCAACAGCAGCGGCTTTGTATCCGCGGCCTTCACCGCCGGCATGCGCGAGGGGCACCCATA
CCCCGCCAACTGGCCCTACCCGCTCATCGGCGAAGACGCCGTGCAGACCGTGACCCAGCGCAAGTT
CCTCTGCGACCGCACGCTCTGGCGCATCCCCTTCTCCTCCAACTTCATGTCCATGGGCACCCTCAC
CGACCTGGGCCAGAACCTCCTCTACGCCAACTCGGCCCACGCCCTCGACATGACCTTCGAGGTCGA
CGCCATGGATGAACCCACCCTCTTGTATGTTCTGTTCGAGGTCTTTGACGTCTGCGGCGTGCACCA
GCCGCACCGAGGCGTCATCGAGGCCGTCTACCTGCGCACGCCCTTCTCCGCCGGGAACGCCACCAC

FIG._1-6

CTAAGGCGGAGCCGCGCAGGCATGGGCAGCACCGAGGACGAGCTCCGAGCCATGGCGCGCGACCTC
CAGCTGCCCCGCTTCCTGGGCACCTTTGACAAGTCCTTCCCGGGCTTCTTGCAAGAGTCCCAGCGC
TGCTGCGCCATCGTCAACACGGCCGCCCGCCACACCGGAGGCCGCCACTGGCTGGCCGTCGCCTGG
GAGCCCGCCTCGCGCACCTTCTACTTCTTTGACCCCTTCGGCTTCTCCGACCGGGAGCTCGCCCAG
GTCTATGACTTTGAGTACCAGCGCCTGCTGCGCAAGAGCGCCATCCAGAGCACCCCGGACCGCTGC
CTCACGCTCGTCAAGAGCACCCAGAGCGTGCAGGGACCGCACAGCGCCGCCTGCGGACTCTTCTGC
CTCCTCTTCCTCGCCGCCTTTGCCCGCTACCCCGACAGCCCCATGGCCTACAATCCCGTCATGGAC
CTGGTGGAGGGCGTGGACAACGAGCGGCTCTTCGACGCCGACGTCCAGCCCATCTTCCGCGCCAAC
CAGGAGGCCTGCTACGCGTTCCTCGCTCGCCACTCCGCCTACTTCCGCGCCCACCGCCACGCCATC
ATGGAACAGACACACCTGCACAAAGCGCTCGATATGCAATAAAGGCTTTTTATTGTAAGTCAAAAA
GGCCTCTTTTATCCTCCGTCGCCTGGGGGTGTATGTAGATGGGGGGACTAGGTGAACCCGGACCCG
CCGTCGGCTCCCCTCCATCCCCTCTTCTCTCAAAACAGGCTCTCATCGTCGTCCTCCGTTCCCACG
GGGAAGATGGTGTTCTGCACCTGGAACTGGGGCCCCCACTTGAACTCGGGCACCGTCAGTGGAGGC
CGCGTCTGCATCAGGGCGGCCCACATCTGTTTGGTCAGCTGCAGGGCCAGCATCACATCGGGGGCG
CTGATCTTGAAATCACAATTCTTCTGGGGGTTGCCGCGCGACCCGCGGTACACCGGGTTGTAGCAC
TGGAACACCAGCACCGCGGGGTGGGTCACGCTGGCCAGAATCTTGGGGTCTTCCACCAGCTGGGGG
TTCAGCGCCGCCGACCCGCTCAGCGCGAAGGGGGTGATCTTGCAGGTCTGCCGGCCCAGCAGGGGC
ACCTGGCGGCAGCCCCAGCCGCAGTCGCACACCAGCGGCATCAGCAGGTGCGTCTCCGCGTTGCCC
ATCCGGGGGTAGCAGGCCTTCTGGAAAGCCTTGAGCTGCTCGAAGGCCTGCTGCGCCTTGGAGCCC
TCCGAGTAGAAGAGGCCGCAGGACCGCGCCGAGAAGGTGTTGGGGGCCGACCCCACGTCGTGGCTG
CAACACATGGCCCCGTCGTTGCGCAGCTGCACCACGTTGCGGCCCCAGCGGTTGGTGGTGATCTTG
GCGCGCTCGGGGGTCTCGCGCAGGGCGCGCTGCCCGTTCTCGCTGTTGAGATCCATCTCCACCAGC
TGCTCCTTGTTGATCATGGGCAGCCCGTGCAGGCAGTGCAGCCCCTCCGAGCCGCTGCGGTGCTGC
CAGATCACGCACCCGCAGGGGTTCCACTCGGGCGTCTTCAGACCCGCCGCCTTCACCACAAAGTCC
AGCAGGAAGCGGGCCATCACTGTCAGCAGGCTCTTTTGCGTGCTGAAGGTCAGCTGGCAGCTGATC
TTGCGCTCGTTCAGCCAGGCTTGGGCCCCGCGCCGGAAGCACTCCAGGGTGCTGCCGTCCGGCAGC
AGCGTCAGGCCCTTGACATCCACCTTCAGGGGGACCAGCATCTGCACAGCCAGATCCATGGCCCGC
TGCCACTTCTGCTCCTGAGCATCCAGCTGCAGCAGCGGCCGGGCCACCGCCGGGCTCGGGGTCACC
GGGCGCGGGGGGCGGGCCCCCTCCTCTTCCTCCCCATCTTCGCCCTTCCTCCTCGCGGGCCGCGCC
GTCGCCGCTGCCGTCTCTTCAGCCTCGTCCTCCTCCTCCTCGCTGACCAGGGGCTTGGCACGCGCG
CGCTTCCGCCGCTCCTGCACGGGCGGAGAGGCCGCGCGCTTGCGGCCTCCCCCGCGCCGGCTGGGG
GTCGCGACAGGAGCGTCGTCCACAATCAGCACCCCCTCTTCCCCGCTGTCATAGTCAGACACGTCC
GAATAGCGGCGACTCATTTTGCTTCCCCTAGATGGAAGACCAGCACAGCGCAGCCAGTGAGCTGGG
GTCCTCCGCGGCCCCGACCCTTCCGCCGCCACCACCGCCGCCACCTCCGCCCACGTCACCGCCACC
TTCACTGCAGCAGCGGCAGCAGGAGCCCACCGAAACCGATGACGCGGAGGACACCTGCTCCTCGTC
CTCCTCGTCCTCCGCCTCCAGCGAGTGCTTCGTCTCGCCGCTGGAAGACACGAGCTCCGAGGACTC
GGCGGACACGGTGCTCCCCTCCGAGCCCCGCCGGGACGAGGAGGAGCAGGAGGAGGACTCGCCCGA
CCGCTACATGGACGCGGACGTGCTGCAGCGCCACCTGCTGCGCCAGAGTACCATCCTGCGCCAGGT
CCTGCAGGAGGCCGCCCCCGGCGCAGCCGCGGAGGCCGCCGAGGCGCCCTCGGTGGCGGAGCTCAG
CCGCCGCCTGGAAGCGGCCCTCTTCTCCCCCGCCACGCCGCCGCGGCGCCAGGAGAACGGAACCTG
CGCCCCGGACCCCCGCCTCAACTTCTACCCGGTCTTCATGCTGCCCGAGGCCCTGGCCACCTACCT
CCTCTTCTTCCACAACCAAAAGATCCCCGTCAGCTGCCGCGCCAACCGCCCACGAGCCGACGCGCA
CTGGCGGCTGCCCAGTGGGACCCCCTTACCTGACTATCCAACCACCGACGAGGTTTACAAGATCTT
TGAGGGCCTGGGGGACGAGGAGCCGGCCTGCGCCAACCAGGACCTGAAAGAGCGCGACAGCGTGTT
AGTCGAGCTCAAGCTGGACAACCCCCGCCTGGCGGTGGTCAAGCAGTGCATCGCCGTCACCCACTT
CGCCTACCCGGCCCTGGCGCTGCCACCCAAGGTCATGAGCACGCTCATGCAGACCCTGCTGGTGCG
CCGCGCGAGCCCACTCCCCGACGAGGGCGAGACGCCCCTCGAGGACCTCCTGGTGGTCAGCGACGA
GCAGCTGGCCCGCTGGATGCACACCTCGGACCCCAAGGTCCTGGAGGAGCGGCGCAAGACCGTCAC
CGCCGCCTGCATGGTCACGGTGCAGCTCCACTGCATGCACACCTTCCTCACCTCCCGCGAGATGGT
GCGCCGCCTCGGAGAGTGCCTCCACTACATGTTCCGCCAGGGCTACGTCAAGCTAGCTAGCAAGAT
CGCCAATATGGAACTCTCTAACCTGGTCTCCTACTTGGGCATGCTGCACGAAAACAGGCTCGGTCA
GCACGTGCTCCACCACACCCTCAAGCATGAGGCGAGACGCGACTACGTCCGGGACACCATTTACCT
ATACCTGGTCTATACCTGGCAGACCGCCATGGGGGTCTGGCAGCAGTGCCTCGAGGACCGAAACCT
GCGCGCCCTGGAAACGTCTCTGGCTCGCGCTCGCCAGAGCCTGTGGACGGGCTTTGATGAGCGCAC
TATCGCGCAGGACCTCGCCGCGTTCCTTTTCCCCACCAAGCTCGTAGAGACCCTGCAGCGCTCGCT
CCCCGACTTTGCCAGCCAGAGCATGATGCATGCCTTCCGCTCCTTCGTCCTCGAGCGCTCCGGCAT

FIG._1-7

CCTGCCCGCCGTCTGCAACGCGCTCCCCTCTGACTTTGTGCCCACCGTCTACCGCGAGTGCCCGCC
GCCCCTCTGGGCTCACTGCTACCTCCTGCGCCTCGCCAACTTCCTCATGTACCACTGCGACCTCGC
CGAGGACACCTCCGGCGAGGGCCTCTTTGAGTGCTACTGCCGCTGCAACCTCTGCGCACCGCACCG
CTGCCTCGCCACCAACACCGCCCTCCTCAACGAGGTGCAAGCCATCAACACCTTTGAGCTCCAGCG
GCCCCCCAAGCCCGACGGCACCCTGCCACCGCCCTTCAAGCTGACCCCCGGTCTCTGGACCTCCGC
CTTCCTCCGCCACTTTGTCTCCGAGGACTACCACTCGGACCGCATCCTCTTCTACGAGGACGTGTC
CCGCCCCCCCAGGGTGGAGCCCTCCGCCTGCGTCATCACGCACTCGGCCATTCTCGCGCAATTGCA
TGACATCAAAAAGGCCAGGGAAGAGTTTTTGCTGACCAAAGGCCACGGCGTCTACCTAGACCCCCA
CACCGGAGAGGAGCTCAACACCGCCGCCCCGTCCACCGCCCACCATGCCGCCCCTCCGGAGGAAGC
CCATCCGCAGCAGCACCAGCACCAGCAGCAGCCGAGCCACCGCCGCCGCCACCACCGCTCCAGCTA
CGCAGACCGTGTCCGAAGCGAGCTCCACGCCTACGGCGGTGCGACCGGTTCCTCCCGCGACCCTGT
CTCTGGCGGATGCTCTGCCAGAGGAACCCACTCCCGCGATGCTGCTCGAAGAAGAGGCTCTCAGCA
GCGAGACCAGCGGCAGCTCCGAAGGCAGTTTGCTCAGTACCCTCGAGGAACTGGAGGAGGAGGAGG
AACCGGTCACACCGACGAGGCCATCCAAGCCCTCCTACACCAACAGCAGCAGCAGCAAGAGCATCA
GCCAGCGCAGGAACTCCGTCGTCCCCAGCGAGGCTCGTAGATGGAATCAGACATCCATCCACCGGA
GTAGCCAGCCAGGTAGGACACCTCCGCCCTCGGCCCGCCGACGCTCCTGGCGCCGCTACCGCCACG
ACATCCTCTCGGCCCTGGAGTACTGCGCCGGAGACGGAGCCTGCGTGCGCCGGTACCTACTCTACC
ACCACAACATCAACATCCCTTCCAAGATCATCCGTTACTACAAATCCTCTTCCCGTTCCAGCGATC
TCCAGGAAGGCCGCAGCAGCGGCGGCAGCAGAACCAGCCCACGTCAGCCAGCTGAGAGCTAAGATC
TTCCCCACGCTGTACGCCATCTTCCAGCAGAGCCGCGGCGGCCAGGACGCCCTCAAAATCAGGAAC
CGCACCCTGCGCTCCCTCACCAAGAGCTGTCTGTATCACCGCGAGGAGGCCAAGCTGGAACGCACG
CTCTCGGACGCAGAAGCTCTCTTCGAGAAGTACTGCGCTCGGCAGCGGCAGACCCGCCGGTATTTA
AGGAGCGGACCCTGCGTGCGGACACACCATGAGCAAACAAATCCCCACCCCGTACATGTGGTCTTA
TCAGCCACAATCTGGGCGTGCCGCCGGTGCCTCCGTCGATTACTCCACCCGCATGAATTGGCTCAG
TGCCGGGCCTTCCATGATTGGCCAGGTCAATGACATCCGACACACCAGGAACCAGATTCTCATTCG
CCAGGCCCTTATCACCGAGACGCCACGCCCCGTCCAAAATCCCCCGTCCTGGCCCGCCAGCCTGTT
GCCTCAGATGACGCAACCGCCCACCCACCTGCACCTGCCGCGTAACGAAATTTTGGAAGGCAGACT
GACTGACGCCGGCATGCAATTAGCCGGGGGCGGAGCCCTCGCACCCAGAGACTTATATGCCCTGAC
CCTCCGCGGCAGAGGCATCCAGCTCAACGAGGACCTACCCCTCTCGGCGAGCACTCTCCGGCCGGA
CGGCATCTTCCAGCTCGGAGGCGGAGGCCGCTCCTCCTTCAACCCCACCGACGCCTACCTGACGCT
GCAGAACTCCAGCTCCCTTCCCCGCAGCGGCGGCATCGGCAGCGAGCAATTTGTCCGCGAGTTCGT
GCCCACGGTCTACATCAACCCCTTCTCCGGACCGCCCGGGACCTACCCCGACCAGTTCATCGCCAA
CTACAACATCCTAACGGACTCTGTAGCAGGCTATGACTGACGGTCCCCAGGGTCAGCAGCGGCTGC
GGGAGCTCCTCGACCAGCACCGCCGCCAGTGCCCTAACCGCTGCTGCTTCGCCAGGGAAGGGATTC
ACCCGGAGTACTTTTGCATCACCCGCGAGCACTTTGAGGCCGAGTGCATCCCCGACTCTCTGCAAG
AAGGCCACGGTCTGCGCTTCAGCCTCCCCACGCGCTACAGCGACCGCCGCCACCGCGATGGAGACC
GCACCATCCTCACTTCGTACTACTGCGGCCCTGCTTCTTTCAAAGTTCGCTGTCTCTGCGGCCATC
CTGCTCCTCACCCTCTTCTTCTCGACCTTCTGTGTGAGCTGTACAACCGCTCGTAGCGTCAGCCCC
TACACCTCCCCTCGCGTCCAATTTCTGTCCGACATAGAACCAGACTCTGACTCTTACTCGGCTCT
GGCTCTGGGGACGATGAAGATTATGAATATGAGCTGGCTACCAACACACCGAACGAAGACATTCTA
GGCAGCATAGTCATCAACAACCAGATCGGGCCCAAGACCCTGGCCCTGGGATACTTTTATGCCGCC
ATGCAGTTTGTCTTCTTTGCCATCATCATCATCGTCCTCATCCTCTACTACCGCCGCTACGTGCTG
GCCACCGCCCTCATCGTGCAGCGCCAGATGTGGTCCTCCGAGGCCGTCCTGCGGAAAACCTTCTCG
GCCACCGTTGTGGTTACTCCCCCAAAACAAGTCACCCCCTGCAACTGCTCCTGCCGCTTCGAGGAG
ATGGTGTTCTACTACACCACCTCCGTCTTCATGCCCTGGTGGGCCTCATCCTCCTGCTCACCGCCA
TGGTCCGCCTGGCCAACTGGATAGTGGATCAGATGCCCAGCAGGAACCGCGCCCCGCCGCTGCCAC
CGCCCCTCACCTATGTGGGACCCTGCGCCGAGGACCACATCTACGATGAGCCAACCGTAGGGCAAT
ACGTACAGATGAAGTAGCTCCCCCTCTTTCCCATTCCCCCATTTTTCTCTATTCAATAAAGTTGCT
TACCTGAGTTCATCCACACTCGGTCTGCCAGTGCAGTCTATCCATGCGCCGTTTTCCATACTCACA
TAGCGCAGCCGCGCACGCCTCGCCAGGTGACGAAACTGTCGAAATGTAACATTTCGCGCTTCTGTC
AGCAGCACCCCGTTATAGACCAGTTCCACCATGGGACCGAAGAAGCAGAAGCGCGAGCTACCCGAG
GACTTCGATCCAGTCTACCCCTATGACGTCCCGCAGCTGCAGATCAATCCACCCTTCGTCAGCGGG
GACGGATTCAACCAATCCGTGGACGGGGTGCTGTCCCTGCACATCGCACCGCCCCTCGTTTTTGAC
AACACCAGGGCCCTCACCCTGGCCTTCGGGGGAGGTCTACAGCTCTCGGGCAAGCAGCTCGTCGTT
GCCACCGAGGGCTCGGGGCTAACCACCAACCCGGATGGCAAGCTGGTTCTCAAAGTCAAGTCCCCC
ATCACCCTGACCGCCGAGGGCATCTCCCTGTCCCTGGGTCCCGGTCTTTCTAACTCAGAGACCGGC

FIG._1-8

CTCAGTCTGCAAGTCACAGCTCCCCTGCAGTTCCAGGGCAACGCCCTCACTCTTCCCCTCGCCGCC
GGTCTCCAAAACACCGATGGTGGAATGGGTGTCAAACTGGGGAGCGGTCTCACCACGGACAACAGT
CAGGCGGTGACCGTTCAGGTGGGAAATGGACTTCAGCTGAACGGCGAAGGACAACTCACCGTCCCC
GCCACGGCCCCTTTAGTCTCAGGGAGCGCAGGCATCTCTTTCAACTACTCCAGCAATGACTTCGTC
TTAGACAATGACAGTCTCAGTTTGAGGCCAAAGGCCATCTCTGTCACCCCTCCGCTGCAGTCCACA
GAGGACACAATCTCCCTGAATTATTCTAACGACTTTTCTGTGGACAATGGCGCCCTCACCTTGGCT
CCAACTTTCAAACCCTACACGCTGTGGACTGGCGCCTCACCCACAGCAAATGTCATTCTAACAAAC
ACCACCACTCCCAACGGCACCTTTTTCCTATGCCTGACACGTGTGGGTGGGTTAGTTTTGGGTTCC
TTTGCCCTGAAATCATCCATCGACCTTACTAGTATGACCAAAAAGGTCAATTTTATTTTTGATGGG
GCAGGTCGGCTTCAGTCAGACTCCACTTATAAAGGGAGATTTGGATTTAGATCCAACGACAGCGTA
ATTGAACCCACAGCCGCAGGACTCAGTCCAGCCTGGTTAATGCCAAGCACCTTTATTTATCCACGC
AACACCTCCGGTTCTTCCCTAACATCATTTGTATACATTAATCAGACATATGTGCATGTGGACATC
AAGGTAAACACACTCTCTACAAACGGATATAGCCTAGAATTTAACTTTCAAAACATGAGCTTCTCC
GCCCCCTTCTCCACCTCCTACGGGACCTTCTGCTACGTGCCCCGAAGGACAACTCACCGTCCCCGC
CACGGCCCCTTTAGTCTCAGGGAGCGCAGGCATCTCTTTCAACTACTCCAGCAATGACTTCGTCTT
AGACAATGACAGTCTCAGTTTGAGGCCAAAGGCCATCTCTGTCACCCCTCCGCTGCAGTCCACAGA
GGACACAATCTCCCTGAATTATTCTAACGACTTTTCTGTGGACAATGGCGCCCTCACCTTGGCTCC
AACTTTCAAACCCTACACGCTGTGGACTGGCGCCTCACCCACAGCAAATGTCATTCTAACAAACAC
CACCACTCCCAACGGCACCTTTTTCCTATGCCTGACACGTGTGGGTGGGTTAGTTTTGGGTTCCTT
TGCCCTGAAATCATCCATCGACCTTACTAGTATGACCAAAAAGGTCAATTTTATTTTTGATGGGGC
AGGTCGGCTTCAGTCAGACTCCACTTATAAAGGGAGATTTGGATTTAGATCCAACGACAGCGTAAT
TGAACCCACAGCCGCAGGACTCAGTCCAGCCTGGTTAATGCCAAGCACCTTTATTTATCCACGCAA
CACCTCCGGTTCTTCCCTAACATCATTTGTATACATTAATCAGACATATGTGCATGTGGACATCAA
GGTAAACACACTCTCTACAAACGGATATAGCCTAGAATTTAACTTTCAAAACATGAGCTTCTCCGC
CCCCTTCTCCACCTCCTACGGGACCTTCTGCTACGTGCCCCAGAGTGCCTAGAGAACCCTGGCCGT
CAGCCGGCCTCCCCCTTCCCAGGCCACCCGGTACACCACCCGCTCCATGTTTCTGTATGTGTTCTC
CTCCCGCCGCTTGTGCAGCACCACCTCCCGCTGCTCGAGCTGAGGATCCGTGATGGACACAAAGCC
AGGAAGACACATCCTCAGCTCCGTGGGGGCGTCCAACAACTGTTTATGTAAAGGAAAATAAAGACT
CAGAGAAAATCCAAGTTCATATGATTTTTCTTTTATTGATTGGGGGAATTGATTCAGGTGGGGTGT
GCATAATCACAAAAATCACATCAGCAGGTACACACCTGAGACATCAGACAGGGGTAAGGACAGCGC
CTCAGCTTCTGGAACAGACATCAGAAATATTTAATCTGCTGGTAGCTAACACTCCTTCCCAACACC
ATACACTCCTGGAGGGCCCTCTGCCTCTCCTCCTCCCGCTCCGCGTCCCTCTGCCGGGACCACCAC
TCCCCCTCCGTGAACTGCTGCTTCCTCCCCCGCCGCTGCGCCCCGATGGCCTCCGCCGCCAGCTTC
AGCCAGTGCCGCAAGCGCTGGGCGCAGCGCCGAGCCACCGGCTCGCTCAGCTCGTGGCAGCGCCGG
CACACCAGCACTATGTAATTGGCATAGTCCCCGTCACAGTAGATGACCTCCCCCCAGTGGAACATG
CGCAACAGCTTCAGATCACAGTCATACATGATCTTTATGTACATCAGGTGGGCGCCTCGAAACATC
ACACTGCCCACGTACATCACGCGACTCACGCTGGGCAGGTTCACCGCCTCCCTGAACCACCAGAAG
ATGCGATTGTACTCGCAGCCCCGGATGATCTCGCGCATCAGGGAGCGCATCACCACCTGCCCCGCG
CGGCACTCCAGACTGGACCTTTTCAGACAGTGGCAATGAAAGTTCCACAGCGTCGCGCCCGCACAG
CGTCTCCGGGCTGAAACATATCTGCTCCAGCTCCAACCCCCCACACAGGCTGTACTGCAGGAAAAT
CCATTCTTGATGGGAAAGGATGTAGCGCCAGGGGACCACAATCTCCAAACAGGGAACAAAACATAC
CGCGGCCCGGCTGTTGCGCACGGCCCCCACCGGATGCAACGTGCTCACGGAGCAGATACGGGTGGG
ACAGCGGCCCACGTCTCATAGCAAGTCAAGTCCGGAAGTGGCACGGGGTTCGCCACCACTGCTACT
GCTGCCGCTGCGCCACCAGCTCCATCGGCTCCTCCATCCTCCTCCTGTTCCATCGGCTGAGGTGCT
GCCTCCTCCTCCTCCTGCCGCTGCTCCATCATGCTCGTCTGCGGTCATCAGGAGTCAAAAAATTCA
TTGGCCACCGCACGCAGAGAGAACATGGAGCGCAGGGGCCCAGGTGCCCGGCCCGTGCGCTCGCTC
AACTCCCCCAGCAGGTACTCATAGAGATGCTCCTCCAAATCCACCGCAAACCAGGCATGCAGAAAC
TCTTCCGTTCGAGGACCGCCCACGGTAAAGACATAGCCCTCCCGCACCTTCACCGCTGCCAGCTGC
ACGCGCTCATGTCGCTGGGAGTACACCCGGACCCGGGCCTGGATGTACTCCAGCACCTGATCGCTC
AGACACCTCACAGAGATGCCAGCCTGAGCCAGCTTCTCATAGAGAGGTGGCTGAATCTTGAGCTTG
AAGCAGCGAGCGGCTAGGCACTCCCCGCCCCCTTGGAACAGGGCGGCCGGGTCAGCCATGGACTTC
CTCTACATCCGGGGTCCTGGCCACCTCACAAACTATCTGGCCAATCGCCTGACCACGGGTCACCAG
GTAAGGATGATGTCCGTTGTTGCGAATGAGAATGCTCAGAGGTGACTCGGTAGCGTTATCAATCAC
GTCCCCAAAGGTCCAAAGGTCCCAGTTAGAAGTCAGGTGCTTCAGACCGCAGACACGCCCATAGCA
ACCAGTGGGAAAAGCCAGCAAGAGATCCGTGGGCACATGCACCGAAGCTCCCGCAGGAATCTCCAC
CCACTCCGAGGCGTAGACCGTGTAAGCTACACACCCCGCCTCCCGAGTGGGAGCAGAAGCATTCTC

*FIG._1-9*

GCTCAGCCGAAAGAACTTCAGGGTGGCCTGCATATCCTCTTTTACTCACTTGTTAGCAGCTCCACA
CAGACCAGGGTTGTGTTGGCGGGAATAGGCAGCAGGGGTACGTCCCCAGTGAGGGACACCTGGATG
GGGGGCAGAGGATTGATGCCAGGAAGCAGCAGGTACTGGGAAACAGAGACCAGATCCCTCCTCTGA
AAAATCTCGCTCAGTCGGACAAACACAGCAAACCCAGTGGGCACGTAGACTAGCACATTAAAAAGG
ATCACGCTGGGCTGTTCTGACGTCAGCACCAGATGTCGGGACGTGCGCAGATGAATGCGGTTCTGA
TGAATTACCGGAGGCCTCTCACCCGCAGCCAACAGCAGACCGGGCTGCTGATGCGGTCCCGCAGAC
ATATATGAGTTCAATGTGTGTCTTTTTTCTAAACGTCTAGTGAGTGTGCTCGTCCTGCTCCTGCCA
ATCAAAATCCGGGCACCAGGGCTGGTGGTTGGACCCGATGAAGAAGCGAGGAGAGGCGGCCTCCTG
AGTGTGAAGAGTGTCCCGATCCTGCCACGCGAGGTAGGCGAAGTACAGATAGAGCACGGCGAGAAC
AGTCAGCACCGCGGCCAGCAGCAGTCGGTCGTGGGCCATGAGAGGGGGCTGATGGAAGATGGCCG
GTGACTCCTCTCGCCCCGCTTTCGGTTTCTCCTCGTCTCGCTCTCAGTGTCTCTCTCTGTGTCAGC
GCCGAGACGAGTGTGAGCGAACACCGCGAGCGGGCCGGTGATATACCCACAGCGGATGTGGCCACG
CCTGCGGTCGGTTAATCAGTACCCCATCGTCCGATCGGAATTCCCCCGCCTCCGCGTTAACGATTA
ACCCGCCCAGAAGTCCCGGGAATTCCCGCCAGCCGGCTCCGCCGCGACCTGCGACTTTGACCCCGC
CCCTCGGACTTTGACCGTTCCCACGCCACGTCATTTTCCCACGCGACGTCACGTTCCCACGCTACG
TCACACCCCTCTCCACCAATCACCGCCCGCCGCCCCCAACCCTCTCCGCCAATCACCACGCCACAA
AAGGGGCAATAAAAGTGTGCGGTATATTATTGATGATG

*FIG._1-10*

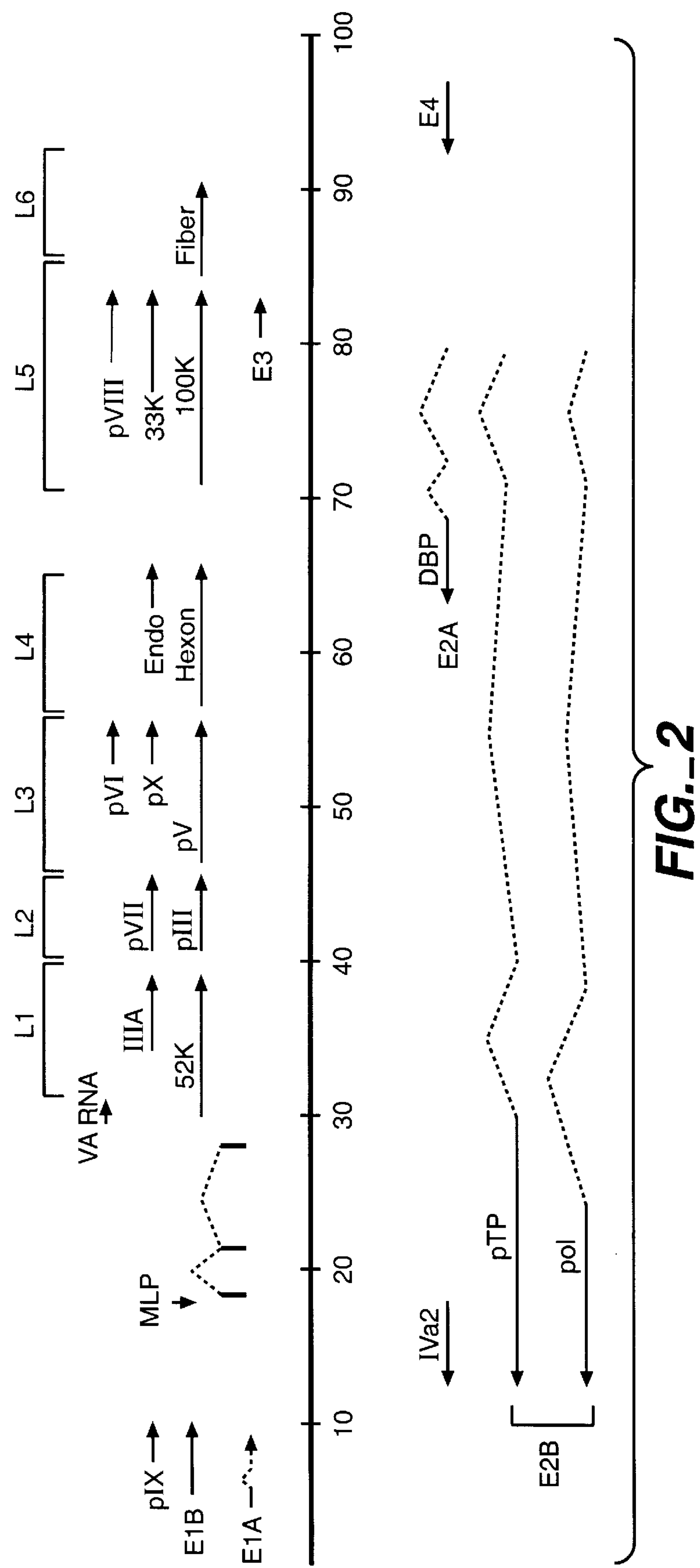
FIG._2

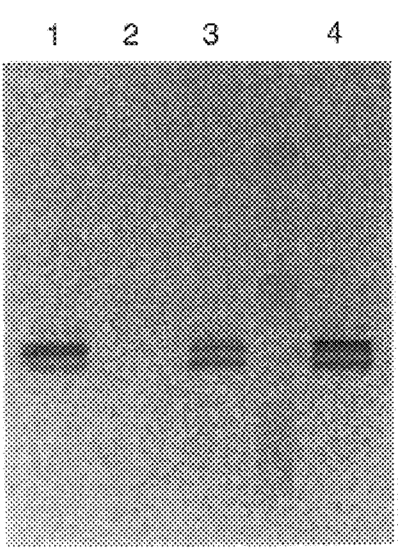
FIG._3A
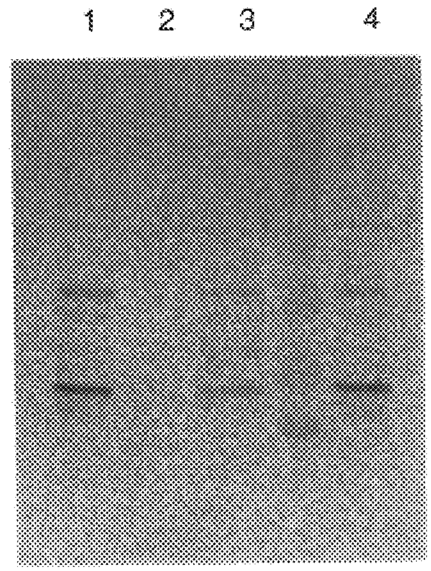
FIG._3B
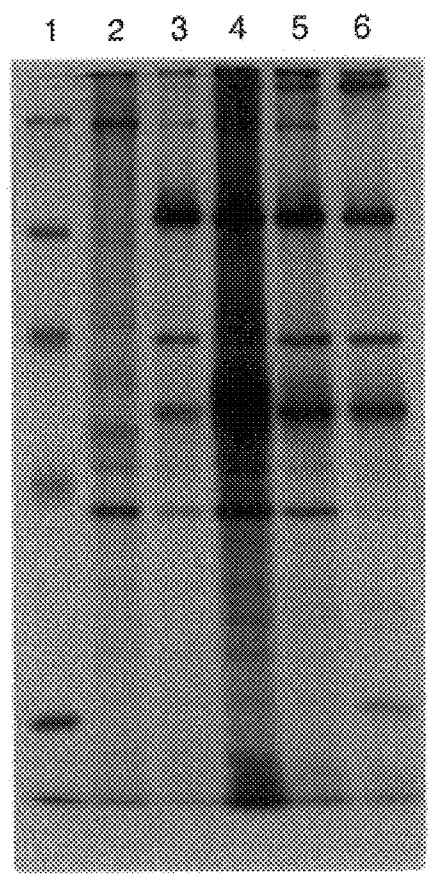
FIG._7

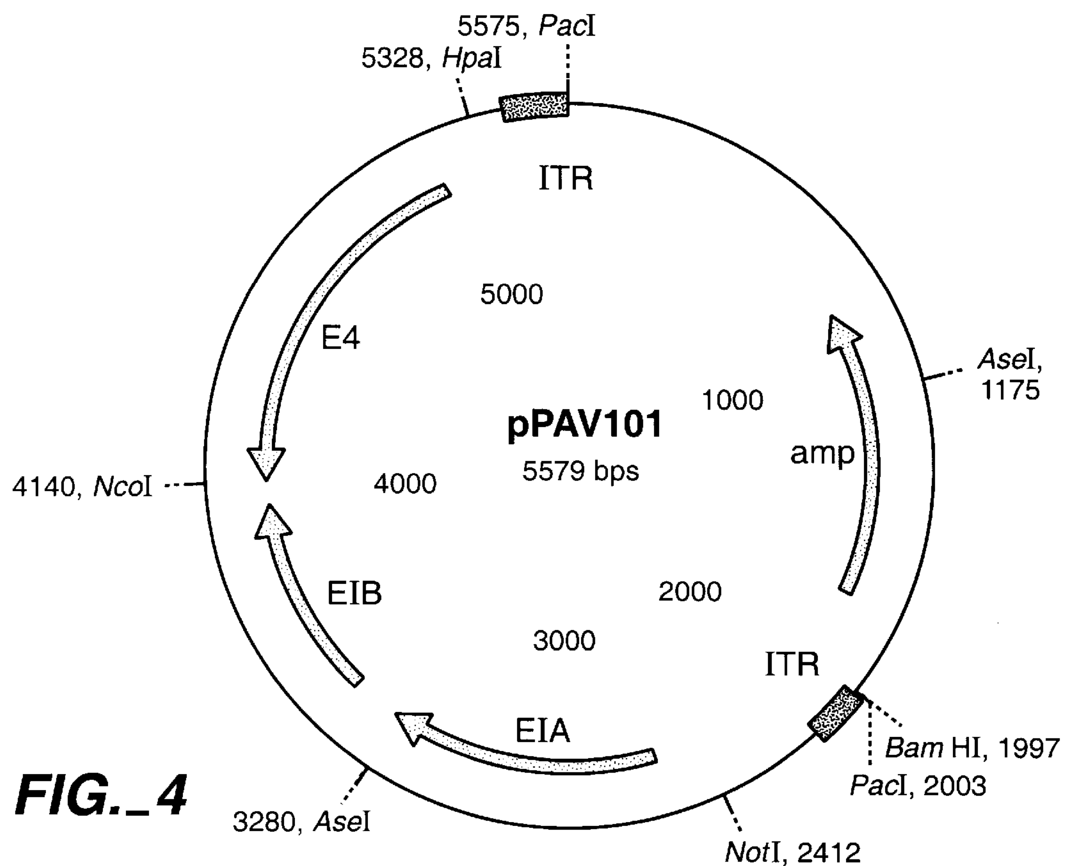
FIG._4
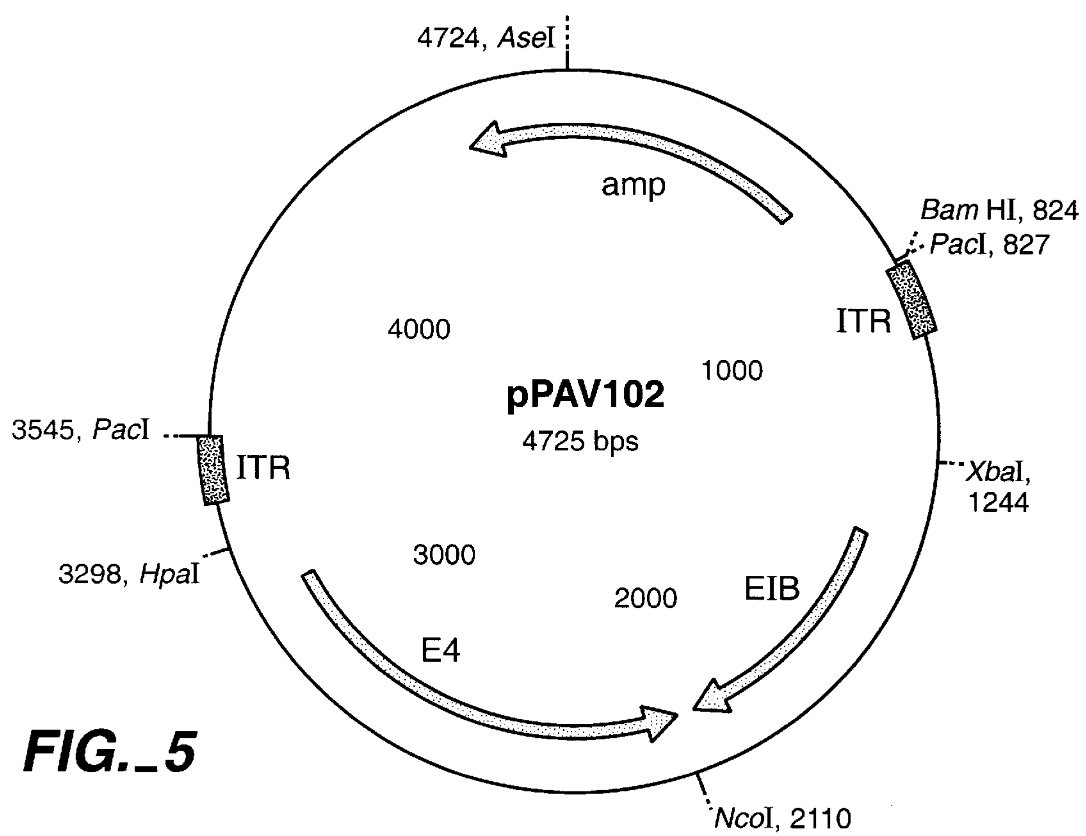
FIG._5

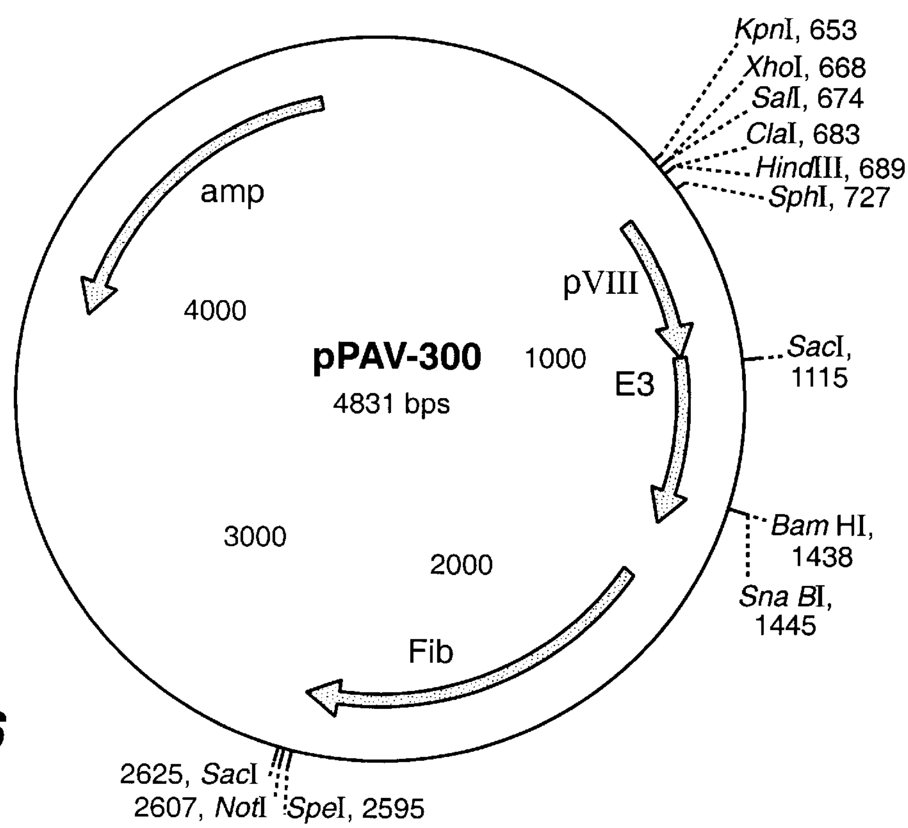
FIG._6
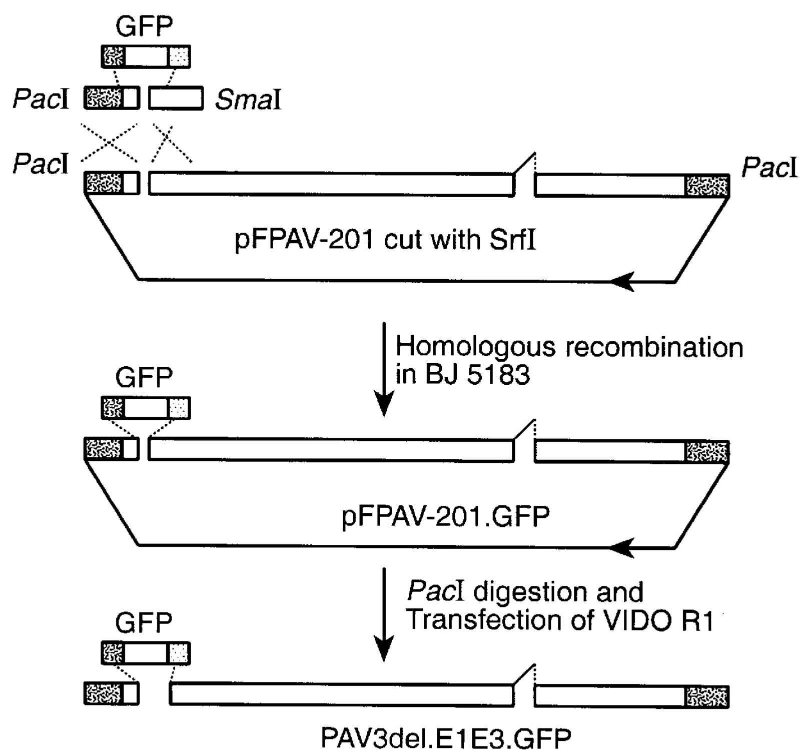
FIG._8

PORCINE ADENOVIRUS TYPE 3 GENOME

CROSS-REFERENCE TO RELATED APPLICATIONS this application claims priority to U.S. Provisional Patent Application Serial No. 60/081,882 filed Apr. 15, 1998, the full disclosure of which is incorporated herein by reference in its entirety.

TECHNICAL FIELD

The present invention is in the field of recombinant mammalian viral vectors. More particularly, it concerns recombinant porcine adenovirus vectors for diagnostic and therapeutic purposes, such as vaccines and expression systems.

BACKGROUND

Adenoviruses are double-stranded DNA viruses that have been isolated from a wide variety of avian and mammalian species, including swine. While the majority of adenovirus infections in swine are subclinical, porcine adenovirus (PAV) infection has been associated with encephalitis, pneumonia, kidney lesions and diarrhea. Derbyshire (1992) In: "Diseases of Swine" (ed. Leman et al.), 7th edition, Iowa State University Press, Ames, Iowa. pp. 225–227. Thus, there is a need for vaccines that will provide protection against PAV infection.

In addition to their potential ability to provide protection against PAV infection, PAVs could also be used as viral vaccine vectors, if insertion capacity can be determined, and appropriate insertion sites can be defined and characterized. It has been shown that PAV is capable of stimulating both humoral response and a mucosal antibody responses in the intestine of infected piglets. Tuboly et al. (1993) *Res. in Vet. Sci.* 54:345–350. Thus, recombinant PAV vaccine vectors would be especially useful, as they would be likely to be capable of providing both systemic and mucosal immunity to antigens encoded by native and/or recombinant PAV genomes.

Cross-neutralization studies have indicated the existence of at least five serotypes of PAV. Derbyshire et al. (1975) *J. Comp. Pathol.* 85:437–443; and Hirahara et al. (1990) *Jpn. J. Vet. Sci.* 52:407–409. Previous studies of the PAV genome have included the determination of restriction maps for PAV Type 3 (PAV-3) and cloning of restriction fragments representing the complete genome of PAV-3. Reddy et al. (1993) *Intervirology* 36:161–168. In addition, restriction maps for PAV-1 and PAV-2 have been determined. Reddy et al. (1995b) *Arch. Virol.* 140:195–200.

Nucleotide sequences have been determined for segments of the genome of various PAV serotypes. Sequences of the E3, pVIII and fiber genes of PAV-3 were determined by Reddy et al. (1995a) *Virus Res.* 36:97–106. The E3, pVIII and fiber genes of PAV-1 and PAV-2 were sequenced by Reddy et al. (1996) *Virus Res.* 43:99–109; while the PAV-4 E3, pVIII and fiber gene sequences were determined by Kleiboeker (1994) *Virus Res.* 31:17–25. The PAV-4 fiber gene sequence was determined by Kleiboeker (1995b) *Virus Res.* 39:299–309. Inverted terminal repeat (ITR) sequences for all five PAV serotypes (PAV-1 through PAV-5) were determined by Reddy et al. (1995c) *Virology* 212:237–239. The PAV-3 penton sequence was determined by McCoy et al. (1996a) *Arch. Virol.* 141:1367–1375. The nucleotide sequence of the E1 region of PAV-4 was determined by Kleiboeker (1995a) *Virus Res.* 36:259–268. The sequence of the protease (23K) gene of PAV-3 was determined by McCoy et al. (1996b) *DNA Seq.* 6:251–254. The unpublished sequence of the PAV-3 hexon gene (and the 14 N-terminal codons of the 23K protease gene) has been deposited in the GenBank database under accession No. U34592. The unpublished sequence of the PAV-3 100K gene has been deposited in the GenBank database under accession No. U82628. The sequence of the PAV-3 E4 region has been determined by Reddy et al. (1997) *Virus Genes* 15:87–90.

Adenoviruses have proven to be effective vectors for the delivery and expression of foreign genes in a number of specific applications, and have a number of advantages as potential gene transfer and vaccine vectors. See Gerard et al (1993) *Trends Cardiovasc. Med* 3:171–177; Imler et al. (1995) *Hum. Gene Ther.* 6:711–721. The ability of these vectors to mediate the efficient expression of candidate therapeutic or vaccine genes in a variety of cell types, including post mitotic cells, is considered an advantage over other gene transfer vectors. Adenoviral vectors are divided into helper-independent and helper-dependent groups based on the region of the adenoviral genome used for the insertion of transgenes. Helper-dependent vectors are usually made by deletion of E1 sequences and substitution of foreign DNA, and are produced in complementing human cell lines that constitutively express E1 proteins. Graham et al. (1977) *J. Gen. Virol.* 36:59–74; Fallaux et al. (1996) *Hum. Gene Ther.* 7:215–222; Fallaux et al. (1998) *Hum. Gene Ther.* 9:1909–1917. However, porcine adenoviruses do not replicate in human cell lines; hence these lines are unsuitable for the propagation of E1-deleted PAV vectors.

Though E1-deleted viruses do not replicate in cells that do not express E1 proteins, the viruses can express foreign proteins in these cells, provided the genes are placed under the control of a constitutive promoter. Xiang et al. (1996) *Virology* 219:220–227. Vaccination of animals with adenovirus recombinants containing inserts in the E1 region induced a systemic immune response and provided protection against subsequent challenge. Imler et al (1995) *Hum. Gene Ther.* 6:711–721; Imler et al. (1996) *Gene Therap* 3:75–84.. This type of expression vector provides a significant safety profile to the vaccine as it eliminates the potential for dissemination of the vector within the vaccinee and therefore, the spread of the vector to nonvaccinated contacts or to the general environment. However, the currently used human adenovirus (HAV) based vectors are endemic in most populations, which provides an opportunity for recombination between the helper-dependent viral vectors and wild type viruses. To circumvent some of the problems associated with the use of human adenoviruses, non human adenoviruses have been explored as possible expression vectors. All vectors developed to date, except one (Klonjkowski et al (1997) *Hum. Gene Ther.* 8:2103–2115), contain an intact E1 region. Use of such vectors for gene therapy in humans and vaccination in animals is unsafe because they have the ability to replicate in normal cells, and they retain the oncogenic potential of the E1 region.

Recombinant PAV genomes containing heterologous nucleotide sequences have not yet been described. Similarly, sites where insertion of heterologous sequence would not interfere with the ability of a PAV vector to stimulate an immune response against a determinant encoded by an inserted sequence have not been identified. Consequently, the development of effective recombinant PAV vectors for use in immunization, expression systems and gene therapy, awaits resolution of these issues. Similarly, there is a need for improved adenoviral vectors lacking E1 replication and oncogenic functions, for expression of transgenes in mammalian cells.

SUMMARY OF THE INVENTION

The present invention provides the complete nucleotide sequence of the porcine adenovirus type 3 (PAV-3) genome. Nucleic acid sequences that are substantially homologous to those comprising a PAV genome are also encompassed by the invention. Substantially homologous sequences include those capable of duplex and/or triplex formation with a nucleic acid comprising all or part of a PAV genome (or with its complement). As is known to those of skill in the art, duplex formation is influcenced by hybridization conditions, particularly hybridization stringency. Factors affecting hybridization stringency are well-known to those of skill in the art. See, for example, Sambrook et al. (1989) Molecular Cloning: A Laboratory Manual; Hames et al. 1985) Nucleic Acid Hybridisation: A Practical Approach, IRL Press Ltd., Oxford Accordingly, it is within the skill of the art to identify a sequence that is substantially homologous to a sequence from a PAV genome.

In addition, novel porcine adenovirus (PAV) expression vector systems comprising PAV genome sequences are disclosed herein. The PAV-3 sequence includes regions into which heterologous sequences can be inserted including, but not limited to, the E1, E3 and E4 regions, and the region between E4 and the right end of the genome. The invention also provides non-essential regions which can be deleted to increase the capacity of a PAV vector for inserted heterologous sequences. These include, but are not limited to, the E3 and E4 regions, and the region between E4 and the right end of the genome. Essential regions, such as E1, can also be deleted, if virus bearing such deletions are propagated in helper cell lines supplying the deleted essential function. Thus, PAV genome sequences can be replaced by one or more foreign genes to generate recombinant PAV vectors expressing heterologous antigenic polypeptides (or antigenic fragments thereof) for the purposes of producing live recombinant virus, subunit vaccines, nucleic acid immunization, or other types of therapy. Multiple heterologous sequences can be inserted into the same, or different, locations in the genome, limited only by the capacity of the virus to accept heterologous sequences. This capacity can be expanded by deletion of viral sequences.

In addition, the invention provides PAV transcriptional and translational regulatory sequences which can be used for expression of heterologous genes that have been inserted into the vectors of the invention. Furthermore, the novel sequences of the present invention can be used for diagnostic purposes, to determine the presence of PAV antigens and/or PAV nucleic acids in a subject or biological sample.

In additional embodiments, the invention provides compositions providing immunity to PAV infection, through expression of antigenic PAV polypeptides. The invention also provides vectors comprising PAV genome sequences, including sequences encoding various PAV genes as well as PAV regulatory sequences, which are useful for controlling the expression of heterologous genes inserted into PAV vectors.

The invention provides defective recombinant PAV vectors that are deleted in their E1 region, as well as helper cell lines providing E1 function, in which such defective vectors can be propagated. Because these defective vectors replicate inefficiently in cells other than the helper cells, they are less likely to stimulate an immune response in a mammalian host. This makes them particularly suitable for use as vaccine vectors. In addition, since the amount of nucleic acid that can be packaged into an adenovirus virion is limited, deletion of the E1 region expands the capacity of these defective vectors, enabling them to accept larger inserts of heterologous sequence. Additional deletions in other regions of the genome can be used to expand the capacity of these defective vectors still further.

The invention further provides methods for obtaining recombinant PAV vectors. In a preferred embodiment, heterologous nucleotide sequences are introduced, through recombinant DNA techniques, into a bacterial plasmid comprising a defined portion of the PAV genome. The recombinant plasmid, containing heterologous sequences flanked by PAV sequences, is introduced into a host cell in combination with a full-length PAV genome or a plasmid containing a full-length or nearly full-length PAV genome. Within the host cell, recombination between the plasmid and the PAV genome generates a recombinant PAV genome. Alternatively, recombinant PAV genomes can be constructed in vitro, using standard techniques in molecular biology and biotechnology.

The invention also provides methods for preparing live recombinant virus and subunit vaccines for inducing protective immune responses to an infectious organism in a mammalian subject. Protective immune responses include humoral (antibody) responses, cell-mediated responses, mucosal responses, or any combination of these. The methods involve insertion, into the porcine adenovirus genome, of heterologous nucleotide sequences encoding one or more protective antigenic determinants of a pathogen. The heterologous sequences are inserted in such a way as to come under the regulatory control of a PAV promoter, or the heterologous sequences are inserted in operative linkage to a eukaryotic transcriptional regulatory sequence. Translation of transcribed heterologous sequences can be controlled by PAV translational regulatory elements, or the heterologous sequence can include non-PAV sequences which regulate its translation.

In another aspect, the invention includes the use of recombinant porcine adenoviruses and recombinant PAV vectors for the expression of a nucleotide or amino acid sequence of interest in a cell system, such as, for example, production of antigen to be used in the preparation of antibodies, or production of antisense RNA.

The invention also includes an expression system comprising a porcine adenovirus expression vector wherein heterologous nucleotide sequences are inserted. The inserted heterologous sequences can comprise one or more regulatory elements for transcription and/or translation, or can be inserted so as to come under the control of PAV regulatory elements. Inserted regulatory elements can be those that are normally associated with the heterologous sequence, or a heterologous sequence can be juxtaposed to and placed in operative linkage with a regulatory element with which it is not normally associated, using standard recombinant DNA techniques. Heterologous sequences can be inserted into a full-length PAV genome, or into a PAV genome which has been deleted in one or more regions. A deletion in the PAV genome can be made to provide a site for insertion of a heterologous sequence, or simply to increase the capacity of the PAV vector to accommodate heterologous sequences inserted at another location.

The invention also provides recombinant PAV polypeptides including, but not limited to, those encoded by the following genes: E1A, E1B, E4, pIX, DBP, pTP, pol, IVa2, 52K, IIIA, pIII, pVII, pV, pX, pVI, and 33K. Such recombinant PAV polypeptides are produced in any eukaryotic expression vector known in the art, into which is inserted a PAV nucleotide sequence according to the invention. Also provided are methods and compositions for recombinant production of heterologous polypeptides and RNAs in a PAV vector. Expression of heterologous polypeptides and RNAs in a PAV vector can be regulated by endogenous PAV regulatory sequences, or by non-PAV sequences. Non-PAV regulatory sequences can be those which normally regulate the heterologous sequence, or they can be sequences that are not normally associated with the heterologous sequence in a regulatory capacity.

Thus, in one embodiment, the invention includes an expression system in which one or more regions of the PAV genome are deleted and replaced with heterologous sequences. In another embodiment, the invention includes a PAV expression system in which heterologous sequences are introduced into the PAV genome without the removal of any PAV sequences. Intergenic regions of the PAV genome comprising regulatory sequences are useful in the practice of the invention for controlling the expression of homologous and heterologous sequences.

The invention also includes recombinant vector systems comprising two or more nucleic acid molecules. In one embodiment, the vector system comprises two plasmids, the first containing a full-length or nearly full-length PAV genome and the second containing a segment of the PAV genome, such as the left end (including the E1 region) or the right end (including the E3 and/or E4 regions). Introduction of heterologous nucleotide sequences into the second plasmid, followed by co-transfection of both plasmids into a suitable host cell, will allow homologous recombination between the two plasmids to generate a viral genome containing inserted heterologous sequences. In another embodiment, the vector system comprises a full-length or nearly full-length PAV genome and a plasmid containing a segment of the PAV genome. Insertion of heterologous sequences into the plasmid, followed by co-transfection and homologous recombination, will generate recombinant PAV genomes as above.

Additional aspects of the invention provide a recombinant PAV comprising a heterologous sequence wherein the heterologous sequence encodes an antigenic determinant of a disease-causing organism; and a recombinant PAV comprising a heterologous sequence wherein the heterologous sequence encodes a foreign gene or fragment thereof. In further embodiments, the invention provides pharmaceutical compositions comprising recombinant PAV for producing an immune response in a mammalian host, the recombinant PAV comprising a heterologous nucleotide sequence encoding a protective determinant of a pathogenic organism. The heterologous sequence is expressed in quantities sufficient for induction of a protective immune response, either through operative linkage to one or more non-PAV regulatory sequences, or through control by endogenous PAV regulatory sequences. The protective immune response can be humoral, cell-mediated and/or mucosal.

The recombinant PAV vectors of the invention will also allow the expression of various therapeutic polypeptides in a wide range of mammalian hosts and are thus useful in the practices of nucleic acid immunization and gene therapy. Exemplary hosts include, but are not limited to, human, equine, bovine, porcine, ovine, caprine, avian, and murine. Those of skill in the art are aware of various therapeutic polypeptides which can be usefully expressed in mammalian hosts. Such therapeutic polypeptides include, but are not limited to, coagulation factors, growth hormones, cytokines, lymphokines, tumor-suppressing polypeptides, cell receptors, ligands for cell receptors, protease inhibitors, antibodies, toxins, immunotoxins, dystrophins, cystic fibrosis transmembrane conductance regulator (CFTR) and immunogenic polypeptides.

The invention also provides diagnostic methods and compositions for the detection of PAV nucleic acids and proteins in a cell or biological sample. The PAV nucleotide sequences disclosed herein can be used as hybridization probes to detect PAV nucleic acids. In addition, the PAV nucleotide sequences disclosed herein encode PAV polypeptides, which can be used for the production of antibodies reactive with various PAV antigens. Such antibodies can be used to detect PAV antigens by immunoassay. Alternatively, PAV polypeptides themselves can be used in competitive immunoassays to detect the presence of PAV antigens in a cell or biological sample. PAV polypeptides can be produced by the PAV vectors of the invention, or can be produced in any mammalian expression vector known in the art.

BRIEF DESCRIPTION OF THE DRAWINGS

FIG. 1 shows the complete nucleotide sequence of the PAV-3 genome (SEQ ID NO: 1).

FIG. 2 shows the transcriptional map of the PAV-3 genome derived from alignment of the sequences of cDNA clones with the genomic sequence, and nuclease protection mapping of viral transcripts. The PAV-3 genome is represented by the thick horizontal line, with the numbers below the line representing PAV-3 map units (i.e., percentage of genome length from the left end). Rightward-reading transcription units are depicted above the line and leftward-reading transcription units are shown below the line.

FIG. 3 shows immunoprecipitation of E1A and E1B proteins from various cell lines.

In FIG. 3A, proteins in cell lysates were separated by gel electrophoresis, and analyzed by immunoblotting using the DP11 monoclonal antibody, which recognizes the human adenovirus E1A protein. Lane 1: 293 cells (human cells transformed by HAV-5, which express adenovirus E1A and E1B); Lane 2: Fetal porcine retinal cells; Lane 3: VIDO R1 cells; Lane 4: 293 cells.

In FIG. 3B, proteins in cell lysates were separated by gel electrophoresis, and analyzed by immunoblotting using the DP17 monoclonal antibody, which recognizes the human adenovirus E1B protein. Lane 1: human 293 cells; Lane 2: Fetal porcine retinal cells; Lane 3: VIDO R1 cells; Lane 4: 293 cells.

FIG. 4 shows a map of the plasmid pPAV-101.

FIG. 5 shows a map of the plasmid pPAV-102.

FIG. 6 shows a map of the plasmid pPAV-300.

FIG. 7 shows proteins labeled after infection of VIDO R1 cells with a recombinant PAV containing the PRV gp50 gene inserted in the E3 region. Labeled proteins were separated by gel electrophoresis; an autoradiogram of the gel is shown. Lane 1: Molecular weight markers of 30K, 46K, 69K and 96K, in order of increasing molecular weight. Lane 2: Mock-infected cells, 12 hours post-infection. Lane 3: PAV-3-infected cells, 12 hours post-infection. Lane 4: cells infected with a recombinant PAV containing the PRV gp50 gene, 12 hours post-infection. Lane 5: cells infected with a recombinant PAV containing the PRV gp50 gene, 16 hours post-infection. Lane 6: cells infected with a recombinant PAV containing the PRV gp50 gene, 24 hours post-infection.

FIG. 8 provides a schematic diagram of the construction of an E1- and E3-deleted PAV vector with a green fluorescent protein gene insertion.

DETAILED DESCRIPTION OF THE INVENTION

The present invention provides the complete nucleotide sequence and transcriptional map of the porcine adenovirus type 3 (PAV-3) genome. The sequence comprises a linear, double-stranded DNA molecule of about 34,094 base pairs, as shown in FIG. 1 (SEQ ID NO: 1). Previously-determined partial sequences can be aligned with the complete genomic sequence as shown in Table 1.

TABLE 1

Alignment of published PAV-3 sequences

| GenBank Accession No. | PAV Gene(s) included within sequence | Reference | Genome coordinates |
|---|---|---|---|
| L43077 | ITR | Reddy et al., 1995c | 1–144 |
| U24432 | penton | McCoy et al., 1996a | 13556–15283 |
| U34592 | hexon; N-terminal 14 codons of 23K (protease) gene | unpublished | 19036–21896 |
| U33016 | protease (23K) | McCoy et al., 1996b | 21897–22676 |
| U82628 | 100K | unpublished | 24056–26572 |
| U10433 | E3, pVIII, fiber | Reddy et al., 1995a | 27089–31148 |
| L43363 | E4 | Reddy et al., 1997 | 31064–34094 |

Know ledge of the PAV genome sequence is useful for both therapeutic and diagnostic procedures. Regions suitable for insertion and regulated expression of heterologous sequences have been identified. These regions include, but are not limited to the E1, E3 and E4 regions, and the region between the E4 region and the right end of the genome. A heterologous nucleotide sequence, with respect to the PAV vectors of the invention, is one which is not normally associated with PAV sequences as part of the PAV genome. Heterologous nucleotide sequences include synthetic sequences. Regions encoding immunogenic PAV polypeptides, for use in immunodiagnostic procedures, have also been identified and are disclosed herein. These include the regions encoding the following PAV proteins: E1A, E1B, E4, pIX, DBP, pTP, pol, IVa2, 52K, IIIA, pIII, pVII, pV, pX, pVI, 33K, pVIII, hexon and fiber (see Table 2). Regions essential for viral replication, such as E1 and E2A, can be deleted to provide attenuated strains for use as vaccines. Nonessential regions, such as parts of the E3 and E4 regions, can be deleted to provide insertion sites, or to provide additional capacity for insertion at a site other than the deleted region. Deletions of viral sequences can be obtained by any method known in the art, including but not limited to restriction enzyme digestion and ligation, oligonucleotide-mediated deletion mutagenesis, and the like.

The practice of the present invention employs, unless otherwise indicated, conventional microbiology, immunology, virology, molecular biology, and recombinant DNA techniques which are within the skill of the art. These techniques are fully explained in the literature. See, e.g., Maniatis et al., *Molecular Cloning: A Laboratory Manual* (1982); *DNA Cloning: A Practical Approach*, vols. I & II (D. Glover, ed.); *Oligonucleotide Synthesis* (N. Gait, ed. (1984)); *Nucleic Acid Hybridization* (B. Hames & S. Higgins, eds. (1985)); *Transcription and Translation* (B. Hames & S. Higgins, eds. (1984)); *Animal Cell Culture* (R. Freshney, ed. (1986)); Perbal, *A Practical Guide to Molecular Cloning* (1984); Ausubel, et al., *Current Protocols In Molecular Biology*, John Wiley & Sons (1987, 1988, 1989, 1990, 1991, 1992, 1993, 1994, 1995, 1996); and Sambrook et al., *Molecular Cloning: A Laboratory Manual* ($2^{nd}$ Edition); vols. I, II & III (1989).

Nucleotide Sequence, Genome Organization, and Transcription Map of Porcine Adenovirus Type 3 (PAV-3)

The complete nucleotide sequence of PAV-3 genome is 34,094 base pairs (bp) in length and has a base composition of 31.3% G, 32.5% C, 18.3% A, and 17.9% T. Thus, the sequence of the PAV-3 genome has a G+C content of 63.8%, which is unusually high when compared with the G+C content of many other animal adenoviruses. The genome termini share inverted terminal repeats (ITR) of 144 bp. Reddy et al., 1995c, supra. The organization of the genome as determined by analysis of open reading frames (ORFs), nuclease protection mapping, and sequencing of cDNA clones, is summarized in Table 2 and FIG. 2.

One important feature of PAV-3 genome is the presence of a short virion associated (VA) RNA gene between the splice acceptor sites of the precursor terminal protein (pTP) and 52 kDa protein genes (FIG. 2). Expression of VA genes increases the kinetics of viral replication; thereby providing the potential for higher yields of recombinant gene products using the PAV vectors of the invention. The locations of the signature sequences present upstream and downstream of VA RNA genes indicate the VA RNA gene of PAV-3 is about 126 nucleotides (nt) in length. This is somewhat shorter than most VA RNAs, whose lengths are 163±14 nts, however shorter VA RNAs have also been reported in HAV-10 and CELO virus. Ma et al. (1996) *J. Virol.* 70:5083–5099; and Chiocca et al. (1996) *J. Virol.* 70:2939–2949. The VA RNA genes were not found in the genomes of BAV-3, CAV-1, and OAV. Reddy et al. (1998) *J. Virol.* 72:1394–1402; Morrison et al. (1997) *J. Gen. Virol.* 78:873–878; and Vrati et al. (1996) *Virology* 220:186–199.

In PAV-3 the major late transcript initiates at 17.7 map units (m.u.: an adenovirus map unit is 1% of genome length, starting from the left end of the genome). There are six 3'-coterminal families of late mRNAs, denoted L1 to L6 (see FIG. 2). All mRNAs produced from the major late promoter (MLP) contain a tripartite leader sequence (TPL). The first portion of the TPL lies next to the MLP and is 61 nts long. The second portion lies within the gene coding for pol and is 68 nt in length. The third portion is 99 nts long and is located within the gene coding for pTP. Thus the TPL of PAV-3 is 228 nt long and is derived from three exons located at 17.7, 20.9, and 28.1 m.u.

The MLP and TPL sequences can be used for expression of a heterologous sequence in a recombinant PAV vector or in any other adenoviral expression system.

TABLE 2

Transcriptional and Translational Features of the PAV-3 Genome

| Region | Gene | Transcription start site | ATG | Splice donor site | Splice acceptor site | Poly(A) signal | Poly(A) addition site |
|---|---|---|---|---|---|---|---|
| E1A | 229R | heterogeneous | 533 | | | 1286 | 1307 |
| | 214R | | 533 | 1043 | 1140 | 1286 | 1307 |
| E1B | 202R | 1382 | 1461 | | | 4085 | 4110, 4112 |
| | 474R | 1382 | 1829 | | | 4085 | 4110, 4112 |

TABLE 2-continued

Transcriptional and Translational Features of the PAV-3 Genome

| Region | Gene | Transcription start site | ATG | Splice donor site | Splice acceptor site | Poly(A) signal | Poly(A) addition site |
|---|---|---|---|---|---|---|---|
| pIX | Pix | 3377 | 3394 | | | 4085 | 4110, 4112 |
| E2A | DBP | 17011c | 24041c | 26949c, 24714c | 24793c, 24051c | 22560c | 22536c |
| E2B | pTP | 17011c | 13638c | 24949c, 24714c | 24793c, 13772c | 4075c | 4053c |
| | pol | 17011c | 13638c | 24949c, 24714c | 24793†c, 13772†c | 4075c | 4053c |
| IVa2 | IVa2 | 5867c | 5711c | 5699c | 5441c | 4075c | 4053c |
| E3 | | 27473 | | | | 28765 | 28793 |
| E4 | | 33730c | | | | 31189c | 31170c |
| L1 | 52K | 6064 | 10629 | 9684 | 10606 | 13601 | 13627 |
| | IIIA | 6064 | 11719 | 9684 | 11715 | 13601 | 13627 |
| L2 | pIII | 6064 | 13662 | 9684 | 13662 | 15698* | 15735 |
| | pVII | 6064 | 15170 | 9684 | 15139 | 15698* | 15735 |
| L3 | pV | 6064 | 15819 | 9684 | 15793 | 18992 | 19013 |
| | pX | 6064 | 17783 | 9684 | 17776 | 18992 | 19013 |
| | pVI | 6064 | 18076 | 9684 | 18063 | 18992 | 19013 |
| L4 | Hexon | 6064 | 19097 | 9684 | 19096 | 22544 | 22567 |
| | Protease | 6064 | 21934 | 9684 | 21931† | 22544 | 22567 |
| L5 | 100k | 6064 | 24056 | 9684 | 24056 | 28765 | 28793 |
| | 33K | 6064 | 26181 | 9684 | 26130 | 28765 | 29793 |
| | pVIII | 6064 | 27089 | 9684 | 26792 | 28765 | 28793 |
| L6 | Fiber | 6064 | 28939 | 9684 | 28910 | 31143 | 31164 |

Notes:
* TTGTTT is present as a polyadenylation signal instead of AATAAA
† The splice acceptor sites for the pol and protease genes were determined based on consensus splice acceptor sequences
"c" refers to sequences on the complementary (leftward-reading) strand of the PAV genome.

Construction of Recombinant PAV Vectors

In one embodiment of the invention, a recombinant PAV vector is constructed by in vivo recombination between a plasmid and a PAV genome. Generally, heterologous sequences are inserted into a plasmid vector containing a portion of the PAV genome, which may or may not possess one or more deletions of PAV sequences. The heterologous sequences are inserted into the PAV insert portion of the plasmid vector, such that the heterologous sequences are flanked by PAV sequences that are adjacent on the PAV genome. The PAV sequences serve as "guide sequences," to direct insertion of the heterologous sequences to a particular site in the PAV genome; the insertion site being defined by the genomic location of the guide sequences.

The vector is generally a bacterial plasmid, allowing multiple copies of the cloned sequence to be produced. In one embodiment, the plasmid is co-transfected, into an appropriate host cell, with a PAV genome comprising a full-length or nearly full-length PAV genomic sequence. The PAV genome can be isolated from PAV virions, or can comprise a PAV genome that has been inserted into a plasmid, using standard techniques of molecular biology and biotechnology. Construction of a plasmid containing a PAV genome is described in Example 2, infra. Nearly full-length PAV genomic sequences can be deleted in regions such as E1, E3, E4 and the region between E4 and the right end of the genome, but will retain sequences required for replication and packaging. PAV genomes can be deleted in essential regions if the essential function can be supplied by a helper cell line.

Insertion of the cloned heterologous sequences into a viral genome occurs by in vivo recombination between a plasmid vector (containing heterologous sequences flanked by PAV guide sequences) and a PAV genome following co-transfection into a suitable host cell. The PAV genome contains inverted terminal repeat (ITR) sequences required for initiation of viral DNA replication (Reddy et al. (1995c), supra), and sequences involved in packaging of replicated viral genomes. Adenovirus packaging signals generally lie between the left ITR and the E1A promoter. Incorporation of the cloned heterologous sequences into the PAV genome thus places the heterologous sequences into a DNA molecule containing viral replication and packaging signals, allowing generation of multiple copies of a recombinant PAV genome that can be packaged into infectious viral particles. Alternatively, incorporation of the cloned heterologous sequences into a PAV genome places these sequences into a DNA molecule that can be replicated and packaged in an appropriate helper cell line. Multiple copies of a single sequence can be inserted to improve yield of the heterologous gene product, or multiple heterologous sequences can be inserted so that the recombinant virus is capable of expressing more than one heterologous gene product. The heterologous sequences can contain additions, deletions and/or substitutions to enhance the expression and/or immunological effect of the expressed gene product(s).

Attachment of guide sequences to a heterologous sequence can also be accomplished by ligation in vitro. In this case, a nucleic acid comprising a heterologous sequence flanked by PAV guide sequences can be co-introduced into a host cell along with a PAV genome, and recombination can occur to generate a recombinant PAV vector. Introduction of nucleic acids into cells can be achieved by any method known in the art, including, but not limited to, microinjection, transfection, electroporation, $CaPO_4$ precipitation, DEAE-dextran, liposomes, particle bombardment, etc.

In one embodiment of the invention, a recombinant PAV expression cassette can be obtained by cleaving a wild-type PAV genome with an appropriate restriction enzyme to produce a PAV restriction fragment representing, for example, the left end or the right end of the genome comprising E1 or E3 gene region sequences, respectively. The PAV restriction fragment can be inserted into a cloning vehicle, such as a plasmid, and thereafter at least one heterologous sequence (which may or may not encode a foreign protein) can be inserted into the E1 or E3 region with or without an operatively-linked eukaryotic transcriptional regulatory sequence. The recombinant expression cassette is contacted with a PAV genome and, through homologous recombination or other conventional genetic engineering methods, the desired recombinant is obtained. In the case wherein the expression cassette comprises the E1 region or some other essential region, recombination between the expression cassette and a PAV genome can occur within an appropriate helper cell line such as, for example, an E1-transformed cell line. Restriction fragments of the PAV genome other than those comprising the E1 or E3 regions are also useful in the practice of the invention and can be inserted into a cloning vehicle such that heterologous sequences can be inserted into the PAV sequences. These DNA constructs can then undergo recombination in vitro or in vivo, with a PAV genome either before or after transformation or transfection of an appropriate host cell.

The invention also includes an expression system comprising a porcine adenovirus expression vector wherein a heterologous nucleotide sequence, e.g. DNA, replaces part or all of the E3 region, part or all of the E1 region, part or all of the E2 region, part or all of the E4 region, part or all of the late region and/or part or all of the regions occupied by the pIX, DBP, pTP, pol, IVa2, 52K, IIIA, pIII, pVII, pV, pX, pVI, and 33K genes. The expression system can be used wherein the foreign nucleotide sequences, e.g DNA, are optionally in operative linkage with a eukaryotic transcriptional regulatory sequence. PAV expression vectors can also comprise inverted terminal repeat (ITR) sequences and packaging sequences.

The PAV E1A, E1B, pIX, DBP, pTP, pol, IVa2, 52K, IIIA, pIII, pVII, pV, pX, pVI, and 33K genes are essential for viral replication. Therefore, PAV vectors comprising deletions in any of these genes, or which lack functions encoded by any of these genes, are grown in an appropriate complementing cell line (i.e., a helper cell line). Most, if not all, of the open reading frames in the E3 and E4 regions of PAV-3 are non-essential for viral replication and, therefore, deletions in these regions can be constructed for insertion or to increase vector capacity, without necessitating the use of a helper cell line for growth of the viral vector.

In another embodiment, the invention provides a method for constructing a full-length clone of a PAV genome by homologous recombination in vivo. In this embodiment, two or more plasmid clones, containing overlapping segments of the PAV genome and together covering the entire genome, are introduced into an appropriate bacterial host cell. Approximately 30 base pairs of overlap is required for homologous recombination in *E. coli.* Chartier et al. (1996) *J. Virol.* 70:4805–4810. Through in vivo homologous recombination, the PAV genome segments are joined to form a full-length PAV genome. In a further embodiment, a recombinant plasmid containing left-end sequences and right-end sequences of the PAV genome, separated by a unique restriction site, is constructed. This plasmid is digested with the restriction enzyme recognizing the unique restriction site, to generate a unit-length linear plasmid, which is introduced into a cell together with a full-length PAV genome. Homologous recombination within the cell will result in production of a recombinant plasmid containing a full-length PAV genome. Recombinant plasmids will also generally contain sequences specifying replication in a host cell and one or more selective markers, such as, for example, antibiotic resistance.

Suitable host cells include any cell that will support recombination between a PAV genome and a plasmid containing PAV sequences, or between two or more plasmids, each containing PAV sequences. Recombination is generally performed in procaryotic cells, such as *E. coli*, while transfection of a plasmid containing a viral genome, to generate virus particles, is conducted in eukaryotic cells, preferably mammalian cells, most preferably porcine cell cultures. The growth of bacterial cell cultures, as well as culture and maintenance of eukaryotic cells and mammalian cell lines are procedures which are well-known to those of skill in the art.

In one embodiment of the invention, a defective recombinant PAV vector is used for expression of heterologous sequences. The defective vector will be deleted in all or part of the E1 region. Construction of a deletion in the E1 region of PAV is described in Example 3, infra. Heterologous sequences can be inserted so as to replace the deleted E1 region, and/or can be inserted at other sites in the PAV genome, preferably E3, E4 and/or the region between E4 and the right end of the genome. Defective vectors with E1 deletions are grown in helper cell lines, which provide E1 function.

Accordingly, in one embodiment of the invention, a number of recombinant helper cell lines are produced according to the present invention by constructing an expression cassette comprising an adenoviral E1 region and transforming host cells therewith to provide complementing cell lines or cultures providing E1 functions. The terms "complementing cell," "complementing cell line," "helper cell" and "helper cell line" are used interchangeably herein to denote a cell line that provides a viral function that is deficient in a deleted PAV, preferably E1 function. These recombinant complementing cell lines are capable of allowing a defective recombinant PAV, having a deleted E1 gene region, wherein the deleted sequences are optionally replaced by heterologous nucleotide sequences, to replicate and express one or more foreign genes or fragments thereof encoded by the heterologous nucleotide sequences. PAV vectors with E1 deletions, wherein heterologous sequences are inserted in regions other than E1, can also be propagated in these complementing cell lines, and will express the heterologous sequences if they are inserted downstream of a PAV promoter or are inserted in operative linkage with a eukaryotic regulatory sequence. Preferred helper cell lines include VIDO R1 cells, as described in Example 1, infra. Briefly, the VIDO R1 cell line is a porcine retinal cell line that has been transfected with DNA from the human adenovirus type 5 (HAV-5) E1 region, and which supports the growth of PAV E1A deletions and HAV-5 E1 deletions.

Transformation of porcine cells with either PAV or HAV has not been reported due to the fact that exposure of permissive or semi-permissive cells to adenovirus normally leads to lysis of infected cells. Graham et al., supra. The approach used in the present study to create a PAV E1-complementing cell line employing the E1 region of HAV-5 is novel as E1A proteins of HAV-5 have been shown for the first time to complement PAV-3 E1 mutants. There are several reasons that the E1 region of HAV-5 was used for transformation of porcine embryonic retinal cells. The E1 region of HAV-5 was shown to transform human retina cells very efficiently. Fallaux et al. (1998) supra. In contrast to the E1 region of PAV-3, the E1 region of HAV-5 has been thoroughly characterized and the monoclonal antibodies against the E1 proteins are readily available from commercial sources. In addition, the E1A region of HAV-5 was shown to complement the E1A functions of several non-human adenoviruses. Ball et al. (1988) *J. Virol.* 62:3947–3957; Zhengetal. (1994) *Virus Res.* 31:163–186.

More generally, defective recombinant PAV vectors, lacking one or more essential functions encoded by the PAV genome, can be propagated in appropriate complementing cell lines, wherein a particular complementing cell line provides a function or functions that is (are) lacking in a particular defective recombinant PAV vector. Complementing cell lines can provide viral functions through, for example, co-infection with a helper virus, or by integrating or otherwise maintaining in stable form a fragment of a viral genome encoding a particular viral function.

In another embodiment of the invention, E1 function (or the function of any other viral region which may be mutated or deleted in any particular viral vector) can be supplied (to provide a complementing cell line) by co-infection of cells with a virus which expresses the function that the vector lacks.

PAV Expression Systems

In one embodiment, the present invention identifies and provides means of deleting regions of the PAV genome, to provide sites into which heterologous or homologous nucleotide sequences encoding foreign genes or fragments thereof can be inserted to generate porcine adenovirus recombinants. In preferred embodiments, deletions are made in part or all of the nucleotide sequences of the PAV E1, E3, or E4 regions and/or the region between E4 and the right end of genome. E1 deletion is described in Example 3; E3 deletion and insertion of heterologous sequence in the E3 region are described in Example 4 and 5; and insertion of a heterologous sequence between the E4 region and the right end of the PAV genome, as well as expression of the inserted sequence, is described in Example 6, infra.

In another embodiment, the invention identifies and provides additional regions of the PAV genome (and fragments thereof) suitable for insertion of heterologous or homologous nucleotide sequences encoding foreign genes or fragments thereof to generate PAV recombinants. These regions include nucleotides 145–13,555; 15,284–19,035; 22,677–24,055; 26,573–27,088; and 31,149–34,094 (SEQ ID NO:1) and comprise the E2 region, the late region, and genes encoding the pIX, DBP, pTP, pol, IVa2, 52K, IIIA, pIII, pVII, pV, pX, pVI, and 33K proteins. These regions of the PAV genome can be used, among other things, for insertion of foreign sequences, for provision of DNA control sequences including transcriptional and translational regulatory sequences, or for diagnostic purposes to detect the presence, in a biological sample, of viral nucleic acids and/or proteins encoded by these regions. Example 7, infra, describes procedures for constructing insertions in these regions.

One or more heterologous sequences can be inserted into one or more regions of the PAV genome to generate a recombinant PAV vector, limited only by the insertion capacity of the PAV genome and ability of the recombinant PAV vector to express the inserted heterologous sequences. In general, adenovirus genomes can accept inserts of approximately 5% of genome length and remain capable of being packaged into virus particles. The insertion capacity can be increased by deletion of non-essential regions and/or deletion of essential regions whose function is provided by a helper cell line.

In one embodiment of the invention, insertion can be achieved by constructing a plasmid containing the region of the PAV genome into which insertion is desired. The plasmid is then digested with a restriction enzyme having a recognition sequence in the PAV portion of the plasmid, and a heterologous sequence is inserted at the site of restriction digestion. The plasmid, containing a portion of the PAV genome with an inserted heterologous sequence, in co-transformed, along with a plasmid (such as pPAV-200) containing a full-length PAV genome, into a bacterial cell (such as, for example, *E. coli*), wherein homologous recombination between the plasmids generates a full-length PAV genome containing inserted heterologous sequences.

Deletion of PAV sequences, to provide a site for insertion of heterologous sequences or to provide additional capacity for insertion at a different site, can be accomplished by methods well-known to those of skill in the art. For example, for PAV sequences cloned in a plasmid, digestion with one or more restriction enzymes (with at least one recognition sequence in the PAV insert) followed by ligation will, in some cases, result in deletion of sequences between the restriction enzyme recognition sites. Alternatively, digestion at a single restriction enzyme recognition site within the PAV insert, followed by exonuclease treatment, followed by ligation will result in deletion of PAV sequences adjacent to the restriction site. A plasmid containing one or more portions of the PAV genome with one or more deletions, constructed as described above, can be co-transfected into a bacterial cell along with a plasmid containing a full-length PAV genome to generate, by homologous recombination, a plasmid containing a PAV genome with a deletion at a specific site. PAV virions containing the deletion can then be obtained by transfection of mammalian cells (such as ST or VIDO R1 cells) with the plasmid containing a PAV genome with a deletion at a specific site.

Expression of an inserted sequence in a recombinant PAV vector will depend on the insertion site. Accordingly, preferred insertion sites are adjacent to and downstream (in the transcriptional sense) of PAV promoters. The transcriptional map of PAV, as disclosed herein, provides the locations of PAV promoters. Locations of restriction enzyme recognition sequences downstream of PAV promoters, for use as insertion sites, can be easily determined by one of skill in the art from the PAV nucleotide sequence provided herein. Alternatively, various in vitro techniques can be used for insertion of a restriction enzyme recognition sequence at a particular site, or for insertion of heterologous sequences at a site that does not contain a restriction enzyme recognition sequence. Such methods include, but are not limited to, oligonucleotide-mediated heteroduplex formation for insertion of one or more restriction enzyme recognition sequences (see, for example, Zoller et al. (1982) *Nucleic Acids Res.* 10:6487–6500; Brennan et al. (1990) *Roux's Arch. Dev. Biol.* 199:89–96; and Kunkel et al. (1987) *Meth. Enzymology* 154:367–382) and PCR-mediated methods for insertion of longer sequences. See, for example, Zheng et al. (1994) *Virus Research* 31:163–186.

It is also possible to obtain expression of a heterologous sequence inserted at a site that is not downstream from a PAV promoter, if the heterologous sequence additionally comprises transcriptional regulatory sequences that are active in eukaryotic cells. Such transcriptional regulatory sequences can include cellular promoters such as, for example, the bovine hsp70 promoter and viral promoters such as, for example, herpesvirus, adenovirus and papovavirus promoters and DNA copies of retroviral long terminal repeat (LTR) sequences.

In another embodiment, homologous recombination in a procaryotic cell can be used to generate a cloned PAV genome; and the cloned PAV-3 genome can be propagated as a plasmid. Infectious virus can be obtained by transfection of mammalian cells with the cloned PAV genome rescued from plasmid-containing cells. Example 2, infra describes construction of an infectious plasmid containing a PAV-3 genome.

The invention provides PAV regulatory sequences which can be used to regulate the expression of heterologous genes. A regulatory sequence can be, for example, a transcriptional regulatory sequence, a promoter, an enhancer, an upstream regulatory domain, a splicing signal, a polyadenylation signal, a transcriptional termination sequence, a translational regulatory sequence, a ribosome binding site and a translational termination sequence.

Therapeutic Genes and Polypeptides

The PAV vectors of the invention can be used for the expression of therapeutic polypeptides in applications such as in vitro polypeptide production, vaccine production, nucleic acid immunization and gene therapy, for example. Therapeutic polypeptides comprise any polypeptide sequence with therapeutic and/or diagnostic value and include, but are not limited to, coagulation factors, growth hormones, cytokines, lymphokines, tumor-suppressing polypeptides, cell receptors, ligands for cell receptors, protease inhibitors, antibodies, toxins, immunotoxins, dystrophins, cystic fibrosis transmembrane conductance regulator (CFTR) and immunogenic polypeptides.

In a preferred embodiment, PAV vectors will contain heterologous sequences encoding protective determinants of various pathogens of swine, for use in subunit vaccines and nucleic acid immunization. Representative swine pathogen antigens include, but are not limited to, pseudorabies virus (PRV) gp50; transmissible gastroenteritis virus (TGEV) S gene; porcine rotavirus VP7 and VP8 genes; genes of porcine respiratory and reproductive syndrome virus (PRRS), in particular ORF 5; genes of porcine epidemic diarrhea virus; genes of hog cholera virus, and genes of porcine parvovirus.

Various foreign genes or nucleotide sequences or coding sequences (prokaryotic, and eukaryotic) can be inserted into a PAV vector, in accordance with the present invention, particularly to provide protection against a wide range of diseases. Many such genes are already known in the art; the problem heretofore having been to provide a safe, convenient and effective vaccine vector for the genes or sequences.

A heterologous (i.e., foreign) nucleotide sequence can consist of one or more gene(s) of interest, and preferably of therapeutic interest. In the context of the present invention, a gene of interest can code either for an antisense RNA, a ribozyme or for an mRNA which will then be translated into a protein of interest. A gene of interest can be of genomic type, of complementary DNA (cDNA) type or of mixed type (minigene, in which at least one intron is deleted). It can code for a mature protein, a precursor of a mature protein, in particular a precursor intended to be secreted and accordingly comprising a signal peptide, a chimeric protein originating from the fusion of sequences of diverse origins, or a mutant of a natural protein displaying improved or modified biological properties. Such a mutant can be obtained by deletion, substitution and/or addition of one or more nucleotide(s) of the gene coding for the natural protein, or any other type of change in the sequence encoding the natural protein, such as, for example, transposition or inversion.

A gene of interest can be placed under the control of regulatory sequences suitable for its expression in a host cell. Suitable regulatory sequences are understood to mean the set of elements needed for transcription of a gene into RNA (ribozyme, antisense RNA or mRNA), for processing of RNA, and for the translation of an mRNA into protein.

Among the elements needed for transcription, the promoter assumes special importance. It can be a constitutive promoter or a regulatable promoter, and can be isolated from any gene of eukaryotic, prokaryotic or viral origin, and even adenoviral origin. Alternatively, it can be the natural promoter of the gene of interest. Generally speaking, a promoter used in the present invention can be chosen to contain cell-specific regulatory sequences, or modified to contain such sequences. For example, a gene of interest for use in the present invention is placed under the control of an immunoglobulin gene promoter when it is desired to target its expression to lymphocytic host cells. There may also be mentioned the HSV-1 TK (herpesvirus type 1 thymidine kinase) gene promoter, the adenoviral MLP (major late promoter), in particular of human adenovirus type 2, the RSV (Rous Sarcoma Virus) LTR (long terminal repeat), the CMV (Cytomegalovirus) early promoter, and the PGK (phosphoglycerate kinase) gene promoter, for example, permitting expression in a large number of cell types.

Alternatively, targeting of a recombinant PAV vector to a particular cell type can be achieved by constructing recombinant hexon and/or fiber genes. The protein products of these genes are involved in host cell recognition; therefore, the genes can be modified to contain peptide sequences that will allow the virus to recognize alternative host cells.

Among genes of interest which are useful in the context of the present invention, there may be mentioned:

- genes coding for cytokines such as interferons and interleukins;
- genes encoding lymphokines;
- genes coding for membrane receptors such as the receptors recognized by pathogenic organisms (viruses, bacteria or parasites), preferably by the HIV virus (human immunodeficiency virus);
- genes coding for coagulation factors such as factor VIII and factor IX;
- genes coding for dystrophins;
- genes coding for insulin;
- genes coding for proteins participating directly or indirectly in cellular ion channels, such as the CFTR (cystic fibrosis transmembrane conductance regulator) protein;
- genes coding for antisense RNAs, or proteins capable of inhibiting the activity of a protein produced by a pathogenic gene which is present in the genome of a pathogenic organism, or proteins (or genes encoding them) capable of inhibiting the activity of a cellular gene whose expression is deregulated, for example an oncogene;
- genes coding for a protein inhibiting an enzyme activity, such as $\alpha_1$-antitrypsin or a viral protease inhibitor, for example;
- genes coding for variants of pathogenic proteins which have been mutated so as to impair their biological function, such as, for example, trans-dominant variants of the tat protein of the HIV virus which are capable of competing with the natural protein for binding to the target sequence, thereby preventing the activation of HIV;
- genes coding for antigenic epitopes in order to increase the host cell's immunity;
- genes coding for major histocompatibility complex classes I and II proteins, as well as the genes coding for the proteins which are inducers of these genes;
- genes coding for antibodies;

- genes coding for immunotoxins;
- genes encoding toxins;
- genes encoding growth factors or growth hormones;
- genes encoding cell receptors and their ligands;
- genes encoding tumor suppressors;
- genes coding for cellular enzymes or those produced by pathogenic organisms; and
- suicide genes. The HSV-1 TK suicide gene may be mentioned as an example. This viral TK enzyme displays markedly greater affinity compared to the cellular TK enzyme for certain nucleoside analogues (such as acyclovir or gancyclovir). It converts them to monophosphorylated molecules, which can themselves be converted by cellular enzymes to nucleotide precursors, which are toxic. These nucleotide analogues can be incorporated into replicating DNA molecules, hence incorporation occurs chiefly in the DNA of dividing cells. This incorporation can result in specific destruction of dividing cells such as cancer cells.

This list is not restrictive, and any other gene of interest can be used in the context of the present invention. In some cases the gene for a particular antigen can contain a large number of introns or can be from an RNA virus, in these cases a complementary DNA copy (cDNA) can be used. It is also possible that only fragments of nucleotide sequences of genes can be used (where these are sufficient to generate a protective immune response or a specific biological effect) rather than the complete sequence as found in the wild-type organism. Where available, synthetic genes or fragments thereof can also be used. However, the present invention can be used with a wide variety of genes, fragments and the like, and is not limited to those set out above.

Recombinant PAV vectors can be used to express antigens for provision of, for example, subunit vaccines. Antigens used in the present invention can be either native or recombinant antigenic polypeptides or fragments. They can be partial sequences, full-length sequences, or even fusions (e.g., having appropriate leader sequences for the recombinant host, or with an additional antigen sequence for another pathogen). The preferred antigenic polypeptide to be expressed by the virus systems of the present invention contain full-length (or near full-length) sequences encoding antigens. Alternatively, shorter sequences that are antigenic (i.e., encode one or more epitopes) can be used. The shorter sequence can encode a "neutralizing epitope," which is defined as an epitope capable of eliciting antibodies that neutralize virus infectivity in an in vitro assay. Preferably the peptide should encode a "protective epitope" that is capable of raising in the host a "protective immune response;" i.e., a humoral (i.e. antibody-mediated), cell-mediated, and/or mucosal immune response that protects an immunized host from infection.

The antigens used in the present invention, particularly when comprised of short oligopeptides, can be conjugated to a vaccine carrier. Vaccine carriers are well known in the art: for example, bovine serum albumin (BSA), human serum albumin (HSA) and keyhole limpet hemocyanin (KLH). A preferred carrier protein, rotavirus VP6, is disclosed in EPO Pub. No. 0259149, the disclosure of which is incorporated by reference herein.

Genes for desired antigens or coding sequences thereof which can be inserted include those of organisms which cause disease in mammals, particularly porcine pathogens such as pseudorabies virus (PRV), transmissible gastroenteritis virus (TGEV), porcine rotavirus, porcine respiratory and reproductive syndrome virus (PRRS), porcine epidemic diarrhea virus (PEDV), hog cholera virus (HCV), porcine parvovirus and the like. Genes encoding antigens of human pathogens are also useful in the practice of the invention.

Therapeutic Applications

With the recombinant viruses of the present invention, it is possible to provide protection against a wide variety of diseases affecting swine, cattle, humans and other mammals. Any of the recombinant antigenic determinants or recombinant live viruses of the invention can be formulated and used in substantially the same manner as described for the antigenic determinant vaccines or live vaccine vectors.

The present invention also includes pharmaceutical compositions comprising a therapeutically effective amount of a recombinant vector, recombinant virus or recombinant protein, prepared according to the methods of the invention, in combination with a pharmaceutically acceptable vehicle and/or an adjuvant. Such a pharmaceutical composition can be prepared and dosages determined according to techniques that are well-known in the art. The pharmaceutical compositions of the invention can be administered by any known administration route including, but not limited to, systemically (for example, intravenously, intratracheally, intraperitoneally, intranasally, parenterally, enterically, intramuscularly, subcutaneously, intratumorally or intracranially) or by aerosolization or intrapulmonary instillation. Administration can take place in a single dose or in doses repeated one or more times after certain time intervals. The appropriate administration route and dosage will vary in accordance with the situation (for example, the individual being treated, the disorder to be treated or the gene or polypeptide of interest), but can be determined by one of skill in the art.

The vaccines of the invention carrying foreign genes or fragments can be orally administered in a suitable oral carrier, such as in an enteric-coated dosage form. Oral formulations include such normally-employed excipients as, for example, pharmaceutical grades of mannitol, lactose, starch, magnesium stearate, sodium saccharin cellulose, magnesium carbonate, and the like. Oral vaccine compositions may be taken in the form of solutions, suspensions, tablets, pills, capsules, sustained release formulations, or powders, containing from about 10% to about 95% of the active ingredient, preferably about 25% to about 70%. An oral vaccine may be preferable to raise mucosal immunity (which plays an important role in protection against pathogens infecting the gastrointestinal tract) in combination with systemic immunity.

In addition, the vaccine can be formulated into a suppository. For suppositories, the vaccine composition will include traditional binders and carriers, such as polyalkaline glycols or triglycerides. Such suppositories may be formed from mixtures containing the active ingredient in the range of about 0.5% to about 10% (w/w), preferably about 1% to about 2%.

Protocols for administering to animals the vaccine composition(s) of the present invention are within the skill of the art in view of the present disclosure. Those skilled in the art will select a concentration of the vaccine composition in a dose effective to elicit antibody, cell-mediated and/or mucosal immune responses to the antigenic fragment. Within wide limits, the dosage is not believed to be critical. Typically, the vaccine composition is administered in a manner which will deliver between about 1 to about 1,000 micrograms of the subunit antigen in a convenient volume of vehicle, e.g., about 1–10 ml. Preferably, the dosage in a single immunization will deliver from about 1 to about 500 micrograms of subunit antigen, more preferably about 5–10 to about 100–200 micrograms (e.g., 5–200 micrograms).

The timing of administration may also be important. For example, a primary inoculation preferably may be followed by subsequent booster inoculations, for example, several weeks to several months after the initial immunization, if needed. To insure sustained high levels of protection against disease, it may be helpful to readminister booster immunizations at regular intervals, for example once every several years. Alternatively, an initial dose may be administered orally followed by later inoculations, or vice versa. Preferred vaccination protocols can be established through routine vaccination protocol experiments.

The dosage for all routes of administration of in vivo recombinant virus vaccine depends on various factors including, the size of patient, nature of infection against which protection is needed, carrier and the like and can readily be determined by those of skill in the art. By way of non-limiting example, a dosage of between approximately $10^3$ pfu and $10^8$ pfu can be used. As with in vitro subunit vaccines, additional dosages can be given as determined by the clinical factors involved.

A problem that has beset the use of adenovirus vectors for immunization and gene therapy in humans is the rapid development of an immunological response (or indeed in some cases existing immunity) to human adenoviruses (HAVs). Recombinant PAV vectors are likely to be less immunogenic in humans and, for this and other reasons, will be useful either as a substitute for HAV vectors or in combination with HAV vectors. For example, an initial immunization with a HAV vector can be followed by booster immunizations using PAV vectors; alternatively, initial immunization with a recombinant PAV vector can be followed by booster immunizations with HAV and/or PAV vectors.

The presence of low levels of helper-independent vectors in the batches of helper-dependent human adenoviruses that are grown in complementing human cell lines has been reported. Fallaux et al. (1998) supra. This occurs as a result of recombination events between the viral DNA and the integrated adenoviral sequences present in the complementing cell line. Hehir et al. (1996) *J. Virol.* 70:8459–8467. This type of contamination constitutes a safety risk, which could result in the replication and spread of the virus. Complete elimination of helper-dependent adenoviruses in the batches of helper-dependent vectors can be achieved using two approaches. The first is by developing new helper cell lines and matched vectors that do not share any common sequences. Fallaux et al. (1998) supra. The second approach is to take advantage of possible cross-complementation between two distantly related adenoviruses such as HAV-5 and PAV-3. VIDO R1 cells contain the E1 coding sequences of HAV-5. Although there is no significant homology between the E1 regions of HAV-5 and PAV-3 at the nucleotide sequence level, the proteins produced from the region can complement each others' function(s). Thus, the problem of helper-independent vector generation by homologous recombination is eliminated when VIDO R1 cells are used for the propagation of recombinant PAV-3.

The invention also encompasses a method of treatment, according to which a therapeutically effective amount of a PAV vector, recombinant PAV, or host cell of the invention is administered to a mammalian subject requiring treatment. The finding that PAV-3 was effective in entering canine, sheep and bovine cells in which it does not replicate or replicates poorly is an important observation. See Example 8, infra. This may have implications in designing PAV-3 vectors for vaccination in these and other animal species.

PAV Expression Systems

Recombinant PAV vectors can be used for regulated expression of foreign polypeptides encoded by heterologous nucleotide sequences. Standard conditions of cell culture, such as are known to those of skill in the art, will allow maximal expression of recombinant polypeptides. They can be used, in addition, for regulated expression of RNAs encoded by heterologous nucleotide sequences, as in, for example, antisense applications and expression of ribozymes.

When the heterologous sequences encode an antigenic polypeptide, PAV vectors comprising insertions of heterologous nucleotide sequences can be used to provide large quantities of antigen which are useful, in turn, for the preparation of antibodies. Methods for preparation of antibodies are well-known to those of skill in the art. Briefly, an animal (such as a rabbit) is given an initial subcutaneous injection of antigen plus Freund's complete adjuvant. One to two subsequent injections of antigen plus Freund's incomplete adjuvant are given at approximately 3 week intervals. Approximately 10 days after the final injection, serum is collected and tested for the presence of specific antibody by ELISA, Western Blot, immunoprecipitation, or any other immunological assay known to one of skill in the art.

Adenovirus E1 gene products transactivate many cellular genes; therefore, cell lines which constitutively express E1 proteins can express cellular polypeptides at a higher levels than other cell lines. The recombinant mammalian, particularly porcine, cell lines of the invention can be used to prepare and isolate polypeptides, including those such as (a) proteins associated with adenovirus E1A proteins: e.g. p300, retinoblastoma (Rb) protein, cyclins, kinases and the like; (b) proteins associated with adenovirus E1B protein: e.g. p53 and the like; growth factors, such as epidermal growth factor (EGF), transforming growth factor (TGF) and the like; (d) receptors such as epidermal growth factor receptor (EGF-R), fibroblast growth factor receptor (FGF-R), tumor necrosis factor receptor (TNF-R), insulin-like growth factor receptor (IGF-R), major histocompatibility complex class I receptor and the like; (e) proteins encoded by proto-oncogenes such as protein kinases (tyrosine-specific protein kinases and protein kinases specific for serine or threonine), p21 proteins (guanine nucleotide-binding proteins with GTPase activity) and the like; (f) other cellular proteins such as actins, collagens, fibronectins, integrins, phosphoproteins, proteoglycans, histones and the like, and (g) proteins involved in regulation of transcription such as TATA-box-binding protein (TBP), TBP-associated factors (TAFs), Sp1 binding protein and the like.

Gene Therapy

The invention also includes a method for providing gene therapy to a mammal, such as a porcine, human or other mammal in need thereof, to control a gene deficiency. In one embodiment, the method comprises administering to said mammal a live recombinant porcine adenovirus containing a heterologous nucleotide sequence encoding a non-defective form of said gene under conditions wherein the recombinant virus vector genome is incorporated into said mammalian genome or is maintained independently and extrachromosomally to provide expression of the required gene in the target organ or tissue. These kinds of techniques are currently being used by those of skill in the art to replace a defective gene or portion thereof. Examples of foreign genes, heterologous nucleotide sequences, or portions thereof that can be incorporated for use in gene therapy include, but are not limited to, cystic fibrosis transmembrane conductance regulator gene, human minidystrophin gene, alpha-1-antitrypsin gene and the like.

In particular, the practice of the present invention in regard to gene therapy in humans is intended for the prevention or treatment of diseases including, but not limited to, genetic diseases (for example, hemophilia, thalassemias, emphysema, Gaucher's disease, cystic fibrosis, Duchenne muscular dystrophy, Duchenne's or Becker's myopathy, etc.), cancers, viral diseases (for example, AIDS, herpesvirus infection, cytomegalovirus infection and papillomavirus infection) and the like. For the purposes of the present invention, the vectors, cells and viral particles prepared by the methods of the invention may be introduced into a subject either ex vivo, (i.e., in a cell or cells removed from the patient) or directly in vivo into the body to be treated. Preferably, the host cell is a human cell and, more preferably, is a lung, fibroblast, muscle, liver or lymphocytic cell or a cell of the hematopoietic lineage.

Diagnostic Applications

The PAV genome, or any subregion of the PAV genome, is suitable for use as a nucleic acid probe, to test for the presence of PAV nucleic acid in a subject or a biological sample. The presence of viral nucleic acids can be detected by techniques known to one of skill in the art including, but not limited to, hybridization assays, polymerase chain reaction, and other types of amplification reactions. Suitable labels and hybridization techniques are well-known to those of skill in the art. See, for example, Kessler (ed.), *Nonradioactive Labeling and Detection of Biomolecules*, Springer-Verlag, Berlin, 1992; Kricka (ed.) *Nonisotopic DNA Probe Techniques*, Academic Press, San Diego, 1992; Howard (ed.) *Methods in Nonradioactive Detection*, Appleton & Lange, Norwalk, 1993; Ausubel et al., supra; and Sambrook et al., supra. Diagnostic kits comprising the nucleotide sequences of the invention can also contain reagents for cell disruption and nucleic acid purification, as well as buffers and solvents for the formation, selection and detection of hybrids.

Regions of the PAV genome can be inserted into any expression vector known in the art and expressed to provide, for example, vaccine formulations, protein for immunization, etc. The amino acid sequence of any PAV protein can be determined by one of skill in the art from the nucleotide sequences disclosed herein. PAV proteins can be used for diagnostic purposes, for example, to detect the presence of PAV antigens. Methods for detection of proteins are well-known to those of skill in the art and include, but are not limited to, various types of direct and competitive immunoassays, ELISA, Western blotting, enzymatic assay, immunohistochemistry, etc. See, for example, Harlow & Lane (eds.): Antibodies, A Laboratory Manual, Cold Spring Harbor Press, New York, 1988. Diagnostic kits comprising PAV polypeptides or amino acid sequences can also comprise reagents for protein isolation and for the formation, isolation, purification and/or detection of immune complexes.

EXAMPLES

Methods

Virus and Viral DNA

The 6618 strain of PAV-3 was propagated in the swine testis (ST) cell line and in E1-transformed porcine retinal cells (VIDO R1, see below). Porcine embryonic retinal cells were obtained from the eyeballs of piglets delivered by caesarian section two weeks before the parturition date. Uninfected cells were grown in MEM supplemented with 10% fetal bovine serum (FBS). MEM with 2% FBS was used for maintenance of infected cells. Viral DNA was extracted either from infected cell monolayers by the method of Hirt (1967) *J. Mol. Biol.* 26:365–369, or from purified virions as described by Graham et al. (1991) in "Methods in Molecular Biology" Vol. 7, Gene transfer and expression protocols, ed. E. J. Murray, Humana Press, Clifton, N.J., pp. 109–128.

Plasmids and Genomic DNA Sequencing

Selected restriction enzyme fragments of PAV-3 DNA were cloned into pGEM-3Z and pGEM-7Zf(+) plasmids (Promega). Nucleotide sequences were determined on both strands of the genome by the dideoxy chain-termination method using Sequenase® enzyme (U.S. Biochemicals) and the dye-terminator method with an Applied Biosystems (Foster City, Calif.) DNA sequencer.

cDNA Library

A cDNA library was generated from polyadenylated RNA extracted from PAV-3 infected ST cells at 12 h and 24 h post infection. Double stranded cDNAs were made with reagents from Stratagene and cloned into Lambda ZAP vector. Plaques which hybridized to specific restriction enzyme fragments of PAV-3 DNA were plaque purified twice. Plasmids containing cDNAs were excised from the Lambda ZAP vector according to the manufacturer's protocol. The resulting plasmid clones were characterized by restriction endonuclease analysis and by sequencing of both ends of the cDNA insert with T3- and T7-specific primers. Selected clones were sequenced with internal primers. cDNA sequences were aligned with genomic sequences to determine the transcription map.

Viral Transcript Mapping by Nuclease Protection

Transcript mapping was conducted according to the method of Berk et al. (1977) *Cell* 12:721–732.

Example 1

Development of an E1-complementing Helper Cell Line (VIDO R1)

Primary cultures of porcine embryonic retina cells were transfected with 10 μg of plasmid pTG 4671 (Transgene, Strasbourg, France) by the calcium phosphate technique. The pTG 4671 plasmid contains the entire E1A and E1B sequences (nts 505–4034) of HAV-5, along with the puromycin acetyltransferase gene as a selectable marker. In this plasmid, the E1 region is under the control of the constitutive promoter from the mouse phosphoglycerate kinase gene, and the puromycin acetyltransferase gene is controlled by the constitutive SV40 early promoter. Transformed cells were selected by three passages in medium containing 7 μg/ml puromycin, identified based on change in their morphology from single foci (i.e., loss of contact inhibition), and subjected to single cell cloning. The established cell line was first tested for its ability to support the growth of E1 deletion mutants of HAV-5. Subsequently the cell line was further investigated for the presence of E1 sequences in the genome by PCR, expression of the E1A and E1B proteins by Western blot, and doubling time under cell culture conditions. E1 sequences were detected, and production of E1A and E1B proteins was demonstrated by immunoprecipitation (FIG. 3). Doubling time was shorter, when compared to that of the parent cell line. Example 3, infra, shows that this cell line is capable of complementing a PAV E1A deletion mutant.

To assess the stability of E1 expression, VIDO R1 cells were cultured through more than 50 passages (split 1:3 twice weekly) and tested for their ability to support the replication of E1-deleted HAV-5. Expression of the E1A and E1B proteins at regular intervals was also monitored by Western blot. The results indicated that the VIDO R1 line retained the ability to support the growth of E1-deleted virus and expressed similar levels of E1 proteins during more than 50 passages in culture. Therefore, VIDO R1 can be considered to be an established cell line.

Example 2

Construction of a Full-length Infectious Clone of PAV-3

A plasmid clone containing a full-length copy of the PAV-3 genome (pPAV-200) was generated by first constructing a plasmid containing left- and right-end sequences of PAV-3, with the PAV-3 sequences bordered by PacI sites and separated by a PstI restriction site (pPAV-100), then allowing recombination between PstI-digested pPAV-100 and an intact PAV-3 genome. Left- and right-end sequences for insertion into pPAV-100 were produced by PCR amplification, as follows.

The plasmid p3SB (Reddy et al., 1993, *Intervirology* 36:161–168), containing the left end of PAV-3 genome (position 1–8870) was used for amplification of the first 433 bp of the PAV-3 genome by PCR. Amplification primers were oligonucleotides 1

(5'-GCGGATCCTTAATTAACATCATCAATAATATA CCGCACACTTTT-3') (SEQ ID NO.: 2) and 2

(5'-CACCTGCAGATACACCCACACACGTCATCTCG-3') (SEQ ID NO.: 3). In the sequences shown here, adenoviral sequences are shown in bold and engineered restriction enzyme sites are italicized.

For amplification of sequences at the right end of the PAV-3 genome, the plasmid p3SA (Reddy et al., 1993, supra) was used. This plasmid was used as template in PCR for amplification of the terminal 573 bp of the genome using oligonucleotide 1 (above) and oligonucleotide 3

(5'-CACCTGCAGCCTCCTGAGTGTGAAGAGTGTCC-3') (SEQ ID NO.: 4). The primers were designed based on the nucleotide sequence information described elsewhere (Reddy et al., 1995c, supra; and Reddy et al., 1997, supra).

For construction of pPAV-100, the PCR product obtained with oligonucleotides 1 and 2 was digested with BamHI and PstI restriction enzymes and the PCR product obtained using primers 1 and 3 was digested with PstI and PacI enzymes. Modified bacterial plasmid pPolyIIsn14 was digested with BamHI and PacI enzymes. This plasmid was used based on its suitability for homologous recombination in *E. coli*. The two PCR products described above were cloned into pPolyIIsn14 by three way ligation to generate the plasmid pPAV-100 which carries both termini of PAV-3, separated by a PstI site and bordered by PacI restriction enzyme sites.

Plasmid pPAV-200, which contains a full length PAV-3 genome, was generated by co-transformation of *E. coli* BJ 5183 recBC sbcBC (Hanahan, 1983, *J. Mol. Biol.* 166:557–580) with PstI-linearized pPAV-100 and the genomic DNA of PAV-3. Extensive restriction enzyme analysis of pPAV-200 indicated that it had the structure expected of a full-length PAV-3 insert, and that no unexpected rearrangements had occurred during recombination in *E. coli*.

The infectivity of pPAV-200 was demonstrated by lipofectin transfection (Life Technologies, Gaithersburg, Md.) of ST cells following PacI enzyme digestion of the plasmid to release the viral genome from the plasmid. Viral plaques were evident 7 days following transfection, and titers were equivalent to, or higher than, those obtained after infection with wild-type PAV. The plaques were amplified and the viral DNA was extracted and analyzed by restriction enzyme digestion. The viral DNA obtained by cleavage of pPAV-200 with PacI contained an extra 3 bases at each end; but these extra bases did not substantially reduce the infectivity of the PAV genome excised from pPAV-200. In addition, the bacterial-derived genomes lacked the 55-kDa terminal protein that is covalently linked to the 5' ends of adenoviral DNAs and which enhances infectivity of viral DNA.

Example 3

Generation of E1 Deletion Mutants of PAV-3

A plasmid (pPAV-101) containing the left (nucleotides 1–2,130) and the right (nucleotides 32,660–34,094) terminal NcoI fragments of the PAV-3 genome was constructed by digesting pPAV-200 with the enzyme NcoI (which has no recognition sites in the vector backbone, but many sites in the PAV insert), gel-purifying the appropriate fragment and self-ligating the ends. See FIG. 4. The E1A sequences of pPAV-101, between nucleotides 407 and 1270 (PAV genome numbering), were deleted by digestion of pPAV-101 with NotI (recognition site at nucleotide 407) and AseI (recognition site at 1270), generation of blunt ends, and insertion of a double-stranded oligonucleotide encoding a XbaI restriction site to create a plasmid, pPAV-102, containing PAV left- and right-end sequences, separated by a NcoI site, with a deletion of the E1 A region and a XbaI site at the site of the deletion. See FIG. 5. Plasmid pPAV-201, containing a full-length PAV-3 genome minus E1A sequences, was created by co-transformation of *E. coli* BJ 5183 with NcoI linearized pPAV-102 and genomic PAV-3 DNA. The resulting construct, when transfected into VIDO R1 cells following digestion with PacI restriction enzyme, produced a virus that had a deletion in the E1 region. In similar fashion, construction of a virus with deletions in E1 and E3 was accomplished by transformation of BJ 5183 cells with NcoI linearized pPAV-102 and genomic PAV-3 DNA containing an E3 deletion. These E1A deletion mutants did not grow on either ST (swine testis) cells or fetal porcine retina cells and could only be grown in the VIDO R1 cell line.

Example 4

Generation of E3 Inserts and Deletion Mutants

To systematically examine the extent of the E3 region that could be deleted, a E3 transfer vector was constructed. The vector (pPAV-301) contained a PAV-3 segment from nucleotides 26,716 to 31,064 with a green fluorescent protein (GFP) gene inserted into the SnaBI site (located at nucleotide 28,702) in the same orientation as E3. The GFP gene was obtained from the plasmid pGreen Lantern-1™ (Life Technologies), by NotI digestion followed by purification of a 732-nucleotide fragment. Similarly, another construct was made with GFP cloned into the SacI site located at nucleotide 27,789. KpnI-BamHI fragments encompassing the modified E3 regions were then isolated from these E3 transfer vectors and recombined in *E coli* with pPAV-200 that had been linearized at nucleotide position 28,702 by SnaBI digestion. Virus were obtained with a construct that had the GFP gene cloned into the SnaBI site.

To delete the non-essential portion of E3 from the transfer vector, a PCR approach was used. In this approach, the region of the PAV genome between nucleotides 27,402 and 28,112 was amplified using the following primers:

5'-GACTGACGCCGGCATGCAAT-3' SEQ ID NO: 5

5'-CGGATCCTGACGCTACGAGCGGTTGTA-3' SEQ ID NO: 6

In a second PCR reaction, the portion of the PAV genome between nucleotides 28,709 and 29,859 was amplified using the following two primers:

5'-CGGATCCATACGTACAGATGAAGTAGC-3' SEQ ID NO: 7

5'- TCTGACTGAAGCCGACCTGC-3' SEQ ID NO: 8

In the oligonucleotides designated SEQ ID NO: 6 and SEQ ID NO: 7, a BamHI recognition sequence is indicated by underlining. The template for amplification was a KpnI-BamHI fragment encompassing nucleotides 26,716–31,063 of the PAV genome, inserted into the plasmid pGEM3Z (Promega), and Pfu polymerase (Stratagene) was used for amplification. The first PCR product (product of amplification with SEQ ID NO: 5 and SEQ ID NO: 6) was digested with BamHI and gel-purified. The second PCR product (product of amplification with SEQ ID NO: 7 and SEQ ID NO: 8) was digested with BamHI and SpeI and gel-purified. They were inserted into SmaI/SpeI-digested pBlueScript II SK(+) (Stratagene) in a three-way ligation reaction to generate pPAV-300. See FIG. 6. pPAV-300 contains the portion of the PAV-3 genome extending from nucleotides 27,402 to 29,859, with 594 base pairs (bp) between nucleotides 28,113 and 28,707 deleted from the E3 region. A virus with such a deletion was constructed as follows. A SphI-SpeI fragment from pPAV-300, containing part of the pVIII gene, a deleted E3 region, and part of the fiber gene was isolated (see FIG. 6). This fragment was co-transfected, with SnaBI-digested pPAV-200 (which contains a full-length PAV-3 genome) into *E. coli*. Homologous recombination generated a plasmid, pFPAV-300, containing a full-length PAV genome with a deletion in the E3 region. pFPAV-300 was digested with PacI and transfected into VIDO R1 cells (Example 1) to generate recombinant virus with a deletion in the E3 region of the genome.

Example 5

Construction of a PAV Recombinant with an Insertion of the PRV gp50 Gene in the PAV E3 Region and Expression of the Inserted Gene To construct a recombinant PAV expressing pseudorabies virus (PRV) gp50, the PRV gp50 gene was inserted at the SnaBI site of pPAV-300 to create plasmid pPAV-300-gp50. A SphI-SpeI fragment from pPAV-300-gp50, containing part of the pVII gene, a deleted E3 region with the PRV gp50 gene inserted, and part of the fiber gene, was purified and co-transfected, along with SnaBI-digested pFPAV-300 (E3-deleted) into *E. coli*. In the bacterial cell, homologous recombination generated pFPAV-300-gp50, a plasmid containing a PAV genome with the PRV gp50 gene replacing a deleted E3 region. Recombinant virus particles were obtained as described in Example 4.

Expression of the inserted PRV gp50 was tested after infection of VIDO R1 cells with the recombinant virus, by $^{35}$S labeling of infected cells (continuous label), followed by immunoprecipitation with an anti-gp50 monoclonal antibody and gel electrophoresis of the immunoprecipitate. FIG. 7 shows that large amounts of gp50 are present by 12 hours after infection, and expression of gp50 persists up to 24 hours after infection.

Example 6

Expression of the Chloramphenicol Acetyltransferase Gene from a Region that Lies Between the Promoter of the E4 Region and the Right ITR The right terminal fragment of the PAV genome (encompassing nucleotides 31,054–34,094) (SEQ ID NO:1) was obtained by XhoI digestion of pPAV-200 and cloned between the XhoI and NotI sites of pPolyIIsn14. A Chloramphenicol acetyltransferase (CAT) gene expression cassette, in which the CAT gene was flanked by the SV40 early promoter and the SV40 polyadenylation signal, was inserted, in both orientations, into a unique HpaI site located between the E4 region promoter and the right ITR, to generate plasmids pPAV-400A and pPAV-400B. The modified terminal fragments were transferred into a plasmid containing a full-length PAV-3 genome by homologous recombination in *E coli* between the isolated terminal fragments and HpaI-digested pPAV-200. Recombinant viruses expressing CAT were obtained following transfection of VIDO R1 cells with the plasmids. PAV-CA2 contained the CAT gene cassette in a leftward transcriptional orientation (i.e., the same orientation as E4 region transcription), while, in PAV-CAT6, the CAT gene cassette was in the rightward transcriptional orientation.

These recombinant viruses were tested for expression of CAT, after infection of VIDO R1 cells, using a CAT Enzyme Assay System from Promega, following the instructions provided by the supplier. See, Cullen (1987) *Meth. Enzymology* 43:737; and Gorman et al, (1982) *Mol. Cell. Biol.* 2:1044. The results are shown in Table 3.

TABLE 3

CAT activity expressed by recombinant PAV viruses

| Sample | $^{3}$H cpm |
|---|---|
| Mock-infected | 458 |
| CAT positive control* | 199,962 |
| PAV-CAT2 | 153,444 |
| PAV-CAT6 | 63,386 |

*the positive control sample contained 0.1 Units of purified CAT.

These results show that recombinant PAV viruses, containing an inserted gene, are viable and are capable of expressing the inserted gene.

Example 7

Construction of Replication Defective PAV-3 Expressing GFP

A 2.3 kb fragment containing the CMV immediate early promoter, the green fluorescent protein (GFP) gene and the bovine growth hormone poly(A) signal was isolated by digesting pQBI 25 (Quantum Biotechnology) with BglII and DraIII followed by filling the ends with T4 DNA polymerase. This fragment was inserted into the SrfI site of pPAV-102 in both orientations to generate pPAV-102GFP (FIG. 8). This plasmid, digested with PacI and SmaI enzymes, and the fragment containing part of the E1 sequence and the GFP gene was gel purified. This fragment and the SrfI digested pFPAV-201 were used to transform *E. coli* BJ 5183 to generate the full-length clone containing GFP in the E1 region (pFPAV-201-GFP) by homologous recombination. The recombinant virus, PAV3delE1E3.GFP was generated following transfection of VIDO R1 cells with PacI restricted pFPAV-201-GFP that had the GFP transcription unit in the opposite orientation to the E1. A similar virus with the GFP in the same orientation as E1 could not be rescued from transfected cells. Presence of the GFP gene in the viral genome was confirmed by restriction enzyme analysis. The recombinant virus replicated in VIDO R1 cells two logs less efficiently than the wild type PAV-3.

Example 8

Virus Entry and Replication of PAV-3 in Human and Animal Cells

To initially characterize the host species restriction of PAV in vitro, monolayers of 11 cell types from 6 different mammalian species were infected with wild type PAV-3 or PAV3del.E1E3.GFP. ST, VIDO R1 (porcine), 293, A549 (human), MDBK, VIDO R2 (bovine), C3HA (mouse), COS, VERO (monkey), sheep skin fibroblasts or cotton rat lung cells were incubated with 1 pfu/cell of wild type PAV-3 or helper-dependent PAV-3 expressing GFP. The cells infected with wild type PAV were harvested at 2 h and 3 days post-infection, subjected to two cycles of freeze-thaw, and virus titers were determined on VIDO R1 cells. Cells that were infected with the recombinant virus expressing GFP were observed with the aid of a fluorescent microscope for green fluorescence.

A ten-fold increase in virus titers in Vero and COS cells, and a hundred-fold increase in cotton rat lung fibroblasts and VIDO R2 cells, was noticed. No increase in the virus titers was observed with 293, A549, MDBK, sheep skin fibroblasts, dog kidney and C3HA cells. All of these cell types showed bright green fluorescence when infected with PAV3delE1E3. GFP except human cells, which showed a weak fluorescence. In addition, low levels of GFP expression were achieved in human cells with recombinant PAV-3. These observations suggest that virus entry into human cells is limited and/or the human cells are non-permissive for the replication of the virus. These results also demonstrated that GFP was expressed by the PAV-3 vector in cells which are semi-permissive (VERO, COS, Cotton rat lung fibroblasts and VIDO R2), or non-permissive (Sheep skin fibroblasts, MDBK and human cells) for virus replication.

Example 9

Insertions in the Regions of the PAV-3 Genome Defined by Nucleotides 145–13,555; 15,284–19,035; 22,677–24,055; 26,573–27,088; and 31,149–34,094 (SEQ ID NO:1)

Insertions are made by art-recognized techniques including, but not limited to, restriction digestion, nuclease digestion, ligation, kinase and phosphatase treatment, DNA polymerase treatment, reverse transcriptase treatment, and chemical oligonucleotide synthesis. Heterologous nucleic acid sequences of interest are cloned into plasmid vectors containing portions of the PAV genome (which may or may not contain deletions of PAV sequences) such that the foreign sequences are flanked by sequences having substantial homology to a region of the PAV genome into which insertion is to be directed. Substantial homology refers to homology sufficient to support homologous recombination. These constructs are then introduced into host cells that are co-transfected with PAV-3 DNA or a cloned PAV genome. During infection, homologous recombination between these constructs and PAV genomes will occur to generate recombinant PAV genome-containing plasmids. Recombinant virus are obtained by transfecting the recombinant PAV genome-containing plasmids into a suitable mammalian host cell line. If the insertion occurs in an essential region of the PAV genome, the recombinant PAV virus is propagated in a helper cell line which supplies the viral function that was lost due to the insertion.

Deposit of Biological Materials

The following materials were deposited and are maintained with the Veterinary Infectious Disease Organization (VIDO), Saskatoon, Saskatchewan, Canada.

The nucleotide sequences of the deposited materials are incorporated by reference herein, as well as the sequences of the polypeptides encoded thereby. In the event of any discrepancy between a sequence expressly disclosed herein and a deposited sequence, the deposited sequence is controlling.

| Material | Internal Accession No. | Deposit Date |
|---|---|---|
| Recombinant plasmids | | |
| pPAV-101 | VIDO 98-1 | Apr. 10, 1998 |
| pPAV-102 | VIDO 98-2 | Apr. 10, 1998 |
| pPAV-200 | VIDO 98-3 | Apr. 10, 1998 |
| pPAV-300 | VIDO 98-4 | Apr. 10, 1998 |
| pPAV-400A | VIDO 98-5 | Apr. 10, 1998 |
| pPAV-400B | VIDO 98-6 | Apr. 10, 1998 |

Recombinant Cell Lines

Porcine embryonic retinal cells transformed with HAV-5 E1 sequences:

| | | |
|---|---|---|
| VIDO R1 | VIDOO 98C-1 | April 10 1998 |

While the foregoing invention has been described in some detail by way of illustration and example for purposes of clarity of understanding, it will be apparent to those skilled in the art that various changes and modifications may be practiced without departing from the spirit of the invention. Therefore the foregoing descriptions and examples should not be construed as limiting the scope of the invention.

What is claimed is:

1. A replication-defective recombinant PAV-3 vector, wherein said PAV-3 vector is capable of duplex formation under conditions of high stringency with the genome of PAV-3 as depicted in SEQ ID NO:1, or its complement, said vector comprising ITR sequences, packaging sequences, and at least one heterologous nucleotide sequence, and wherein the PAV-3 vector lacks E1 function.

2. The replication-defective recombinant PAV-3 vector according to claim 1, wherein the vector is deleted in the E1 region.

3. The replication-defective recombinant PAV-3 vector according to claim 2, wherein the vector is additionally deleted in a region selected from the group consisting of E2, E3, E4, L1, L2, L3, L4, L5, L6 and the region between E4 and the right the genome.

4. The replication-defective recombinant PAV-3 vector according to claim 3, wherein the vector is additionally deleted in more than one region selected from the group consisting of E2, E3, E4, L1, L2, L3, L4, L5, L6 and the region between E4 and the end of the genome.

5. The replication-defective recombinant PAV-3 vector according to claim 1, wherein the heterologous nucleotide sequence encodes a polypeptide selected from the group consisting of coagulation factors, growth hormones, cytokines, lymphokines, tumor-suppressing polypeptides, cell receptors, ligands for cell receptors, protease inhibitors, antibodies, toxins, immunotoxins, dystrophins, cystic fibrosis transmembrane conductance regulator (CFTR) and immunogenic polypeptides.

6. A method for producing a recombinant PAV-3 that comprises introducing the PAV-3 vector of claim 1 into a helper cell line comprising E1 function and recovering virus from the infected cells.

7. A host cell comprising the vector of claim 1.

8. A method for producing a recombinant polypeptide, the method comprising:

(a) providing a population of host cells according to claim 7, and (b) growing said population of cells under conditions whereby the polypeptide is expressed.

9. A composition comprising the replication-defective recombinant PAV-3 vector of claim 1.

10. The composition according to claim 9 further comprising a pharmaceutically acceptable vehicle.

11. A composition capable of inducing an immune response in a mammalian subject, said composition comprising a replication-defective recombinant PAV-3 vector according to claim 1, wherein the vector comprises a heterologous nucleotide sequence that encodes an immunogenic polypeptide; and a pharmaceutically acceptable vehicle.

12. The composition according to claim 11, wherein said immunogenic polypeptide is a pathogen antigen.

13. A recombinant PAV-3 vector comprising a PAV-3 genome capable of duplex formation under conditions of high stringency to the PAV-3 genome as depicted in SEQ ID NO:1, or a complement thereof and at least one heterologous nucleotide sequence, wherein the heterologous nucleotide sequence is inserted in a region selected from the group consisting of the E1 region, the E3 region, the E4 region and the region between E4 and the right end of the genome.

14. The recombinant PAV-3 vector of claim 13, comprising two or more heterologous nucleotide sequences.

15. The recombinant PAV-3 vector of claim 14, wherein the two or more heterologous nucleotide sequences are inserted at different insertion sites.

16. The recombinant PAV-3 vector of claim 13, wherein the heterologous nucleotide sequence encodes a polypeptide selected from the group consisting of coagulation factors, growth hormones, cytokines, lymphokines, tumor-suppressing polypeptides, cell receptors, ligands for cell receptors, protease inhibitors, antibodies, toxins, immunotoxins, dystrophins, cystic fibrosis transmembrane conductance regulator (CFTR) and immunogenic polypeptides.

17. A host cell comprising the vector of claim 13.

18. A method for producing a recombinant polypeptide, the method comprising:

(a) providing a population of host cells according to claim 17, and (b) growing said population of cells under conditions whereby the polypeptide is expressed.

19. A composition comprising the vector of claim 13.

20. The recombinant PAV-3 vector according to claim 13 wherein the heterologous nucleotide sequence is inserted in the E1 region.

21. The recombinant PAV-3 vector according to claim 13 wherein the heterologous nucleotide sequence is inserted in the E3 region.

22. The recombinant PAV-3 vector according to claim 13 wherein the heterologous nucleotide sequence encodes an immunogenic polypeptide.

23. The recombinant PAV-3 vector according to claim 22, wherein said immunogenic polypeptide is a pathogen antigen.

24. The recombinant PAV-3 vector of claim 13, wherein said vector is replication competent.

25. A method for obtaining a recombinant PAV-3 comprising a heterologous nucleotide sequence inserted into a PAV-3 insertion site, the method comprising the steps of:

(a) providing a PAV-3 genome capable of duplex formation under conditions of high stringency to the PAV-3 genome as depicted in SEQ ID NO: 1;

(b) providing a heterologous nucleotide sequence;

(c) linking the heterologous nucleotide sequence to guide sequences, the guide sequences being capable of duplex formation under conditions of high stringency to said PAV-3 genome sequences flanking the PAV-3 insertion site, or the complement of said sequences, such that guide sequences are present at both ends of the heterologous sequence;

(d) introducing the construct from step (c) into a cell together with the PAV-3 genome;

(e) allowing homologous recombination to occur between the two sequences from step (d) to generate a recombinant PAV-3 genome;

(f) purifying the recombinant PAV-3 genome;

(g) inserting the recombinant PAV-3 genome into a mammalian cell;

(h) culturing the mammalian cell under conditions wherein the recombinant PAV-3 genome is replicated and packaged; and (i) optionally collecting the recombinant PAV-3 from the cell or the culture medium.

26. The method according to claim 25 wherein the insertion site is located in a region of the PAV-3 genome selected from the group consisting of the E1 region, the E3 region, the E4 region and the region between E4 and the right end of the genome.

27. The method according to claim 26 wherein the PAV-3 genome is deleted in a region selected from the group consisting of the E1 region, the E3 region, the E4 region and the region between E4 and the right end of the genome.

28. A composition comprising a recombinant PAV-3 obtained according to the method of claim 25.

29. The method according to claim 25 wherein said insertion site is E1.

30. The method according to claim 25 wherein said insertion site is E3.

31. A method for eliciting an immune response in a mammalian host comprising administering a composition comprising a recombinant PAV-3 vector that expresses an immunogenic polypeptide, wherein said PAV-3 vector is capable of duplex formation under conditions of high stringency to the PAV-3 genome as depicted in SEQ ID NO:1, or a complement thereof; and a pharmaceutically acceptable vehicle.

32. The method of claim 31 wherein said PAV-3 vector lacks E1 function.

33. The method of claim 32 wherein said PAV-3 vector is additionally deleted in a region selected from the group consisting of E2, E3, E4, L1, L2, L3, L4, L5, L6 and the region between E4 and the right end of the genome.

34. The method according to claim 31 wherein said immunogenic polypeptide is a pathogen antigen.

35. A method for obtaining a full-length genomic clone of a PAV-3 genome, the method comprising:

(a) providing two or more cloned segments of the PAV-3 genome, wherein said segments are capable of duplex formation under conditions of high stringency to the PAV-3 genome as depicted in SEQ ID NO:1, or a complement thereof, and wherein the cloned segments of the PAV-3 genome, taken together, represent the entire PAV-3 genome;

(b) introducing the two or more cloned segments of the PAV-3 genome into a cell;

(c) allowing homologous recombination to occur within the cell between the two or more cloned segments of the PAV-3 genome to generate a full-length PAV-3 genome; and (d) optionally purifying the full-length PAV-3 genome from the cell.

36. The method of claim 35 wherein said cell is procaryotic cell.

37. The method of claim 36 wherein bacterial cell is *E.coli.*

38. A method for obtaining a recombinant PAV-3 comprising a heterologous nucleotide sequence inserted into a PAV-3 insertion site, comprising the steps of a) introducing a recombinant plasmid into a host cell in combination with a PAV-3 genome, wherein said plasmid comprises a heterologous nucleotide sequence flanked by nucleotide sequences that are capable of duplex formation under conditions of high stringency to PAV-3 nucleotide sequences flanking the PAV-3 insertion site, or the complement of said sequences, and wherein the PAV-3 genome is capable of duplex formation under conditions of high stringency to the PAV-3 genome as depicted in SEQ ID NO:1, or a complement thereof, b) allowing homologous recombination to occur between the plasmid and the PAV-3 genome thereby generating a recombinant PAV-3 comprising said heterologous nucleotide sequences;

c) isolating said recombinant PAV-3;

d) introducing said isolated PAV-3 into a mammalian cell permissive for growth of said PAV-3;

e) culturing said mammalian cell under conditions suitable for PAV-3 replication and packaging; and f) optionally, collecting said recombinant PAV-3 produced from step e).

39. The method of claim 38 wherein said PAV-3 vector lacks E1 function.

40. The method of claim 39 wherein said PAV-3 vector is additionally deleted in a region selected from the group consisting of E2, E3, E4, L1, L2, L3, L4, L5, L6 and the region between E4 and the right end of the genome.

41. The replication-defective recombinant PAV-3 vector according to claim 1 wherein the heterologous nucleotide sequence encodes an immunogenic polypeptide.

42. The replication-defective PAV-3 vector according to claim 41, wherein said immunogenic polypeptide is a pathogen antigen.

43. A vaccine for protecting a mammalian host against infection comprising a recombinant PAV-3 vector comprising a PAV-3 genome capable of duplex formation under conditions of high stringency to the PAV-3 genome as depicted in SEQ ID NO:1, or a complement thereof, and at least one heterologous nucleotide sequence encoding an immunogenic polypeptide, and a pharmaceutically acceptable excipient.

44. The vaccine of claim 43 wherein said immunogenic polypeptide is a pathogen antigen.

* * * * *

UNITED STATES PATENT AND TRADEMARK OFFICE
CERTIFICATE OF CORRECTION

PATENT NO. : 6,492,343 B1
DATED : December 10, 2002
INVENTOR(S) : Police S. Reddy et al.

It is certified that error appears in the above-identified patent and that said Letters Patent is hereby corrected as shown below:

Column 59,
Line 49, after "right" please insert -- end of --;
Line 54, after "E4 and the" please insert -- right --; and Column 62,
Line 44, after "wherein" please insert -- said --.

Signed and Sealed this

Twenty-seventh Day of May, 2003

JAMES E. ROGAN
*Director of the United States Patent and Trademark Office*

Adverse Decisions in Interference

Patent No. 6,492,343, Police Seshidhar Reddy, Suresh Kumer Tikoo, and Lorne A. Babiuk, PORCINE ADENOVIRUS TYPE 3 GENOME, Interference No. 105,358, final judgment adverse to the patentees rendered August 9, 2006, as to claims 13 and 14, 16-19, 21-28, 30-40, 43, and 44.

*(Official Gazette March 20, 2007)*

SEQUENCE LISTING

<160> NUMBER OF SEQ ID NOS: 8

<210> SEQ ID NO 1
<211> LENGTH: 34094
<212> TYPE: DNA
<213> ORGANISM: Porcine Adenovirus Type 3
<220> FEATURE:

<400> SEQUENCE: 1

```
catcatcaat aatataccgc acacttttat tgccccttttt gtggcgtggt gattggcgga     60

gagggttggg ggcggcgggc ggtgattggt ggagaggggt gtgacgtagc gtgggaacgt    120

gacgtcgcgt gggaaaatga cgtgtgatga cgtcccgtgg gaacgggtca aagtccaagg    180

ggaaggggtg gagccctggg gcggtcctcc gcggggcggg gccgagcggc ggaaattccc    240

gcacaggtgg agagtaccgc gggattttgt gccctctgga ccggaccttc gccctccggt    300

gtggcacttc cgcaccacac gtccgcggcc cggtattccc cacctgacga cggtgacacc    360

actcacctga gcggggtgtc cttcgcgctg agaggtccgc ggcggccgcc cgagatgacg    420

tgtgtgggtg tattttttcc cctcagtgta tatagtccgc gcagcgcccg agagtcacta    480

ctcttgagtc cgaagggagt agagttttct ctcagcggaa cagaccctcg acatggcgaa    540

cagacttcac ctggactggg acggaaaccc cgaggtggtg ccggtgctgg aatgggaccc    600

ggtggatctg cgcgacccct ctccggggga tgagggcttc tgtgagccgt gctgggagag    660

tctggtcgat ggactgccgg acgagtggct ggacagtgtg gacgaggtgg aggtgattgt    720

gactgagggg ggtgagtcag aggacagtgg tgggagtgcc gctggtgact caggtggctc    780

tcagggggtc tttgagatgg acccccccaga agagggggac agtaatgagg aggatatcag    840

cgcggtggct gcggaggtgc tgtctgaact ggctgatgtg gtgtttgagg acccacttgc    900

gccaccctct ccgtttgtgt tggactgccc cgaggtacct ggtgtgaact gccgctcttg    960

tgattaccat cgctttcact ccaaggaccc caatctgaag tgcagtctgt gctacatgag   1020

gatgcatgcc tttgctgtct atggtgagtg tttttggaca tttgtgggat tatgtggaaa   1080

aaaaggaaaa agtgcttgta agaaatctca tgtgctattt cccatttttt gtctttttag   1140

aagctgtttc tccagcacct cacaggtcgg gttccccggg acttggagac ctgccaggac   1200

gcaagaggaa gtactgctat gactcatgca gcgaacaacc tttggacctg tctatgaagc   1260

gcccccgcga ttaatcatta acctcaataa acagcatgtg atgatgactg attgtctgtg   1320

tctctgccta tatataccct tgtggtttgc agggaaggga tgtggtgact gagctattcc   1380

tcagcatcat catcgctctg ctttttcta ctgcaggcta tttcttgcta gctcgctgtc    1440

cctttctttt ttctgtgggc atggactatc aacttctggc caagcttact aacgtgaact   1500

accttaggaa ggtgatagta caggggtctc agaactgccc ttggtggaaa aagatttttt   1560

cggacaggtt tatcaaggta gtagcagagg ccaggaggca gtacgggcaa gagttgattg   1620

agatttttgt ggagggtgag aggggctttg gtcctgagtt cctgcgggaa gggggactgt   1680

acgaagaggc cgttctgaaa gagttggatt tcagcacctt gggacgcacc gtagctagtg   1740

tggctctggt ctgcttcatt tttgagaagc ttcagaagca cagcgggtgg actgacgagg   1800

gtattttaag tcttctggtg ccgccactat gttccctgct ggaggcgcga atgatggcgg   1860

agcaggtgcg gcaggggctg tgcatcatca ggatgccgag cgcggagcgg gagatgctgt   1920

tgcccagtgg gtcatccggc agtggcagcg gggccgggat gcgggaccag gtggtgccca   1980
```

-continued

```
agcgcccgcg ggagcaggaa gaggaggagg aggacgagga tgggatggaa gcgagcgggc   2040
gcaggctcga agggccggat ctggtttaga tcgccgccgg cccgggggag cgggtggaga   2100
ggggagcggg gaggaggcgg gggggtcttc catggttagc tatcagcagg tgctttctga   2160
gtatctggag agtcctctgg agatgcatga gcgctacagc tttgagcaga ttaggcccta   2220
tatgcttcag ccgggggatg atctggggga gatgatagcc cagcacgcca aggtggagtt   2280
gcagccgggc acggtgtacg agctgaggcg cccgatcacc atccgcagca tgtgttacat   2340
catcgggaac ggggccaaga tcaagattcg ggggaattac acggagtaca tcaacataga   2400
gccgcgtaac cacatgtgtt ccattgcggg catgtggtcg gtgactatca cggatgtggt   2460
ttttgatcgg gagctaccgg cccggggtgg tctgatttta gccaacacgc acttcatcct   2520
gcacggctgc aacttcctgg gctttctggg ctcggtaata acggcgaacg ccgggggggt   2580
ggtgcgggga tgctactttt tcgcctgcta caaggcgctg gaccaccggg ggcggctgtg   2640
gctgacggtg aacgagaaca cgtttgaaaa gtgtgtgtac gcggtggtct ctgcggggcg   2700
ttgcaggatc aagtacaact cctccctgtc caccttctgc ttcttgcaca tgagctatac   2760
gggcaagata gtggggaaca gcatcatgag cccttacacg ttcagcgacg accccctacgt   2820
ggacctggtg tgctgccaga gcgggatggt gatgcccctg agcacggtgc acatcgctcc   2880
ctcgtctcgc ctgccctacc ctgagttccg caagaatgtg ctcctccgca gcaccatgtt   2940
tgtgggcggc cgcctgggca gcttcagccc cagccgctgc tcctacagct acagctccct   3000
ggtggtggac gagcagtcct accggggtct gagtgtgacc tgctgcttcg atcagacctg   3060
tgagatgtac aagctgctgc agtgtacgga ggcggacgag atggagacgg atacctctca   3120
gcagtacgcc tgcctgtgcg gggacaatca cccctggccg caggtgcggc agatgaaagt   3180
gacagacgcg ctgcgggccc cccggtccct ggtgagctgc aactgggggg agttcagcga   3240
tgacgatgac tgaggatgag tcacccccctc ccctcctctt gcaggtacgt ggccccgccc   3300
agtgggatgg gctttggatg ggggaggggt gttccctata aaagggggat gggggtggag   3360
gcatgcagcc ccacggggaa gcttgtgtgg aggatgtctt ccgagggtga gatccggacc   3420
tgcttcattt cagctcgtct tcccagctgg gccggcgtgc gtcagggagt ggccgggacg   3480
aatgtgaacg gcggagtggt gggcgcccct gcccagagcg gggtgctggc ctactcccgc   3540
ttcgttcagc agcaacagca gcagccgggg acggcggcga cggggtctgt gttccgggcg   3600
gtgtttccat cggtggatct gagcgcggag gtgggcatga tgcggcaggc gctggcggag   3660
ctgcggcagc agctgcagga gctgcgggag gtggtggaga tacagctgcg ggccacggcc   3720
tcggaggcgg ccgaggagga agaggaggag gagattgtgg tggacgagga ggtggcgccc   3780
ggcgctggag cgaacaccat ggaagaggag gaggatgaga tggtcctgac gatgactgtg   3840
gtgggggacc ctgagcctgc tggagtggaa gcccagccgc caccaccacc caccccggag   3900
agcgaccctg cggtgcctgc tactaccact accccgaagc ggctcagcta cggcgcgagc   3960
aagaggagcg gtccatgcgc ggaggacaac tgacgcggac tgtgggggga agaaggggga   4020
ggaggaaaga agaccatgga gacgggtgtt tgtctttttc cagcccaact ttattgagaa   4080
taataataaa gcttatggat gtttggaacg ataatagcgt gtccagcgtt ctctgtcttg   4140
cagggtcttg tgtatcttct cgaggcaccg gtagacctgg tgttggacgt tgaaatacat   4200
gggcatgact ccctcggcgg ggtgcaggta aagccactgg agggctgggt gcgggggcca   4260
ggtgcagtag atgatccagt cataggcgtt ctggttgcgg tggtggttga aaatgtcctt   4320
gaggagcagg ctgatggcgg tgggcagacc cttggtgtag gcattgatga accggttgac   4380
```

-continued

```
ctgggcgggc tgcatgaggg gggacatgat gtggtacttg gcctggatct tgaggttgga   4440
gatgttgccg ctctggtcgc ggcgggggtt catgttgtgg aggacgacga ggacggcgta   4500
gccggtgcag cgggggaagc gggcgtgcag cttggagggg aaggcgtgga agaacttggc   4560
gaccccccttg tgtccgccga ggtcctccat gcactcgtcg aggacgatgg cgatgggtcc   4620
gcgggcggcg gcgcgggcga agacgttgcg tgagtcagtg acatcatagt tgtgctcctg   4680
catgaggtcc tggtagctca tgcggacaaa gtctggcatg agggtggcgg tctgggggat   4740
tagggtgtgg tccggaccgc tgcggtagtt gccctcgcag atctgggtct cccaggcgac   4800
tacctcctgc ggggggatca tgtccacctg cggggtgatg aagaaaacag tctccggcgg   4860
gggggagagg agttgggagg agatgaggtt gcggagcagc tgggacttgc cggagccggt   4920
gggaccgtag atgacagcga tgactggctg gacctggtag ttgagggagc ggcaggtgcc   4980
agccggggtg aggaagggca tgcaggcgtt gagggtgtcg cgcaggttgc ggttctcttg   5040
gacgaggtcc tgcaggaggt gtcggcctcc cagggagagg aggtgggaga gggaggcgaa   5100
ggccttgagg ggcttgaggc cctcggcgta gggcatgtcc tgcagggcct ggtggagcac   5160
gcgcatgcgc tcccagagct cggttacatg tcccacggta tcgtcctcca gcaggtctgg   5220
ttgtttctcg ggttggggtt gctgcgtgag tacggaacga ggcggtgggc gtcgagcggg   5280
tggagggtcc ggtccttcca gggccggagg gcccgcgtga gggtggtctc ggtgacggtg   5340
aagggggcgg tctggggctg ctcggtggcc agggtcctct tgaggctgag gcggctggtg   5400
ctgaaggtgg cgcttccgag ctgcgcgtcg ttcaggtagc actggcggag gaggtcatag   5460
gagaggtgtt gggtggcatg gcccttggcg cggagcttgc cggggccgcg gtgcccgcaa   5520
gcatcgcaaa cggtgtcgcg cagggcgtag agcttggggg cgagcaggac cgtctcggag   5580
ctgtgggcgt cgctgcggca gcgctcgcac tgggtctcgc actcgaccag ccaggtgagc   5640
tgggggttct ggggatcgaa gacgaggggg cccccgttcc gcttgaggcg gtgtttacct   5700
ttggtctcca tgagctcgcg tccggcgcgg gtgaggaaga ggctgtcggt gtccccgtag   5760
acggagcgca ggggccggtc ggcgatgggg gtgccgcggt cgtcggcgta gaggatgagg   5820
gcccactcgg agatgaaggc acgcgcccag gcgaggacga agctggcgac ctgcgagggg   5880
tagcggtcgt tgggcactaa tggcgaggcc tgctcgagcg tgtggagaca gaggtcctcg   5940
tcgtccgcgt ccaggaagtg gattggtcgc cagtggtagt ccacgtgacc ggcttgcggg   6000
tcgggggggta taaaaggcgc gggccggggt gcgtggccgt cagttgcttc gcaggcctcg   6060
tcaccggagt ccgcgtctcc ggcgtctcgc gctgcggctg catctgtggt cccggagtct   6120
tcaggtgggt acgctacgac aaagtccggg gtgacctcag cgctgaggtt gtctgtttct   6180
atgaaggcgg aggagcggac ggagaggtcg ccgcgggcga tggcttcggt ggtgcgggcg   6240
tccatctggc tggcgaagac caccttctta ttgtcgaggc gtgtggcgaa actgccgtag   6300
agggcgttgg agagaagctt ggcgatgctg cggagcgttt ggtttctgtc ccggtcggcc   6360
ttttccttgg cagcgatgtt gagctgcacg tagtctcggg cgaggcagcg ccactcgggg   6420
aagatgctgt tgcgctcgtc cggcaggagg cgcacggccc agccacggtt gtggagggtg   6480
accacgtcca cggaggtggc tacctcgccg cggaggggct cgttggtcca gcagaggcgg   6540
ccgcccttgc gggagcagta ggggggcagg acgtccagct ggtcctcgtc gggggggtcg   6600
gcgtcgatgg tgaagagggc gggcaggagg tcggggtcga agtagctgag gggctcgggg   6660
ccgtcgaggc ggtcctgcca gcggcgggcg gccagggcgc ggtcgaaggg gttgaggggt   6720
```

-continued

```
tggccggcgg ggaaggggtg ggtgagggcg ctggcataca tgccgcagat gtcatagacg   6780
tagaggggct cccgcaggag gccgatgaag ttggggtagc agcggccgcc gcgcaggctc   6840
ttcgcggacg tagtcataca gctcgtggga gggcgcgagg aggttcggcc gaggtgcggc   6900
gcctggggcc ggctggcgcg gtagaggagc tgcttgaaga tggcgtggga gttggagctg   6960
atggtgggcc tctggaagac attgaaggcg gcgtggggaa ggccggcctg cgtgtggacg   7020
aaggcgcggt aggactcttg cagcttgcgg accagacggg cggtgacgac gacgtcctgg   7080
gcgcagtagc gcagggtggc ctggacgatg tcgtaagcgt ccccctggct ctccttcttc   7140
cacaggtcct tgttgaggag gtactcctga tcgctgtccc agtacttggc gtgtgggaag   7200
ccgtcctgat cgcgtaagta gtcccccgtg cggtagaact cgttcacggc atcgtagggg   7260
cagtgtccct tgtccacggc cagctcgtag gccgcggcgg ccttgcggag gctggtgtgc   7320
gtgagggcga aggtgtcccg gaccatgaac ttgacgtact ggtgctgggg gtcctcgggg   7380
gccatgacgc cctcctccca gtccgcgtag tcgcggcgcg ggcggaaggc ggggttgggc   7440
aggttgaagc tgatgtcatt gaagaggatg cggccgttgc gcggcatgaa ggtgcgggtg   7500
accaggaagg aggggggcac ctcgcggcgg tgggcgagca cctgcgcggc caggacgatc   7560
tcatcgaagc ccgagatgtt gtggcccacg atgtagacct ccaggaagag gggcggcccg   7620
cgcaggcggc ggcgccgcag ctgggcatag gccagggggt cctcggggtc gtccggcagg   7680
ccggggcccc gctcctgcgc cagctcggcg aggtctgggt tgtgggccag caggtgctgc   7740
cagagggtgt cggtgaggcg ggcctgcagg gcgtgccgca gggccttgaa ggcgcggccg   7800
atggcgcgct tctgcgggca gagcatgtag aaggtgtggg ctcgggtctc cagcgctgca   7860
ggcgggctct ggacggccac cacctgcagc gcggcgtcca gcagctcctc gtcccccgag   7920
aggtggaaga ccagcaggaa gggcacgagc tgctttccga agcggccgtg ccaggtgtag   7980
gtctccaggt cataggtgag gaagaggcgg cgggtgccct cgggggagcc gatggggcgg   8040
aaggcgatgg tctgccacca gtcggccgtc tggcgctgaa cgtggtggaa gtagaagtcc   8100
cggcggcgca cggagcaggt gtgggcggtc tggaagatgc ggccgcagtg ctcgcacttc   8160
tgggcctcct ggatgctctt gatgaggtgg cagcggccct gggtgaagag caggcggagg   8220
gggaagggga ggcggggcgg cgggccctcg ggcggggggt cccagcgcac gtggtgcagg   8280
tggtgttgct ggcgggtgac cacctggacg aaggtgggcc cggcggcgcg ggccagctcc   8340
accgcggtct gggggtagc ctgcaggagg tcggggggcg ggcgcaggag gtgcagctgg   8400
aagaggttgg ccagggcgct gtcccagtgg cggtggtagg tgatgctcca gctctccccg   8460
tcctgggtgg tgccctggag gcggagggtg gcgcggcgct cgagcaggag cccccgcgtg   8520
ccggcctccg cggcctcggc ggcggcggcc ggtctcaggc gggcagctgg gccaggggca   8580
cgggcgcgtt gagctcgggc agcgggaggt ggtcgcggcg cagacgcgag gcgtgggcga   8640
tgacgcggcg gttgatgttc tggatctgcg ggttcccgga gaagaccacg ggcccggtga   8700
ctcggaacct gaaagagagt tccacggaat caatgtcggc atcgtgggtg gccacctggc   8760
gcaggatctc ggacacgtcc ccgctgtttt cgcggtaggc gatgtcctgc atgaactgct   8820
cgagctcgtc ctcgtccagg tccccgtggc cggcgcgctc cacggtggcg gccaggtcga   8880
cggtgatgcg gttcatgatg gccaccaggg cgttctctcc gttctcgttc cacacgcgac   8940
tgtagaccag ctggccgtcg gcgtcccgcg cgcgcatgac tacctgggcc aggttgagcg   9000
ccaccaggcg gttgaagggc gcctgcaggc gcagggcgtg gtgcaggtag ttgagggtgg   9060
tggcgatgtg ctcgcagagg aagaagttta tgacccagcg gcgcagggtc agctcgttga   9120
```

-continued

```
tgtcgcccag gtcctcgagg cgctgcatga cccggtagaa ctcgggggcg aagcgaaaaa   9180
actcgtgctg gcgggccgag accgtgagct cctcttccag ggcggcgatg gcctcggcca   9240
ccgcctgccg cacctcctcc tctaaggagg gcgggggcgt gctgggtccg gccaccgccg   9300
cctcttcttc ctcttctccc tccaggggtg gcatctcctc gtcttcttct tctgctgctg   9360
ctgcctccgc ggggacgggg ggcgcaggcc ggggacggcg ccggcgcaag ggcagccggt   9420
ccacgaagcg ctcgatgacc tcgccccgca tgcggcgcat ggtctcggtg acggcgcggc   9480
cgccctcccg gggccgcagc tcgaaggcgc ccccgcgcag cgcggtgccg ctgcagaggg   9540
gcaggctgag cgcactgatg atgcagcgtg tcaactctct cgtaggtacc tcctgctgtt   9600
gcagcgcttc ggcaaactcg cgcacctgct cttcggaccc ggcgaagcgt tcgacgaagg   9660
cgtctagcca gcaacagtcg caaggtaagt tgagcgcggt gtgcgtcggg agccggaggt   9720
gccggctgac gaggaagtga aagtaggccg tcttgagctg ccggatggcg cgcaggaggg   9780
tgaggtcttt gcggccggcg cgctgcaggc ggatgcggtc ggccatgccc caggcctcct   9840
gctggcagcg gccgatgtcc ttgagctgct cctgcagcag atgtgccacg ggcacgtccc   9900
ggtcggcgtc caggtgggtg cgaccgtagc cccgcagggg gcgcagcagc gccaggtcgg   9960
ccaccacgcg ctcggccagg atggcctgct gcatgcgctg cagggagtct gagaagtcat  10020
ccaggtccag gaaccggtgg taggcgcccg tgttgatggt gtaggagcag ttgcccagca  10080
cggaccagtt gaccacctgg tagtggggct ggatgacctc ggtgtagcgc agtcgactgt  10140
aggcgcgcgt gtcaaagatg taatcgttgc agaggcgcag caggtgctgg tagcccacga  10200
gcaggtgggg cggagggtag aggtagaggg gccagtgttc cgtggccggt tggcgggggg  10260
agaggttcat gagcatgagg cggtggtagc ggtagatgaa gcgggacatc caggcgatgc  10320
cgacggcgga gacggaggcg cgggtccact ggtgggcgcg gttccaaatg ttgcgcaccg  10380
ggcggaagag ctccacggtg taaatggatt gccccgtgag gcgggcgcag tcgagggcgc  10440
tctgtcaaaa agaaccgggt gtggttggtt ggtgtgtggt agcgatctat ctttctttgt  10500
gatcttggta gtgaagcctg ccaggctcca gcagggggcg tccgccgtct ttccttcctt  10560
ccctatctgg aggtgtgtct ctgttctctt ttttatttca tgtagccatg catcccgttc  10620
tgcggcagat gaagccgccg gccggcgccc tgggcgcgga gggggcgacg cgctctcggt  10680
cgccctcgcc gtcgctgacg cggccgcgcg aggaggggga gggcctggcg cggctgtcgg  10740
gcgcggcggc ccccgagcgg cacccacggg tgcagctcaa gcgagaggcc atggaggcct  10800
atgtgccgag gcagaatgcg ttccgcgagc gaccggggga ggagggggag gagatgaggg  10860
acctgcggtt ccgcgcgggg cgggagatgc agctggaccg ggagcgagtg ctccagcccg  10920
aggactttga ggggcgcgtg gaggaggcgg ggggagtgag cgcggcgcgg gcccacatga  10980
gcgcggccag cctggcccag gcctacgagc agacggtacg cgaggaggtc aacttccaaa  11040
agaccttcaa caacaacgtg cgcaccctgg tgagccggga cgaggtgacc atgggactga  11100
tgcacctgtg ggactttgtg gaggccttcc tgcagcaccc ccggtcccgc gcgctgaccg  11160
cgcagctgct gctgatcgcg cagcactgcc gggacgaggg catggtgaag gaggcgctgc  11220
tgagcctggg cgcgcccgag agccgctggc tggtggacct ggtgaacctg ctccagacca  11280
ttgtggtgca ggagcggtcc atgagcctga gcgagaaggt ggcggccatc aactactcgg  11340
tggcgaccct ggccaagcac tacgcgcgca agatctccac cttctacatg cgcgcggtgg  11400
tgaagctgct ggtgctggcc gacaacctgg gcatgtaccg caacaagcgg ctggagcgcg  11460
```

-continued

```
tggtcagcac ctcgcggcgg cgcgagctca atgacaagga agctcatgtt tggcctccgc  11520
cgggcgctgg ccggggaggg cgaggaggac ctggaggagg aggaggacct ggaggaggcg  11580
gaggaggagg agctggaaag aggaggagtt cggtccccgg ggaccgcggc gcgtgaggtg  11640
gcagtccccg ctgactgcga gcgatgaggg tgatgtgtac tgatggcaac catcccccttt  11700
tttaacaaca acagcagcat ggcggcgagc tctgaagctg ggcggcggc ggcgggggtg  11760
agcgcggcct ccctggcgcc cgagcgggcg acgcggatgc aggcgctgcc ctccctggac  11820
gagccttggg agcaggctct gcggcgcatc atggcgctga cggccgacgg gtctcggcgc  11880
ttcgcgagcc agcccctggc caaccgcatc ggggccatcc tggaggcggt ggtgcctccg  11940
cgcacgaacc cgacgcacga gaaggtgctg accgtggtga acgcgctgct ggagacctcg  12000
gccatccgcc cggacgaggc cggcatggtg tacgatgcgc tgctggagcg ggtctcccgc  12060
tacaacagcg gcaacgtgca gaccaacctg gaccggctgt cccaggacgt gcggcaggtg  12120
atcgcccagc gcgagcgctc gagcgccaac aacctgggca gcctggccgc gctgaatgcc  12180
ttcatcgcct cgctgcccgc aacggtggag cggggccagg agagctacct ggggttcctc  12240
agcgcgctgc ggctgctggt gagcgaggtg ccgcagacgg aggtgttccg ctcggggccg  12300
cacaccttcc tgcaggcggc gcggaacggt tccaagacgg tgaacctcaa ccaggccatg  12360
gagaacctgc ggcccctgtg gggctgcag gcccccgctg gggagcgcgg gcacgtgtcc  12420
tccctgctga cgcccaacac ccggctgctg ctgctcctgg tggctccctt cgcggaggag  12480
atgaacgtca gccggagctc ctacattggg cacctgctga cactctaccg cgagacgctg  12540
gccaacttgc atgtggacga gcgcacgtac caggagatca ccagcgtcag ccgggcgttg  12600
ggcgacgagg acgacgcggc gcggctgcag gccaccctca acttcttcct gaccaaccgg  12660
cagcggcggc tgccggcggc gtatgccctg accgccgagg aggagcgcat cctgcgctac  12720
gtgcagcagg ccgtgagcct gtacctgatg caggacgggg cgacggccac gggcgccctg  12780
gacgaggcca gccgcaacct ggagcccagc ttctacgcgg cgcaccggga cttcatcaac  12840
cgcctgatgg actacttcca tcgcgcggcc gcggtggcgc ccaactactt tatgaatgcc  12900
gtcctgaacc cccgctggct gccctcggag ggcttcttca ccggcgtgta tgacttcccg  12960
gagcaggacg agggggagga gcggccctgg gacgcctttg acagcgacga ggagggccgc  13020
ctcatgctgc ggtccgcagc ctcctcagag ccctcctcct ccttcacccc cctgcccctg  13080
accgaggagc cgccctcgcg gccctccacc ccggccctct cgcgcgtccc gtcccgggca  13140
tcctccctgc tctctctggc ctctctggga aagcgggagg gaggggactc gctcgcctac  13200
tcgccggcca cgcccaccta tggctctcgc tggggctcgc gccgctccag cctggccagc  13260
ggcgccgaca gcctggagtg ggacgcgctg ctggcccctc ccaaggatgt gaacgagcac  13320
ccaggcgccg ccgccggccg ccgccgccgc gcctcccgct cctccctgga ggaggacatc  13380
gacgccatca gcagccggct gttcacctgg cgcacgcgcg cccaggagat gggcctgccc  13440
gtggccagct tctcccgccg ccaccagccg cgccccgggg ccctcgaaga cgacgaggag  13500
gaggaagact ggcgccagga ccggttcttt cgcttcgaag cgcccgagga aaaccccttc  13560
cgccacatcg cccccaaggg gctgtaatgc aaaaaagcaa aataaaaaac ccctcccggt  13620
ccaactcacc acggccatgg ttgtccttgt gtgcccgtca gatgaggagg atgatgccag  13680
cagcgccgcc gcagggagcg tcgcctccgc cgtcctacga gagtgtggtg gggtcttcgc  13740
tcacggagcc tctttatgtg ccgccgcggt acctgggccc caccgagggg cggaacagca  13800
tccgttattc acagctcccg ccgctctacg ataccacaaa gatctatctg atcgataaca  13860
```

-continued

```
agtcggcgga tatcgccagt ctgaactacc aaaacaacca cagtgacttt ctcaccagcg  13920
tggtgcagaa cagcgacttc acgcccatgg aggcgagcac gcagaccatc aacctggatg  13980
agcgctcgcg ctggggcggg gagtttaaga gcattctgac caccaacatc cccaacgtga  14040
cccagtacat gttcagcaac agcttccggg tgcgcctgat gagcgcgcgc gataaagaga  14100
caaatgcccc cacctacgag tggttcaccc tgaccctgcc cgagggcaac ttctcggaca  14160
tcgcggtcat cgacctgatg aacaacgcga tcgtggagaa ctacctggcg gtggggcggc  14220
agcagggggt caaggaggag gacatcgggg tgaagatcga cacgcgcaac ttccgcctgg  14280
gctatgaccc ggagaccaag ctggtcatgc ccggcagcta caccaacatg gcctttcacc  14340
ccgacgtggt gctggcaccg ggctgcgcca tcgacttcac cttctcccgc ctaaacaacc  14400
tgctgggcat ccgcaagcgc taccctacc aggagggctt catgctgacc tacgaggacc  14460
tggcgggggg caacatcccc gcgctgctgg acctcaccac ctatgatcag gagaactcca  14520
gcaccatcaa gcccctgaag caggacagca agggtcgcag ctaccacgtg ggcgaggacc  14580
ccgaggcggg ggacaccttc acctactacc gcagctggta cctggcctac aactacgggg  14640
acccggccac gggcaccgcc tcccagacgc tgctggtctc cccggacgta acctgcggag  14700
tggagcaggt ctactggagc ctgccggacc tgatgcagga cccggtgacc ttccggccca  14760
gccagacgcc gagcaactac ccggtggtag ccacggagct actgccgctg cgctcccggg  14820
ccttctacaa cacccaggcc gtgtactccc agctcctgca gcaggccacc aacaacaccc  14880
tggtctttaa ccgcttcccg gagaaccaga tcctcctgcg cccgccagag tccaccatca  14940
cctccatcag cgagaacgtg ccctcgctga cggaccacgg cacgctgccg ctgcgtaaca  15000
gcatccccgg ggtgcagcgg gtaaccgtca ccgacgcgcg gcgccgcgtg tgtccctatg  15060
tgtacaagag tctcggggtg gtgaccccga gggtgctcag cagccgaacc ttctaaccga  15120
cagccctacc cgtcacaggg gagacagaga aaagacagcc agccccgcca tggccatcct  15180
cgtctcgccc agcaacaact ttggctgggg actgggcctg cgctccatgt acgggggcgc  15240
ccgccgcctg tccccggatc accccgtgat cgtccgacgc cactaccggg ccaactgggc  15300
cagtctgaag ggacgcgtgg cccccagcac catagcgaca acggatgacc ctgtggccga  15360
cgtggtcaac gcgatcgccg gcgccacccg ccgccggcgc cgccatcgtc gacgtcggag  15420
ggccgcgcgc gtctcctccg tggccgtcac cggggacccg gtggccgatg tggtcaacgc  15480
ggtggaggcg gtagcccggc gccgccgcgc gcggcgccgt tcttcgcgca tgcagaccac  15540
gggggacccc gtggcggatg tggtggcggc ggtggaagcg gtggcgcgcc ggaggcggag  15600
cacccggcgg cggcgcaggc gctccgcgcc ggccatcctg gggggtgcgcc gcagccgccg  15660
cctccgcaaa cgcacctcgt cctgagattt ttgtgttttg ttttttctgc ctcccgtggg  15720
tgaacaagtc catccatcca tccaacatcc gtggctgctg tgtctttgtc ttttctttgc  15780
gttgcgcccc agttgagccg gcaccgacgc gctcggccat ggccatctcg cgccgcgtga  15840
aaaaggagct gctgcaggcg ttggcgcccg aggtgtacgg ggcgcctaag aaggaggaga  15900
aggacgtcaa agaggagtcc aaagctgacc ttaaaccgct gaagaagcgg cgcaaggcca  15960
agcgggggtt gagcgacagc gacgaggtgc tggtgctggg cacgcgcccc aggcgccgct  16020
ggacggggcg gcgcgtgcgc gcccacctac cgcccggtgc cagcctcgcc tacgtcccgg  16080
gtcttcggag gtcgagcgcc accaagcgct ctgcggacga gttgtatgcg gacacggaca  16140
tcctgcagca ggcgtcccag cgcctgaacg aatttgctta tggcaagaga gcccggcggc  16200
```

-continued

```
agcggcgggc ccgcccctcg ccgacccccg cgtcccgcgg ccggaccacc aagcgctctt  16260
atgacgaggt cgtggcagac agtgacatcc tgcagcaact tggatccggg gaccgctcca  16320
atgagttctc ctatggcaag cggtcgctgc tgggggagtc aggagacacc gtcccggctg  16380
tggccgtccc gctggaggaa ggcaggaacc acacacccag cctgcagccg ctcaccgagc  16440
ccatgcccct ggtgtcccct cgcacggccg tcaagcgccg ggcgcccgcc gacgagccca  16500
ccgcctcact ggtccccacc gtgcaggtcc tggcccccaa gcgtcgtctg caggaggtgg  16560
tggtggagcc gcccgctcca gcacccacgc cgcccctagc cccgcggcgg tccagccggc  16620
gcatcattct ggctccgcgc cgggcgggcc ggccccaggc cgtcgtggcg ccgcagctca  16680
gcgcggccgc ggcgctggag cgggcggcgg ccgccgtgcc cctgccaccg gacacggagg  16740
acgacctggt ggagatggca gaggctgtcg ccgcgcccga ggtgctgccc agcctccccg  16800
tctccatcat gccgcccacc gccacggagg tggccctgcc cgtacagacc ccactgccgc  16860
ccgtggcggt ggccaagagc tccctgaccc ccggcctccg cgcgctgatg ggcaccgagc  16920
gggtgccggt tccagtcctg gaggcgcccc tggtggccat gcccgtgctc cgggccacca  16980
ccgcccgtgc cgagcccccg cgccgcgtgc cccgcagggc cgtgcgggac atcccggcca  17040
ggcagccccg cacggtatcc ctgcccgtgc tcacggagcc cggcccggcc accgcggtcg  17100
cctccgtgcg cgcggcagcc caagtcctgc aggcgccccc cgcccgaccg gccaccgtct  17160
ccgtgggggt gggcaccgag ccggtggtgc agtccatcac ggtcaagcgg tcaaagcgcc  17220
tgaccaagca ccatcggggt gcagaccatc gacgtcaccg tgcccaccgt ccgcactgtc  17280
agcgtgggca ccaacacgcc ccggctgagg agcgcctcgg tgggcgtcca gaccgctccc  17340
gagacccgct cccagggggt gcaggtggct ttccaaccag cgtgctagcc caccgcacac  17400
ccaggcaggt gcggctgacg gcggtggtgc cccccacccc gcgcgccccg gtggttccgg  17460
tggcccggcg cccgcggcgg ttccggtgcc tcccccagcc cctccagccc cgcgcgcgcc  17520
gcgtgcgcct cgcgccccca gagcgcctcg gcgtcgccgc cgtaccccgg tggcggtggc  17580
agcgccgccc gcccgcagcg gcggtccccc gccctcggct gccgaggcgg cccatcgtgc  17640
tgcccggggt gcgctatcat cccagtcagg ccatggctcc caccgcccaa cgcgtcatct  17700
ggcgttgatt tatttttgga gacctgactg tgttgtgttc cttaaatttt ttatcctcct  17760
cctcctctgc tgaagccaga cgatgctgac ctaccggttg cggctgcccg tgcggatgcg  17820
gagaccgaga ctccgcggtg ggttccgcgt ggcgcctcgg cgcagcggcg gcaggcggcg  17880
gtaccgccgg gggccgatga ggggtggcat cctgccggcg ctggtgccca tcatcgcggc  17940
atccatctgg gccatccccg gcatcgcctc ggtggcgatg agtgctagac aacgcaatta  18000
acggcgctgc tgtgtatgtg tgtcttccat gtgccttcct tccttcgttc ccaacggaac  18060
agcagcaccg tctccatgga ggacctaagc ttttccgcgt tggctccacg ctttggcacg  18120
cggccggtca tgggcacttg gagcgaaatc ggcacgagtc agatgaacgg cggcgcgctc  18180
agctggagca atatctggag cgggctgaag agctttggta gttctctggc ctccacggcc  18240
aacaaggcct ggaacagcgg gacggtgacg agcgtgcgca acaagttgaa ggatgccgac  18300
gtgcagggga agataggtga ggtcattgcc tccggggtcc acggtgccct ggacgtggcc  18360
aaccaggccg tctcccacgc cgtggaccgc cggtgcaaca gcagcagctg cggcagcagc  18420
agctcctccg ccagcagcag caacagatgg gcctcgtgga accctcctat gagatggaga  18480
cagacgagct gcctcctccc cccgaggacc tcttgcctcc tcctcctcct ccgccgcctg  18540
cctcggccac tcccgcgcgc caatcccgcg ggacgtcccg ccaagcgccc gccgccgccc  18600
```

-continued

```
aggagatcat catccgctcc gacgagcccc ctccctatga agagctgtat cccgacaagg  18660
ccgggatccc cgccaccttg gagctgcgtc ccgagaccaa actgcccgcc gtggcccaca  18720
ataagatgcg ccccccgccg ccgctcacca ccaccacctc ctccgctgcc gccgccgccc  18780
ccgccccggc ccccgcggct cctgtgcgtc ggcgtccggc cgcggctccg gccgcggctc  18840
cggcgagttc caaaggcccc ccaggtgggg gtccgcgcgc gcgggtggca aaacaaactc  18900
aacaccattg tgggactggg tgtccgcaca tgcaagcgcc gtcgttgtta ctgagagaga  18960
cagcatggag aaacaacaat gtctggattc aaataaagac acgcctattc ttccacggtg  19020
ctccgcgctg tgttattttc aacgggctgt ttccttttgc atctctgtgc catcgcgcca  19080
cggggaattc cgcaggatgg cgacgccgtc gatgatgccg cagtggtcct atatgcacat  19140
ctccgggcag gacgcgtccg agtacctgtc tcccgggctg gtgcagttct cccaggcgac  19200
ggagacctac tttaacctga acaacaagtt taggaacccc accgtcgcgc ccacccacga  19260
tgtgacgacg gagcgctcgc agcggctgca gctgcgcttc gtccccgtgg acaaggagga  19320
cactcagtac acatacaaga cccgcttcca gctggcggtg ggcgacaacc gcgtgttgga  19380
catggcgagc accttctttg acatccgggg aacgctggac cggggaccct ccttcaaacc  19440
gtactcgggc accgcgtaca acatcatggc tcccaagagc gctcccaaca actgtcaata  19500
tctagaccct aaaggtgaaa ctgaggctgg caaagttaat accattgctc aagcaagttt  19560
tgtgggtcct attgatgaaa ccacgggaga cattaaaatt acagaagaag aagacgaaga  19620
gaccaccatc gatcctttgt atgagcccca accccagctt ggtccaagct cgtggtcaga  19680
caatatacct tctgcgacta gcggagctgg aagagttctc aaacagacca caccgcgtca  19740
accttgttac ggttcttatg cctctccgac aaatattcac ggtgggcaaa cgaaggatga  19800
caaggttaca ccattgtact ttacaaacaa tcccgccacc gaagccgaag cactcgaaga  19860
aaatggatta aagccaaatg tcaccctata ctcagaggat gttgacctaa aagcaccaga  19920
tactcatctg gtctatgctg tgaatcaaac ccaggaattc gctcaatatg gacttggaca  19980
acaggccgct ccaaacaggg ccaattacat cggcttcagg gacaacttta tcgggctgtt  20040
gtactacaac agcaatggca accagggcat gctagccggt caggcctctc agctcaacgc  20100
ggtggtcgac ctgcaggaca ggaatcaccg aactagctac cagctcttcc tcgatagcct  20160
ctatgacagg tcgaggtact ttagcctgtg gaaccaggcc atcgattctt atgacaagga  20220
tgtgcgtgtg ctggaaaaca atggcgtgga ggacgagatg cccaactttt gctttcccat  20280
cggcgccatc gagaccaaca tgacatttac acagctcaaa aagagtgaga atggtggctc  20340
aagagccaca acctggacaa aggagaatgg ggatgatggc ggaaacggag cggagcacta  20400
cctgggcatc ggcaacctca acgccatgga gatcaatctc acggccaacc tctggcgcag  20460
cttcctctac agcaacgtgg cgctgtacct gcctgacaag tacaagtttt ccccgcccaa  20520
cgtccccatc gaccccaaca cgcactccta tgactacatc aacaagcgcc tgcccctcaa  20580
caacctcatt gataccttg tcaacatcgg ggcgcgctgg tccccggatg tcatggacaa  20640
cgtcaacccc ttcaaccacc accgcaacta cggcctgcgc taccgctccc agctcctggg  20700
caacggccgc tactgcaagt tccacatcca ggtgccgcaa aagttctttg ccctcaagag  20760
cctgctgctc ctgccggggg cgacctacac ctacgagtgg tccttccgca aggacgtcaa  20820
catgatcctc cagtccacgc tgggcaacga cctccgcgcg gacggggcca aaatcaacat  20880
cgagagcgtc aacctctacg ccagcttctt tcccatggcc cacaacaccg cctccaccct  20940
```

-continued

```
ggaggccatg ctgcgcaacg acaccaacaa ccaaaccttt attgacttcc tctcctccgc  21000
caacatgctc taccccatcc cggccaacgt caccaacctg cccatctcca ttcccagccg  21060
caactgggcc gccttccgcg gctggagctt cacgcggctg aagcacaacg agacccccgc  21120
cctgggctcg cccttcgacc cctactttac ctactcgggc tccatcccct acctggacgg  21180
gaccttctac ctgggccaca ccttccgccg catcagcatc cagttcgact cctccgtggc  21240
ctggccgggc aatgaccgcc tgctcactcc caacgagttc gaggtcaagc gcaccgtgga  21300
cggggagggc tacacggtgg cccagaccaa catgaccaaa gactggttcc tggtgcagat  21360
gctcgcccac tacaacatcg gctaccaggg ataccacctg ccagagggct accgcgaccg  21420
cacctactcc ttcctgcgca actttgagcc catgtgccgc caggtgcccg actacgccaa  21480
ccacaaagat gagtacctgg aggtgcccac caccaaccag ttcaacagca gcggctttgt  21540
atccgcggcc ttcaccgccg gcatgcgcga ggggcaccca taccccgcca actggcccta  21600
cccgctcatc ggcgaagacg ccgtgcagac cgtgacccag cgcaagttcc tctgcgaccg  21660
cacgctctgg cgcatcccct tctcctccaa cttcatgtcc atgggcaccc tcaccgacct  21720
gggccagaac ctcctctacg ccaactcggc ccacgccctc gacatgacct tcgaggtcga  21780
cgccatggat gaacccaccc tcttgtatgt tctgttcgag gtctttgacg tctgcggcgt  21840
gcaccagccg caccgaggcg tcatcgaggc cgtctacctg cgcacgccct tctccgccgg  21900
gaacgccacc acctaaggcg gagccgcgca ggcatgggca gcaccgagga cgagctccga  21960
gccatggcgc gcgacctcca gctgccccgc ttcctgggca cctttgacaa gtccttcccg  22020
ggcttcttgc aagagtccca gcgctgctgc gccatcgtca acacggccgc ccgccacacc  22080
ggaggccgcc actggctggc cgtcgcctgg gagcccgcct cgcgcacctt ctacttcttt  22140
gaccccttcg gcttctccga ccgggagctc gcccaggtct atgactttga gtaccagcgc  22200
ctgctgcgca agagcgccat ccagagcacc ccggaccgct gcctcacgct cgtcaagagc  22260
acccagagcg tgcagggacc gcacagcgcc gcctgcggac tcttctgcct cctcttcctc  22320
gccgcctttg cccgctaccc cgacagcccc atggcctaca atcccgtcat ggacctggtg  22380
gagggcgtgg acaacgagcg gctcttcgac gccgacgtcc agcccatctt ccgcgccaac  22440
caggaggcct gctacgcgtt cctcgctcgc cactccgcct acttccgcgc ccaccgccac  22500
gccatcatgg aacagacaca cctgcacaaa gcgctcgata tgcaataaag gctttttatt  22560
gtaagtcaaa aaggcctctt ttatcctccg tcgcctgggg gtgtatgtag atggggggac  22620
taggtgaacc cggacccgcc gtcggctccc ctccatcccc tcttctctca aaacaggctc  22680
tcatcgtcgt cctccgttcc cacggggaag atggtgttct gcacctggaa ctggggcccc  22740
cacttgaact cgggcaccgt cagtggaggc cgcgtctgca tcagggcggc ccacatctgt  22800
ttggtcagct gcagggccag catcacatcg gggcgctga tcttgaaatc acaattcttc  22860
tgggggttgc cgcgcgaccc gcggtacacc gggttgtagc actggaacac cagcaccgcg  22920
gggtgggtca cgctggccag aatcttgggg tcttccacca gctgggggtt cagcgccgcc  22980
gacccgctca gcgcgaaggg ggtgatcttg caggtctgcc ggcccagcag gggcacctgg  23040
cggcagcccc agccgcagtc gcacaccagc ggcatcagca ggtgcgtctc cgcgttgccc  23100
atccggggggt agcaggcctt ctggaaagcc ttgagctgct cgaaggcctg ctgcgccttg  23160
gagccctccg agtagaagag gccgcaggac cgcgccgaga aggtgttggg ggccgacccc  23220
acgtcgtggc tgcaacacat ggccccgtcg ttgcgcagct gcaccacgtt gcggccccag  23280
cggttggtgg tgatcttggc gcgctcgggg gtctcgcgca gggcgcgctg cccgttctcg  23340
```

-continued

```
ctgttgagat ccatctccac cagctgctcc ttgttgatca tgggcagccc gtgcaggcag  23400
tgcagcccct ccgagccgct gcggtgctgc cagatcacgc acccgcaggg gttccactcg  23460
ggcgtcttca gacccgccgc cttcaccaca aagtccagca ggaagcgggc catcactgtc  23520
agcaggctct tttgcgtgct gaaggtcagc tggcagctga tcttgcgctc gttcagccag  23580
gcttgggccc cgcgccggaa gcactccagg gtgctgccgt ccggcagcag cgtcaggccc  23640
ttgacatcca ccttcagggg gaccagcatc tgcacagcca gatccatggc ccgctgccac  23700
ttctgctcct gagcatccag ctgcagcagc ggccgggcca ccgccgggct cggggtcacc  23760
gggcgcgggg ggcgggcccc ctcctcttcc tccccatctt cgcccttcct cctcgcgggc  23820
cgcgccgtcg ccgctgccgt ctcttcagcc tcgtcctcct cctcctcgct gaccaggggc  23880
ttggcacgcg cgcgcttccg ccgctcctgc acgggcggag aggccgcgcg cttgcggcct  23940
cccccgcgcc ggctgggggt cgcgacagga gcgtcgtcca caatcagcac cccctcttcc  24000
ccgctgtcat agtcagacac gtccgaatag cggcgactca ttttgcttcc cctagatgga  24060
agaccagcac agcgcagcca gtgagctggg gtcctccgcg gccccgaccc ttccgccgcc  24120
accaccgccg ccacctccgc ccacgtcacc gccaccttca ctgcagcagc ggcagcagga  24180
gcccaccgaa accgatgacg cggaggacac ctgctcctcg tcctcctcgt cctccgcctc  24240
cagcgagtgc ttcgtctcgc cgctggaaga cacgagctcc gaggactcgg cggacacggt  24300
gctcccctcc gagccccgcc gggacgagga ggagcaggag gaggactcgc ccgaccgcta  24360
catggacgcg gacgtgctgc agcgccacct gctgcgccag agtaccatcc tgcgccaggt  24420
cctgcaggag gccgccccccg gcgcagccgc ggaggccgcc gaggcgccct cggtggcgga  24480
gctcagccgc cgcctggaag cggccctctt ctcccccgcc acgccgccgc ggcgccagga  24540
gaacggaacc tgcgccccgg acccccgcct caacttctac ccggtcttca tgctgcccga  24600
ggccctggcc acctacctcc tcttcttcca caaccaaaag atccccgtca gctgccgcgc  24660
caaccgccca cgagccgacg cgcactggcg gctgcccagt gggacccct tacctgacta  24720
tccaaccacc gacgaggttt acaagatctt tgagggcctg ggggacgagg agccggcctg  24780
cgccaaccag gacctgaaag agcgcgacag cgtgttagtc gagctcaagc tggacaaccc  24840
ccgcctggcg gtggtcaagc agtgcatcgc cgtcacccac ttcgcctacc cggccctggc  24900
gctgccaccc aaggtcatga gcacgctcat gcagaccctg ctggtgcgcc gcgcgagccc  24960
actccccgac gagggcgaga cgcccctcga ggacctcctg gtggtcagcg acgagcagct  25020
ggcccgctgg atgcacacct cggaccccaa ggtcctggag gagcggcgca agaccgtcac  25080
cgccgcctgc atggtcacgg tgcagctcca ctgcatgcac accttcctca cctcccgcga  25140
gatggtgcgc cgcctcggag agtgcctcca ctacatgttc cgccagggct acgtcaagct  25200
agctagcaag atcgccaata tggaactctc taacctggtc tcctacttgg gcatgctgca  25260
cgaaaacagg ctcggtcagc acgtgctcca ccacaccctc aagcatgagg cgagacgcga  25320
ctacgtccgg gacaccattt acctatacct ggtctatacc tggcagaccg ccatgggggt  25380
ctggcagcag tgcctcgagg accgaaacct gcgcgccctg gaaacgtctc tggctcgcgc  25440
tcgccagagc ctgtggacgg gctttgatga gcgcactatc gcgcaggacc tcgccgcgtt  25500
ccttttcccc accaagctcg tagagaccct gcagcgctcg ctccccgact ttgccagcca  25560
gagcatgatg catgccttcc gctccttcgt cctcgagcgc tccggcatcc tgcccgccgt  25620
ctgcaacgcg ctcccctctg actttgtgcc caccgtctac cgcgagtgcc cgccgcccct  25680
```

-continued

```
ctgggctcac tgctacctcc tgcgcctcgc caacttcctc atgtaccact gcgacctcgc  25740

cgaggacacc tccggcgagg gcctctttga gtgctactgc cgctgcaacc tctgcgcacc  25800

gcaccgctgc ctcgccacca acaccgccct cctcaacgag gtgcaagcca tcaacacctt  25860

tgagctccag cggcccccca agcccgacgg caccctgcca ccgcccttca agctgacccc  25920

cggtctctgg acctccgcct tcctccgcca ctttgtctcc gaggactacc actcggaccg  25980

catcctcttc tacgaggacg tgtcccgccc ccccagggtg gagccctccg cctgcgtcat  26040

cacgcactcg gccattctcg cgcaattgca tgacatcaaa aaggccaggg aagagttttt  26100

gctgaccaaa ggccacggcg tctacctaga cccccacacc ggagaggagc tcaacaccgc  26160

cgccccgtcc accgcccacc atgccgcccc tccggaggaa gcccatccgc agcagcacca  26220

gcaccagcag cagccgagcc accgccgccg ccaccaccgc tccagctacg cagaccgtgt  26280

ccgaagcgag ctccacgcct acggcggtgc gaccggttcc tcccgcgacc ctgtctctgg  26340

cggatgctct gccagaggaa cccactcccg cgatgctgct cgaagaagag gctctcagca  26400

gcgagaccag cggcagctcc gaaggcagtt tgctcagtac cctcgaggaa ctggaggagg  26460

aggaggaacc ggtcacaccg acgaggccat ccaagccctc ctacaccaac agcagcagca  26520

gcaagagcat cagccagcgc aggaactccg tcgtccccag cgaggctcgt agatggaatc  26580

agacatccat ccaccggagt agccagccag gtaggacacc tccgccctcg gcccgccgac  26640

gctcctggcg ccgctaccgc cacgacatcc tctcggccct ggagtactgc gccggagacg  26700

gagcctgcgt gcgccggtac ctactctacc accacaacat caacatccct tccaagatca  26760

tccgttacta caaatcctct tcccgttcca gcgatctcca ggaaggccgc agcagcggcg  26820

gcagcagaac cagcccacgt cagccagctg agagctaaga tcttccccac gctgtacgcc  26880

atcttccagc agagccgcgg cggccaggac gccctcaaaa tcaggaaccg caccctgcgc  26940

tccctcacca agagctgtct gtatcaccgc gaggaggcca agctggaacg cacgctctcg  27000

gacgcagaag ctctcttcga gaagtactgc gctcggcagc ggcagacccg ccggtattta  27060

aggagcggac cctgcgtgcg gacacaccat gagcaaacaa atccccaccc cgtacatgtg  27120

gtcttatcag ccacaatctg ggcgtgccgc cggtgcctcc gtcgattact ccacccgcat  27180

gaattggctc agtgccgggc cttccatgat tggccaggtc aatgacatcc gacacaccag  27240

gaaccagatt ctcattcgcc aggcccttat caccgagacg ccacgccccg tccaaaatcc  27300

cccgtcctgg cccgccagcc tgttgcctca gatgacgcaa ccgcccaccc acctgcacct  27360

gccgcgtaac gaaattttgg aaggcagact gactgacgcc ggcatgcaat tagccggggg  27420

cggagccctc gcacccagag acttatatgc cctgaccctc cgcggcagag gcatccagct  27480

caacgaggac ctacccctct cggcgagcac tctccggccg gacggcatct tccagctcgg  27540

aggcggaggc cgctcctcct tcaaccccac cgacgcctac ctgacgctgc agaactccag  27600

ctcccttccc cgcagcggcg gcatcggcag cgagcaattt gtccgcgagt tcgtgcccac  27660

ggtctacatc aaccccttct ccggaccgcc cgggacctac cccgaccagt tcatcgccaa  27720

ctacaacatc ctaacggact ctgtagcagg ctatgactga cggtccccag ggtcagcagc  27780

ggctgcggga gctcctcgac cagcaccgcc gccagtgccc taaccgctgc tgcttcgcca  27840

gggaagggat tcacccggag tacttttgca tcacccgcga gcactttgag gccgagtgca  27900

tccccgactc tctgcaagaa ggccacggtc tgcgcttcag cctccccacg cgctacagcg  27960

accgccgcca ccgcgatgga gaccgcacca tcctcacttc gtactactgc ggccctgctt  28020

ctttcaaagt tcgctgtctc tgcggccatc ctgctcctca ccctcttctt ctcgaccttc  28080
```

-continued

```
tgtgtgagct gtacaaccgc tcgtagcgtc agcccctaca cctcccctcg cgtccaattt  28140
ctgtccgaca tagaaccaga ctctgactct tactcgggct ctggctctgg ggacgatgaa  28200
gattatgaat atgagctggc taccaacaca ccgaacgaag acattctagg cagcatagtc  28260
atcaacaacc agatcgggcc caagaccctg gccctgggat acttttatgc cgccatgcag  28320
tttgtcttct ttgccatcat catcatcgtc ctcatcctct actaccgccg ctacgtgctg  28380
gccaccgccc tcatcgtgca gcgccagatg tggtcctccg aggccgtcct gcggaaaacc  28440
ttctcggcca ccgttgtggt tactccccca aaacaagtca ccccctgcaa ctgctcctgc  28500
cgcttcgagg agatggtgtt ctactacacc acctccgtct tcatgccctg gtgggcctca  28560
tcctcctgct caccgccatg gtccgcctgg ccaactggat agtggatcag atgcccagca  28620
ggaaccgcgc cccgccgctg ccaccgcccc tcacctatgt gggaccctgc gccgaggacc  28680
acatctacga tgagccaacc gtagggcaat acgtacagat gaagtagctc cccctctttc  28740
ccattccccc atttttctct attcaataaa gttgcttacc tgagttcatc cacactcggt  28800
ctgccagtgc agtctatcca tgcgccgttt tccatactca catagcgcag ccgcgcacgc  28860
ctcgccaggt gacgaaactg tcgaaatgta acatttcgcg cttctgtcag cagcaccccg  28920
ttatagacca gttccaccat gggaccgaag aagcagaagc gcgagctacc cgaggacttc  28980
gatccagtct acccctatga cgtcccgcag ctgcagatca atccaccctt cgtcagcggg  29040
gacggattca accaatccgt ggacggggtg ctgtccctgc acatcgcacc gcccctcgtt  29100
tttgacaaca ccagggccct caccctggcc ttcgggggag gtctacagct ctcgggcaag  29160
cagctcgtcg ttgccaccga gggctcgggg ctaaccacca acccggatgg caagctggtt  29220
ctcaaagtca agtcccccat caccctgacc gccgagggca tctccctgtc cctgggtccc  29280
ggtctttcta actcagagac cggcctcagt ctgcaagtca cagctcccct gcagttccag  29340
ggcaacgccc tcactcttcc cctcgccgcc ggtctccaaa acaccgatgg tggaatgggt  29400
gtcaaactgg ggagcggtct caccacggac aacagtcagg cggtgaccgt tcaggtggga  29460
aatggacttc agctgaacgg cgaaggacaa ctcaccgtcc ccgccacggc ccctttagtc  29520
tcagggagcg caggcatctc tttcaactac tccagcaatg acttcgtctt agacaatgac  29580
agtctcagtt tgaggccaaa ggccatctct gtcacccctc cgctgcagtc cacagaggac  29640
acaatctccc tgaattattc taacgacttt tctgtggaca atggcgccct caccttggct  29700
ccaactttca aaccctacac gctgtggact ggcgcctcac ccacagcaaa tgtcattcta  29760
acaaacacca ccactcccaa cggcaccttt ttcctatgcc tgacacgtgt gggtgggtta  29820
gttttgggtt cctttgccct gaaatcatcc atcgacctta ctagtatgac caaaaaggtc  29880
aattttattt ttgatggggc aggtcggctt cagtcagact ccacttataa agggagattt  29940
ggatttagat ccaacgacag cgtaattgaa cccacagccg caggactcag tccagcctgg  30000
ttaatgccaa gcacctttat ttatccacgc aacacctccg gttcttccct aacatcattt  30060
gtatacatta atcagacata tgtgcatgtg gacatcaagg taaacacact ctctacaaac  30120
ggatatagcc tagaatttaa ctttcaaaac atgagcttct ccgccccctt ctccacctcc  30180
tacgggacct tctgctacgt gccccgaagg acaactcacc gtccccgcca cggccccttt  30240
agtctcaggg agcgcaggca tctctttcaa ctactccagc aatgacttcg tcttagacaa  30300
tgacagtctc agtttgaggc caaaggccat ctctgtcacc cctccgctgc agtccacaga  30360
ggacacaatc tccctgaatt attctaacga cttttctgtg gacaatggcg ccctcacctt  30420
```

-continued

```
ggctccaact ttcaaaccct acacgctgtg gactggcgcc tcacccacag caaatgtcat  30480
tctaacaaac accaccactc ccaacggcac ctttttccta tgcctgacac gtgtgggtgg  30540
gttagttttg ggttcctttg ccctgaaatc atccatcgac cttactagta tgaccaaaaa  30600
ggtcaatttt atttttgatg gggcaggtcg gcttcagtca gactccactt ataaagggag  30660
atttggattt agatccaacg acagcgtaat tgaacccaca gccgcaggac tcagtccagc  30720
ctggttaatg ccaagcacct ttatttatcc acgcaacacc tccggttctt ccctaacatc  30780
atttgtatac attaatcaga catatgtgca tgtggacatc aaggtaaaca cactctctac  30840
aaacggatat agcctagaat ttaactttca aaacatgagc ttctccgccc ccttctccac  30900
ctcctacggg accttctgct acgtgcccca gagtgcctag agaaccctgg ccgtcagccg  30960
gcctcccct tcccaggcca cccggtacac cacccgctcc atgtttctgt atgtgttctc  31020
ctcccgccgc ttgtgcagca ccacctcccg ctgctcgagc tgaggatccg tgatggacac  31080
aaagccagga agacacatcc tcagctccgt gggggcgtcc aacaactgtt tatgtaaagg  31140
aaaataaaga ctcagagaaa atccaagttc atatgatttt tcttttattg attgggggaa  31200
ttgattcagg tggggtgtgc ataatcacaa aaatcacatc agcaggtaca cacctgagac  31260
atcagacagg ggtaaggaca gcgcctcagc ttctggaaca gacatcagaa atatttaatc  31320
tgctggtagc taacactcct tcccaacacc atacactcct ggagggccct ctgcctctcc  31380
tcctcccgct ccgcgtccct ctgccgggac caccactccc cctccgtgaa ctgctgcttc  31440
ctcccccgcc gctgcgcccc gatggcctcc gccgccagct tcagccagtg ccgcaagcgc  31500
tgggcgcagc gccgagccac cggctcgctc agctcgtggc agcgccggca caccagcact  31560
atgtaattgg catagtcccc gtcacagtag atgacctccc cccagtggaa catgcgcaac  31620
agcttcagat cacagtcata catgatcttt atgtacatca ggtgggcgcc tcgaaacatc  31680
acactgccca cgtacatcac gcgactcacg ctgggcaggt tcaccgcctc cctgaaccac  31740
cagaagatgc gattgtactc gcagccccgg atgatctcgc gcatcaggga gcgcatcacc  31800
acctgccccg cgcggcactc cagactggac cttttcagac agtggcaatg aaagttccac  31860
agcgtcgcgc ccgcacagcg tctccgggct gaaacatatc tgctccagct ccaaccccc  31920
acacaggctg tactgcagga aaatccattc ttgatgggaa aggatgtagc gccaggggac  31980
cacaatctcc aaacagggaa caaaacatac cgcggcccgg ctgttgcgca cggcccccac  32040
cggatgcaac gtgctcacgg agcagatacg ggtgggacag cggcccacgt ctcatagcaa  32100
gtcaagtccg gaagtggcac ggggttcgcc accactgcta ctgctgccgc tgcgccacca  32160
gctccatcgg ctcctccatc ctcctcctgt tccatcggct gaggtgctgc ctcctcctcc  32220
tcctgccgct gctccatcat gctcgtctgc ggtcatcagg agtcaaaaaa ttcattggcc  32280
accgcacgca gagagaacat ggagcgcagg ggcccaggtg cccggcccgt gcgctcgctc  32340
aactccccca gcaggtactc atagagatgc tcctccaaat ccaccgcaaa ccaggcatgc  32400
agaaactctt ccgttcgagg accgcccacg gtaaagacat agccctcccg caccttcacc  32460
gctgccagct gcacgcgctc atgtcgctgg gagtacaccc ggacccgggc ctggatgtac  32520
tccagcacct gatcgctcag acacctcaca gagatgccag cctgagccag cttctcatag  32580
agaggtggct gaatcttgag cttgaagcag cgagcggcta ggcactcccc gcccccttgg  32640
aacagggcgg ccgggtcagc catggacttc ctctacatcc ggggtcctgg ccacctcaca  32700
aactatctgg ccaatcgcct gaccacgggt caccaggtaa ggatgatgtc cgttgttgcg  32760
aatgagaatg ctcagaggtg actcggtagc gttatcaatc acgtccccaa aggtccaaag  32820
```

```
gtcccagtta gaagtcaggt gcttcagacc gcagacacgc ccatagcaac cagtgggaaa  32880

agccagcaag agatccgtgg gcacatgcac cgaagctccc gcaggaatct ccacccactc  32940

cgaggcgtag accgtgtaag ctacacaccc cgcctcccga gtgggagcag aagcattctc  33000

gctcagccga aagaacttca gggtggcctg catatcctct tttactcact tgttagcagc  33060

tccacacaga ccagggttgt gttggcggga ataggcagca ggggtacgtc cccagtgagg  33120

gacacctgga tggggggcag aggattgatg ccaggaagca gcaggtactg ggaaacagag  33180

accagatccc tcctctgaaa aatctcgctc agtcggacaa acacagcaaa cccagtgggc  33240

acgtagacta gcacattaaa aaggatcacg ctgggctgtt ctgacgtcag caccagatgt  33300

cgggacgtgc gcagatgaat gcggttctga tgaattaccg gaggcctctc acccgcagcc  33360

aacagcagac cgggctgctg atgcggtccc gcagacatat atgagttcaa tgtgtgtctt  33420

ttttctaaac gtctagtgag tgtgctcgtc ctgctcctgc caatcaaaat ccgggcacca  33480

gggctggtgg ttggacccga tgaagaagcg aggagaggcg gcctcctgag tgtgaagagt  33540

gtcccgatcc tgccacgcga ggtaggcgaa gtacagatag agcacggcga gaacagtcag  33600

caccgcggcc agcagcagtc ggtcgtgggc catgagaggg ggctgatggg aagatggccg  33660

gtgactcctc tcgccccgct ttcggtttct cctcgtctcg ctctcagtgt ctctctctgt  33720

gtcagcgccg agacgagtgt gagcgaacac cgcgagcggg ccggtgatat acccacagcg  33780

gatgtggcca cgcctgcggt cggttaatca gtaccccatc gtccgatcgg aattcccccg  33840

cctccgcgtt aacgattaac ccgcccagaa gtcccgggaa ttcccgccag ccggctccgc  33900

cgcgacctgc gactttgacc ccgcccctcg gactttgacc gttcccacgc cacgtcattt  33960

tcccacgcga cgtcacgttc ccacgctacg tcacacccct ctccaccaat caccgcccgc  34020

cgcccccaac cctctccgcc aatcaccacg ccacaaaagg ggcaataaaa gtgtgcggta  34080

tattattgat gatg                                                    34094
```

<210> SEQ ID NO 2
<211> LENGTH: 44
<212> TYPE: DNA
<213> ORGANISM: Porcine Adenovirus Type 3

<400> SEQUENCE: 2

```
gcggatcctt aattaacatc atcaataata taccgcacac tttt                      44
```

<210> SEQ ID NO 3
<211> LENGTH: 32
<212> TYPE: DNA
<213> ORGANISM: Porcine Adenovirus Type 3

<400> SEQUENCE: 3

```
cacctgcaga tacacccaca cacgtcatct cg                                  32
```

<210> SEQ ID NO 4
<211> LENGTH: 32
<212> TYPE: DNA
<213> ORGANISM: Porcine Adenovirus Type 3

<400> SEQUENCE: 4

```
cacctgcagc ctcctgagtg tgaagagtgt cc                                  32
```

<210> SEQ ID NO 5
<211> LENGTH: 20
<212> TYPE: DNA

-continued

```
<213> ORGANISM: Porcine Adenovirus Type 3

<400> SEQUENCE: 5

gactgacgcc ggcatgcaat                                              20


<210> SEQ ID NO 6
<211> LENGTH: 27
<212> TYPE: DNA
<213> ORGANISM: Porcine Adenovirus Type 3

<400> SEQUENCE: 6

cggatcctga cgctacgagc ggttgta                                      27


<210> SEQ ID NO 7
<211> LENGTH: 27
<212> TYPE: DNA
<213> ORGANISM: Porcine Adenovirus Type 3

<400> SEQUENCE: 7

cggatccata cgtacagatg aagtagc                                      27


<210> SEQ ID NO 8
<211> LENGTH: 20
<212> TYPE: DNA
<213> ORGANISM: Porcine Adenovirus Type 3

<400> SEQUENCE: 8

tctgactgaa gccgacctgc                                              20
```